(12) United States Patent
Avery et al.

(10) Patent No.: US 12,201,817 B2
(45) Date of Patent: Jan. 21, 2025

(54) SPACER ASSEMBLY FOR DRUG DELIVERY DEVICE

(71) Applicant: Becton, Dickinson and Company, Franklin Lakes, NJ (US)

(72) Inventors: Richard James Vincent Avery, Warwick (GB); Malcolm Stanley Boyd, Wellesbourne (GB); Oliver Charles Gazeley, Leamington Spa (GB); Gareth James Lewis, High Wycombe (GB); David Aubrey Plumptre, Droitwich (GB); James Alexander Senior, Warwick (GB)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/739,816

(22) Filed: May 9, 2022

(65) Prior Publication Data
US 2022/0257867 A1 Aug. 18, 2022

Related U.S. Application Data

(63) Continuation of application No. 16/160,231, filed on Oct. 15, 2018, now Pat. No. 11,357,918.
(Continued)

(51) Int. Cl.
*A61M 5/315* (2006.01)
*A61M 5/142* (2006.01)
(Continued)

(52) U.S. Cl.
CPC .... *A61M 5/31505* (2013.01); *A61M 5/14248* (2013.01); *A61M 5/2033* (2013.01);
(Continued)

(58) Field of Classification Search
CPC .... A61M 2005/31516; A61M 5/31505; A61M 5/14248; A61M 5/2033; A61M 5/2459;
(Continued)

(56) References Cited

U.S. PATENT DOCUMENTS

| 5,062,830 A | 11/1991 | Dunlap |
| 6,135,979 A | 10/2000 | Weston |

(Continued)

FOREIGN PATENT DOCUMENTS

| CN | 1951509 A | 4/2007 |
| EP | 1944048 A1 | 7/2008 |

(Continued)

*Primary Examiner* — Kevin C Sirmons
*Assistant Examiner* — Leah J Swanson
(74) *Attorney, Agent, or Firm* — The Webb Law Firm

(57) ABSTRACT

A drive assembly for a drug delivery system including a plunger member configured to engage and move a stopper within a container, a biasing member configured to move the plunger member, and an adjustable spacer assembly positioned between the plunger member and the stopper. The spacer assembly includes a spacer element attached to the stopper and at least one shim or includes a spacer element and a holder to which the spacer element is attached. The holder may be attached to the stopper and the spacer element may be attached to the holder by a threaded engagement. Also, a drug delivery system for injecting a medicament, the system including a container configured to receive a medicament, the container comprising a stopper configured to move within the container and a closure, a drive assembly as described above, and a needle actuator assembly.

16 Claims, 74 Drawing Sheets

Related U.S. Application Data

(60) Provisional application No. 62/572,704, filed on Oct. 16, 2017.

(51) Int. Cl.
  *A61M 5/145* (2006.01)
  *A61M 5/20* (2006.01)
  *A61M 5/24* (2006.01)
  *A61M 5/31* (2006.01)

(52) U.S. Cl.
  CPC ...... *A61M 5/2459* (2013.01); *A61M 5/31511* (2013.01); *A61M 5/31515* (2013.01); *A61M 5/3157* (2013.01); *A61M 5/31585* (2013.01); *A61M 2005/14256* (2013.01); *A61M 5/1454* (2013.01); *A61M 5/14566* (2013.01); *A61M 2005/247* (2013.01); *A61M 2005/3128* (2013.01); *A61M 5/3146* (2013.01); *A61M 2005/31516* (2013.01); *A61M 2205/584* (2013.01); *A61M 2207/00* (2013.01)

(58) Field of Classification Search
  CPC .......... A61M 5/31511; A61M 5/31515; A61M 5/3157; A61M 5/31585; A61M 5/1454; A61M 5/14566; A61M 5/3146; A61M 2005/14256; A61M 2005/247; A61M 2005/3128; A61M 2205/584; A61M 2207/00; A61M 2005/31508; A61M 2005/3151
  See application file for complete search history.

(56) References Cited

U.S. PATENT DOCUMENTS

| | | |
|---|---|---|
| 6,371,939 B2 | 4/2002 | Bergens et al. |
| 6,517,517 B1 | 2/2003 | Farrugia et al. |
| 6,620,133 B1 | 9/2003 | Steck |
| 6,837,876 B2 | 1/2005 | Bally et al. |
| 7,128,728 B2 | 10/2006 | Kirchofer et al. |
| 7,357,791 B2 | 4/2008 | Kirchofer et al. |
| 7,416,540 B2 | 8/2008 | Edwards et al. |
| 7,637,891 B2 | 12/2009 | Wall |
| 7,648,482 B2 | 1/2010 | Edwards et al. |
| 7,648,483 B2 | 1/2010 | Edwards et al. |
| 7,670,314 B2 | 3/2010 | Wall et al. |
| 7,749,195 B2 | 7/2010 | Hommann |
| 7,862,543 B2 | 1/2011 | Potter et al. |
| 7,879,007 B2 | 2/2011 | Hommann |
| 7,901,377 B1 | 3/2011 | Harrison et al. |
| 7,918,823 B2 | 4/2011 | Edwards et al. |
| 7,927,303 B2 | 4/2011 | Wyrick |
| 8,016,788 B2 | 9/2011 | Edwards et al. |
| 8,128,597 B2 | 3/2012 | Cross et al. |
| 8,231,572 B2 | 7/2012 | Carter et al. |
| 8,277,412 B2 | 10/2012 | Kronestedt |
| 8,277,414 B2 | 10/2012 | Barrow-Williams et al. |
| 8,303,574 B2 | 11/2012 | Gray et al. |
| 8,313,463 B2 | 11/2012 | Barrow-Williams et al. |
| 8,313,466 B2 | 11/2012 | Edwards et al. |
| 8,323,250 B2 | 12/2012 | Chong et al. |
| 8,376,998 B2 | 2/2013 | Daily et al. |
| 8,409,148 B2 | 4/2013 | Fiechter et al. |
| 8,469,933 B2 | 6/2013 | Zhang et al. |
| 8,545,458 B2 | 10/2013 | Gagliardoni et al. |
| 8,551,056 B2 | 10/2013 | Gagliardoni et al. |
| 8,551,057 B2 | 10/2013 | Gagliardoni et al. |
| 8,585,658 B2 | 11/2013 | Forstreuter |
| 8,591,465 B2 | 11/2013 | Hommann |
| 8,668,675 B2 | 3/2014 | Chase et al. |
| 8,734,394 B2 | 5/2014 | Adams et al. |
| 8,784,380 B2 | 7/2014 | Wall |
| 8,905,974 B2 | 12/2014 | Carter et al. |
| 8,915,879 B2 | 12/2014 | Smith et al. |
| 8,915,882 B2 | 12/2014 | Cabiri |
| 8,920,374 B2 | 12/2014 | Bokelman et al. |
| 8,920,377 B2 | 12/2014 | Edwards et al. |
| 8,939,935 B2 | 1/2015 | O'Connor et al. |
| 8,939,943 B2 | 1/2015 | Edwards et al. |
| 8,986,259 B2 | 3/2015 | Helmer et al. |
| 8,992,476 B2 | 3/2015 | Shang et al. |
| 8,998,858 B2 | 4/2015 | Chong et al. |
| 9,011,379 B2 | 4/2015 | Hariharesan et al. |
| 9,017,293 B2 | 4/2015 | Edhouse et al. |
| 9,061,097 B2 | 6/2015 | Holt et al. |
| 9,101,706 B2 | 8/2015 | Gonnelli et al. |
| 9,149,575 B2 | 10/2015 | Cabiri |
| 9,174,006 B2 | 11/2015 | Vosseler et al. |
| 9,180,244 B2 | 11/2015 | Anderson et al. |
| 9,205,188 B2 | 12/2015 | Lanigan et al. |
| 9,205,189 B2 | 12/2015 | Graf et al. |
| 9,238,101 B2 | 1/2016 | Hariharesan et al. |
| 9,254,373 B2 | 2/2016 | Hordum |
| 9,259,532 B2 | 2/2016 | Cabiri |
| 9,283,318 B2 | 3/2016 | Yavorsky et al. |
| 9,364,610 B2 | 6/2016 | KraMer et al. |
| 9,364,611 B2 | 6/2016 | KraMer et al. |
| 9,446,193 B2 | 9/2016 | Geipel et al. |
| 9,446,195 B2 | 9/2016 | Kramer et al. |
| 9,463,280 B2 | 10/2016 | Cabiri |
| 9,545,477 B2 | 1/2017 | Chong et al. |
| 9,566,384 B2 | 2/2017 | Gyrn et al. |
| 9,623,183 B2 | 4/2017 | Jennings et al. |
| 2005/0124940 A1 | 6/2005 | Martin et al. |
| 2008/0039789 A1* | 2/2008 | Wyrick ............... A61M 5/2033 604/110 |
| 2010/0028046 A1 | 2/2010 | Abe et al. |
| 2013/0060196 A1 | 3/2013 | O'Connor et al. |
| 2013/0066274 A1 | 3/2013 | O'Connor et al. |
| 2013/0237916 A1 | 9/2013 | Hanson et al. |
| 2013/0304021 A1 | 11/2013 | Cabiri et al. |
| 2013/0310746 A1 | 11/2013 | Wozencroft |
| 2013/0338593 A1 | 12/2013 | Wozencroft |
| 2014/0046259 A1 | 2/2014 | Reber et al. |
| 2014/0128815 A1 | 5/2014 | Cabiri et al. |
| 2014/0148784 A1 | 5/2014 | Anderson et al. |
| 2014/0200510 A1 | 7/2014 | Agard et al. |
| 2014/0207073 A1 | 7/2014 | Shang et al. |
| 2014/0213975 A1 | 7/2014 | Clemente et al. |
| 2014/0236086 A1 | 8/2014 | Levesque et al. |
| 2014/0296787 A1 | 10/2014 | Agard et al. |
| 2014/0316376 A1 | 10/2014 | Wall |
| 2014/0364808 A1 | 12/2014 | Niklaus et al. |
| 2015/0032084 A1 | 1/2015 | Cabiri |
| 2015/0057613 A1 | 2/2015 | Clemente et al. |
| 2015/0080800 A1 | 3/2015 | Cronenberg |
| 2015/0133855 A1 | 5/2015 | Smith et al. |
| 2015/0141920 A1 | 5/2015 | O'Connor et al. |
| 2015/0306306 A1 | 10/2015 | Gonnelli et al. |
| 2015/0314073 A1 | 11/2015 | Shang et al. |
| 2016/0008548 A1* | 1/2016 | Plumptre .......... A61M 5/31571 604/218 |
| 2016/0030664 A1 | 2/2016 | Yodfat et al. |
| 2016/0030665 A1 | 2/2016 | Cabiri |
| 2016/0058941 A1 | 3/2016 | Wu et al. |
| 2016/0082182 A1 | 3/2016 | Gregory et al. |
| 2016/0082189 A1 | 3/2016 | Anderson et al. |
| 2016/0121044 A1 | 5/2016 | Curtis |
| 2016/0206809 A1 | 7/2016 | Kamen et al. |
| 2016/0228634 A1 | 8/2016 | Cupicha et al. |
| 2016/0250422 A1 | 9/2016 | Koch et al. |
| 2016/0256627 A1 | 9/2016 | Gray et al. |
| 2016/0317736 A1 | 11/2016 | Schabbach et al. |
| 2016/0317737 A1 | 11/2016 | Schabbach et al. |
| 2016/0317738 A1 | 11/2016 | Cross et al. |
| 2016/0346478 A1 | 12/2016 | Bar-El et al. |
| 2016/0354553 A1 | 12/2016 | Anderson et al. |
| 2017/0000951 A1 | 1/2017 | Smith et al. |
| 2017/0028132 A1 | 2/2017 | Cronenberg et al. |
| 2017/0080157 A1 | 3/2017 | Cabiri |
| 2017/0080158 A1 | 3/2017 | Cabiri |

(56) References Cited

U.S. PATENT DOCUMENTS

2017/0143896 A1     5/2017   Lorenzen et al.
2017/0281874 A1   10/2017   Helmer et al.
2017/0354782 A1   12/2017   Quinn et al.

FOREIGN PATENT DOCUMENTS

| | | |
|---|---|---|
| EP | 2438945 A1 | 11/2012 |
| EP | 2596823 A1 | 5/2013 |
| EP | 2823837 A1 | 1/2015 |
| JP | 2016509903 A | 4/2016 |
| WO | 2012032411 A2 | 3/2012 |
| WO | 2013155153 A1 | 10/2013 |
| WO | 2014159017 A1 | 10/2014 |
| WO | 2014179774 A1 | 11/2014 |
| WO | 2015081337 A2 | 6/2015 |
| WO | 2016075254 A1 | 5/2016 |
| WO | 2017055588 A1 | 4/2017 |
| WO | 2017214424 A2 | 12/2017 |
| WO | 2018007623 A1 | 1/2018 |

\* cited by examiner

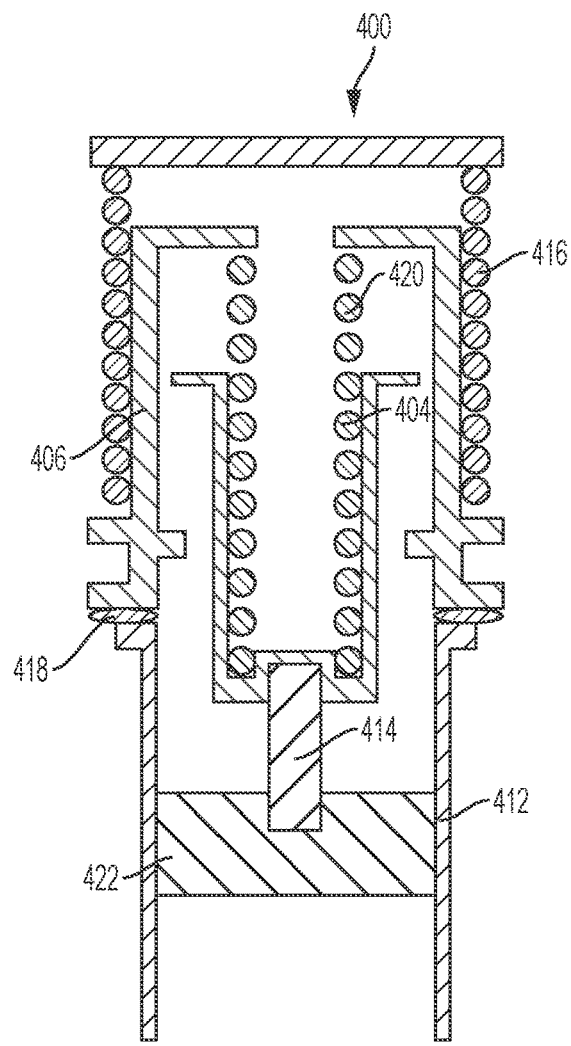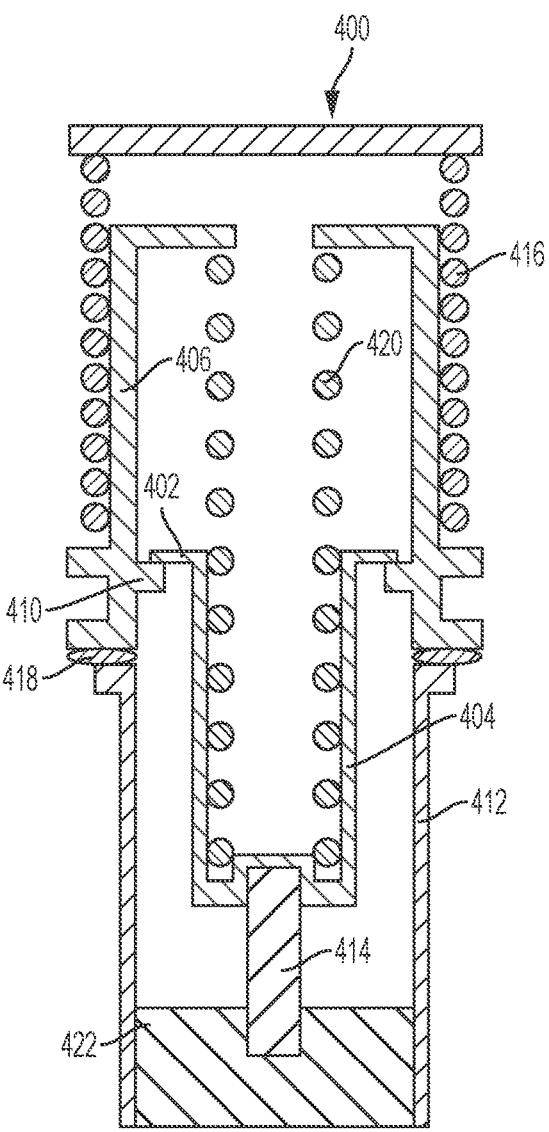
FIG. 84E
FIG. 84F

SPACER ASSEMBLY FOR DRUG DELIVERY DEVICE

CROSS-REFERENCE TO RELATED APPLICATION

The present application is a continuation of U.S. application Ser. No. 16/160,231, filed Oct. 15, 2018, entitled Spacer Assembly for Drug Delivery Device", which claims priority to U.S. Provisional Application Ser. No. 62/572,704, filed Oct. 16, 2017, entitled "Spacer Assembly for Drug Delivery Device", the entire disclosures of each of which are hereby incorporated by reference.

BACKGROUND OF THE INVENTION

Field of the Disclosure

The present disclosure relates generally to an injector device and method for delivering a fluid into the body of a patient by injection.

Description of the Related Art

Various types of automatic injection devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

SUMMARY OF THE INVENTION

The present invention is directed to a drive assembly for a drug delivery system comprising a plunger member configured to engage and move a stopper within a container, the plunger member having a first position and a second position axially spaced from the first position, a biasing member configured to move the plunger member from the first position to the second position, and an adjustable spacer assembly positioned between the plunger member and the stopper.

In one aspect, the spacer assembly may comprise a spacer element attached to the stopper and at least one shim.

In another aspect, the spacer assembly may comprise a spacer element and a holder to which the spacer element is attached. The holder may be attached to the stopper and the spacer element may be attached to the holder by a threaded engagement. The threaded engagement may allow rotation of the spacer element relative to the holder when a torque is applied to the spacer element to prohibit rotation of the spacer element relative to the holder when an axial force is applied to the spacer element. The threads provided on the spacer element may extend in a radially outward direction. The threads provided on the spacer element may be angled such that application of an axial force to the spacer element causes the threads to engage a sidewall of the holder.

When the spacer element is in a first position with respect to the holder, the spacer assembly has a first length in a longitudinal direction, and when the when the spacer element is in a second position with respect to the holder, the spacer assembly has a second length in the longitudinal direction, the first length being greater than the second length.

In another aspect, the spacer assembly may further comprise a flexible tab extending from the spacer element and a plurality of ratchet teeth on a surface of the spacer holder. The flexible tab engages the ratchet teeth and the engagement of the flexible tab with the ratchet teeth allows the spacer element to be rotated in a direction that threads the spacer element into the holder and prevents the spacer element from rotating in a direction that removes the spacer element from the holder.

In another aspect, the spacer element is in a first position with respect to the holder, the spacer assembly has a first length in a longitudinal direction, and when the when the spacer element is in a second position with respect to the holder, the spacer assembly has a second length in the longitudinal direction, the first length being greater than the second length.

In another aspect, the spacer element may comprise a first protrusion and the holder may comprise a second protrusion. When the spacer element is in the first position with respect to the holder, the first protrusion is in contact with the second protrusion and the spacer assembly has the first length in the longitudinal direction, and when the spacer element is in a second position with respect to the holder, the first protrusion is not in contact with the second protrusion and the spacer assembly has the second length in the longitudinal direction.

In another aspect, the spacer element may comprise an annular sidewall and the holder may comprise a sidewall and a central post. An exterior surface of the annular sidewall of the spacer element may be in threaded engagement with an interior surface of the sidewall of the holder and an interior surface of the sidewall of the spacer may be in threaded engagement with an exterior surface of the central post. When the central post is a first position, movement of the spacer element with respect to the holder is prohibited, and when the central post is axially extended to a second position, the spacer element is free to rotate with respect to the holder.

In another aspect, the spacer assembly may further comprise a locking pin and the spacer element may further comprise a recess for receiving the locking pin.

In another aspect, the spacer assembly may further comprise an expandable container positioned within the spacer element and the holder between an upper proximal portion of the spacer element and a lower bottom portion of the holder. Expansion or contraction of the expandable container may cause the spacer element to move relative to the holder.

In another aspect, the spacer assembly may comprise a spacer element fixed to the stopper and a plunger extension movably fixed to the plunger member. The plunger extension may be in threaded engagement with the plunger member.

The present invention is also directed to a drug delivery system for injecting a medicament, the system comprising a container configured to receive a medicament, the container comprising a stopper configured to move within the container and a closure, a drive assembly as described above, and a needle actuator assembly comprising a needle configured to be placed in fluid communication with the container.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 84E is a schematic view of the drive assembly of FIG. 84A according to one aspect of the present invention, showing the drive assembly in a use position.

FIG. 84F is a schematic view of the drive assembly of FIG. 84A according to one aspect of the present invention, showing the drive assembly in a post-use position.

FIG. 91 is a perspective view of a spacer assembly for a drug delivery system according to a further aspect of the present invention.

FIG. 92 is a perspective view of a spacer assembly for a drug delivery system according to another aspect of the present invention.

FIG. 93A is a cross-sectional view of the spacer assembly of FIG. 92 according to one aspect of the present invention, showing a pre-assembly position of the spacer assembly.

FIG. 93B is a cross-sectional view of the spacer assembly of FIG. 92 according to one aspect of the present invention, showing an assembled position of the spacer assembly.

FIG. 94 is a perspective view of a spacer assembly for a drug delivery system according to one aspect of the present invention.

FIG. 95 is a front view of the spacer assembly of FIG. 94 according to one aspect of the present invention.

FIG. 96 is a cross-sectional view of the spacer assembly of FIG. 94 according to one aspect of the present invention.

FIG. 97 is a perspective view of the spacer assembly of FIG. 94 according to one aspect of the present invention, showing a shim removed.

FIG. 98 is a perspective view of a fixed spacer of the spacer assembly of FIG. 94 according to one aspect of the present invention.

FIG. 99 is a perspective view of an adjustable spacer of the spacer assembly of FIG. 94 according to one aspect of the present invention.

FIG. 100 is a perspective view of a shim of the spacer assembly of FIG. 94 according to one aspect of the present invention.

FIG. 101 is a cross-sectional view of a spacer assembly having a single shim according to one aspect of the present invention.

Figure 101:
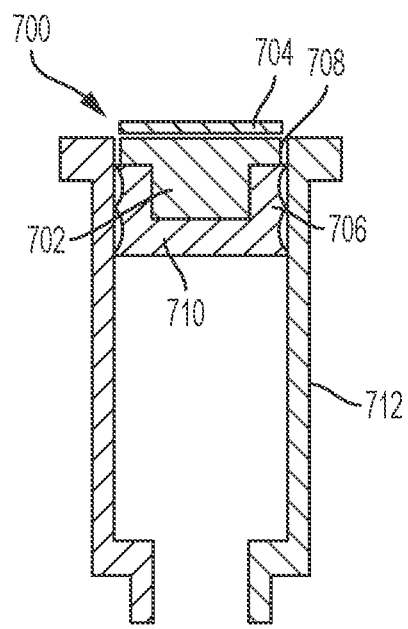
Figure 102:
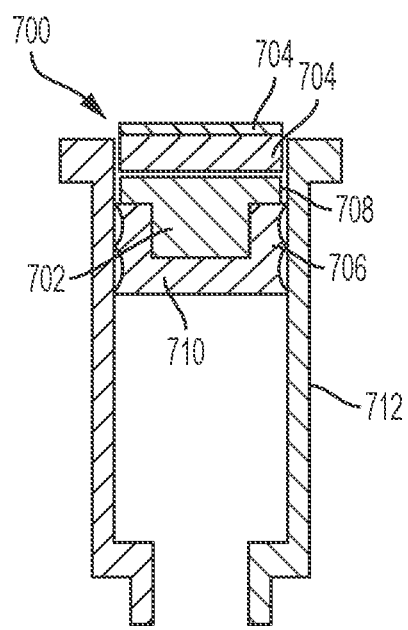

FIG. 102 is a cross-sectional view of the spacer assembly of FIG. 101 having multiple shims according to one aspect of the present invention.

Figure 103:
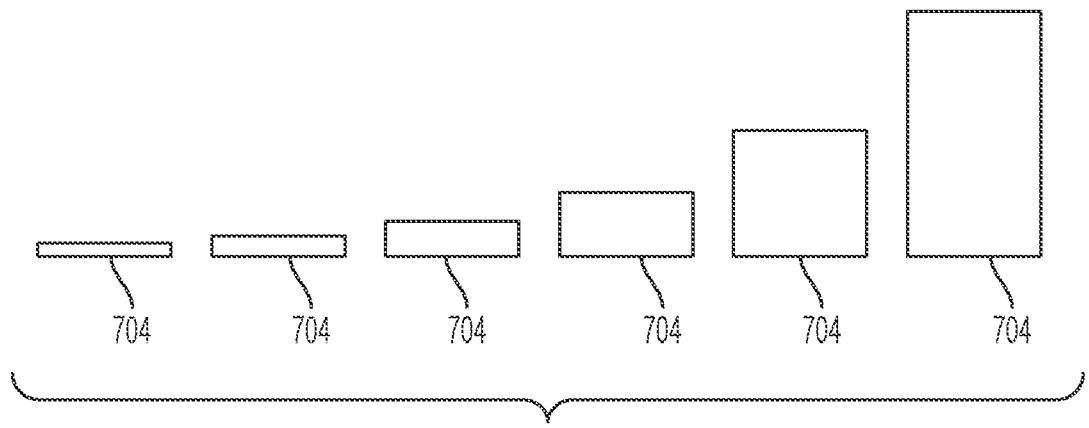

FIG. 103 is a cross-sectional view a set of shims for use with the spacer assembly of FIG. 101 according to one aspect of the present invention.

Figure 104:
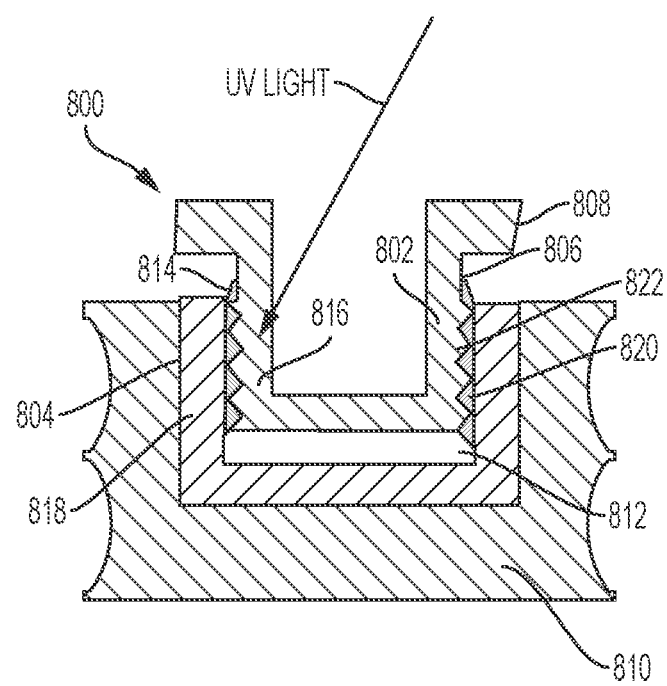

FIG. 104 is a cross-sectional view of a spacer assembly according to one aspect of the present invention.

Figure 105:
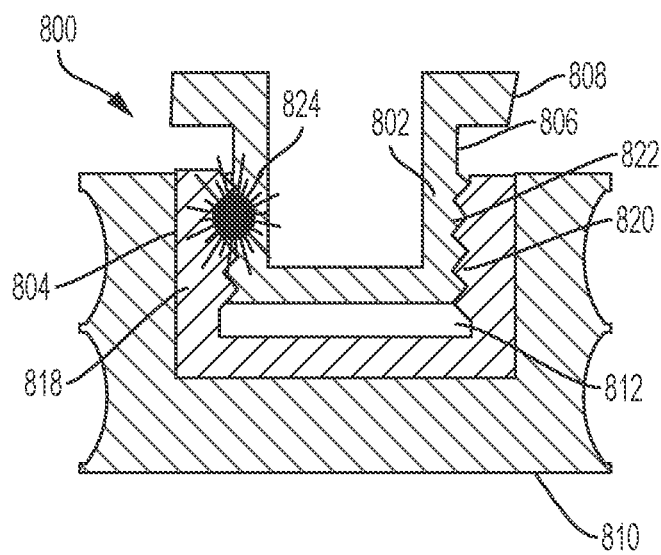

FIG. 105 is a cross-sectional view of a spacer assembly according to one aspect of the present invention.

Figure 106:
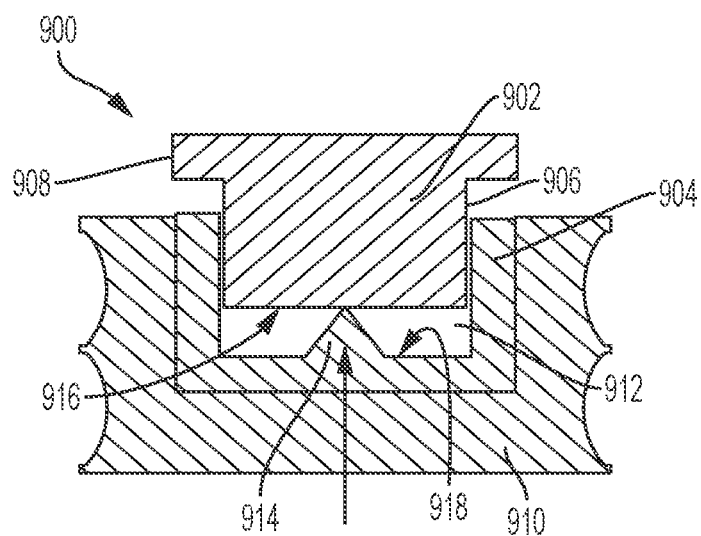

FIG. 106 is a cross-sectional view of a spacer assembly according to one aspect of the present invention.

Figure 107:
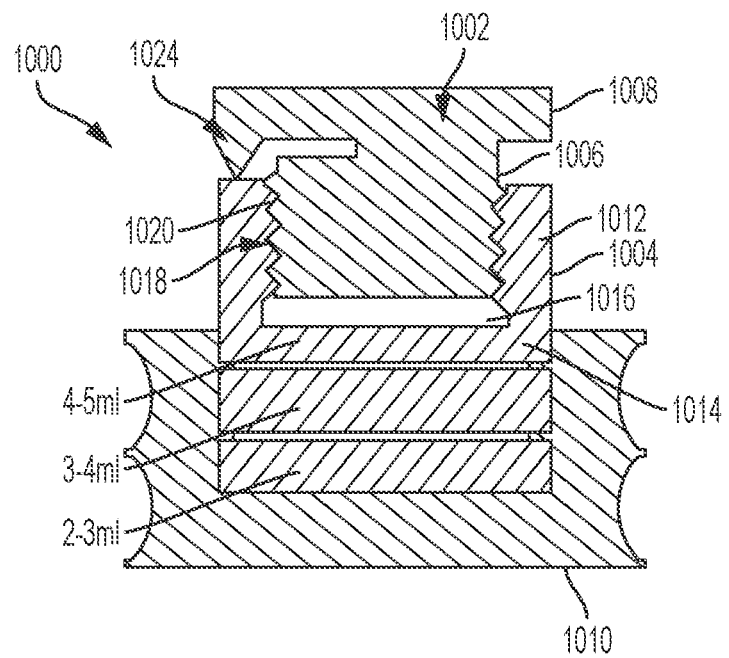

FIG. 107 is a cross-sectional view of a spacer assembly according to one aspect of the present invention.

Figure 108:
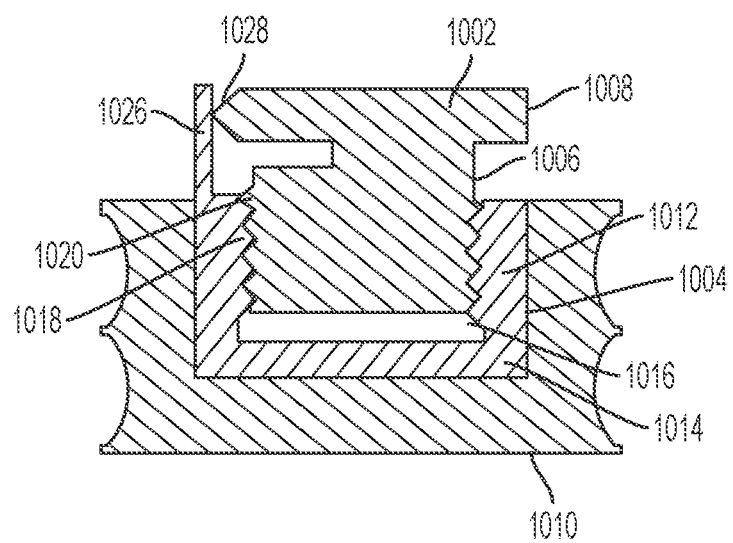

FIG. 108 is a cross-sectional view of a spacer assembly according to one aspect of the present invention.

Figure 109:
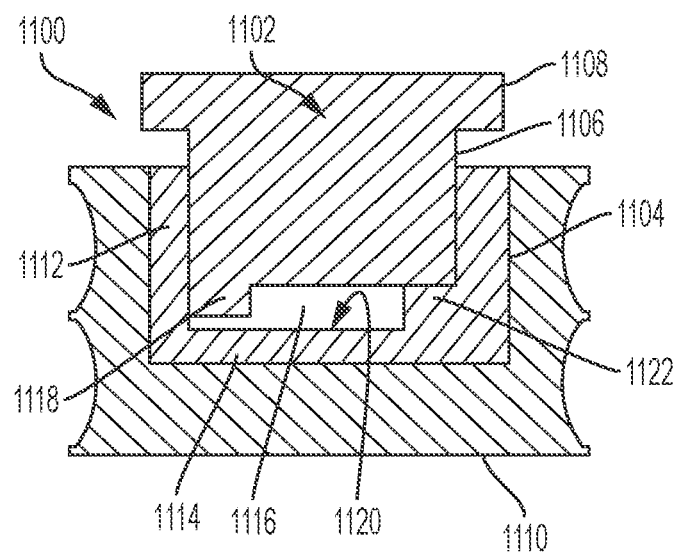

FIG. 109 is a cross-sectional view of a spacer assembly shown in a first position according to one aspect of the present invention.

Figure 110:
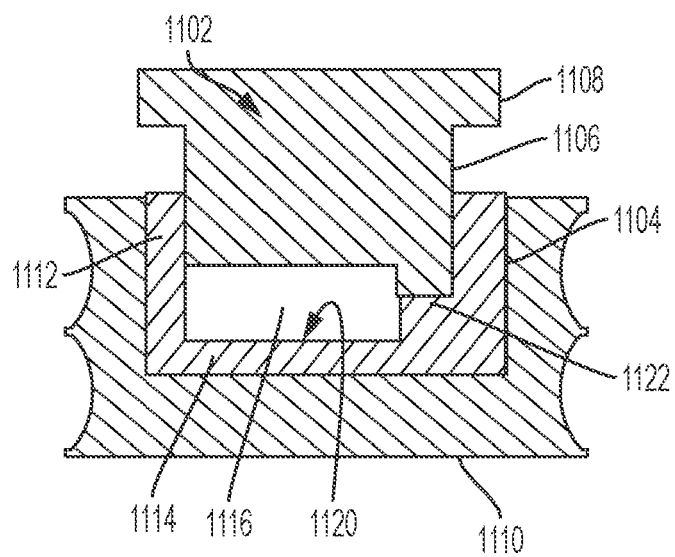

FIG. 110 is a cross-sectional view of the spacer assembly of FIG. 109 shown in a second position according to one aspect of the present invention.

Figure 111:
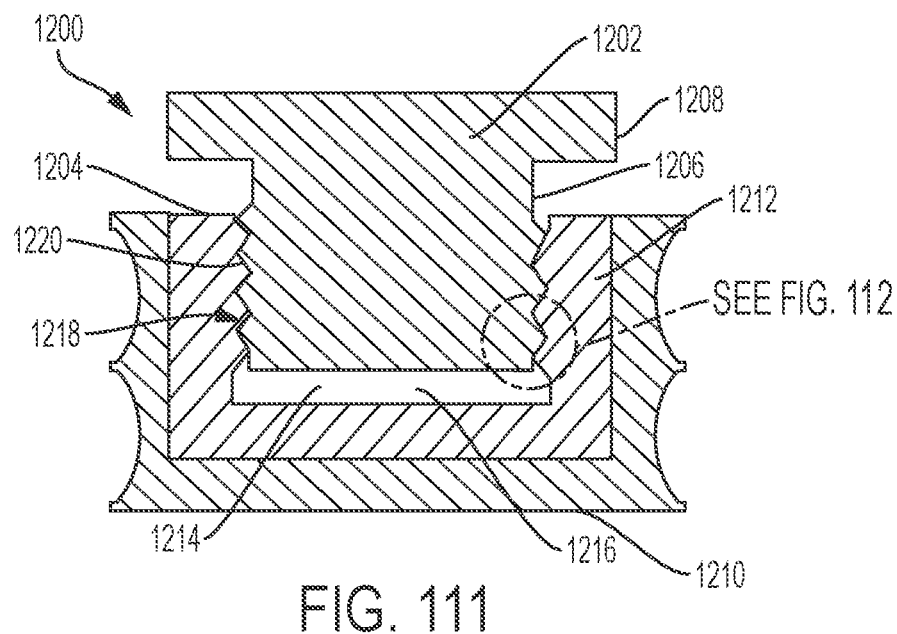

FIG. 111 is a cross-sectional view of a spacer assembly according to one aspect of the present invention.

Figure 112:
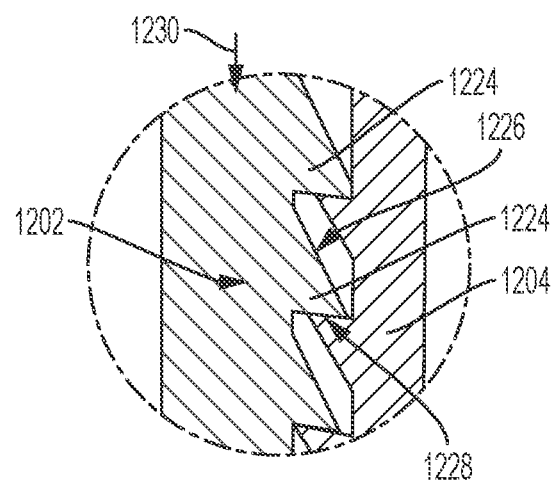

FIG. 112 is a magnified cross-sectional view of the indicated portion of the spacer assembly of FIG. 111 according to one aspect of the present invention.

Figure 113:
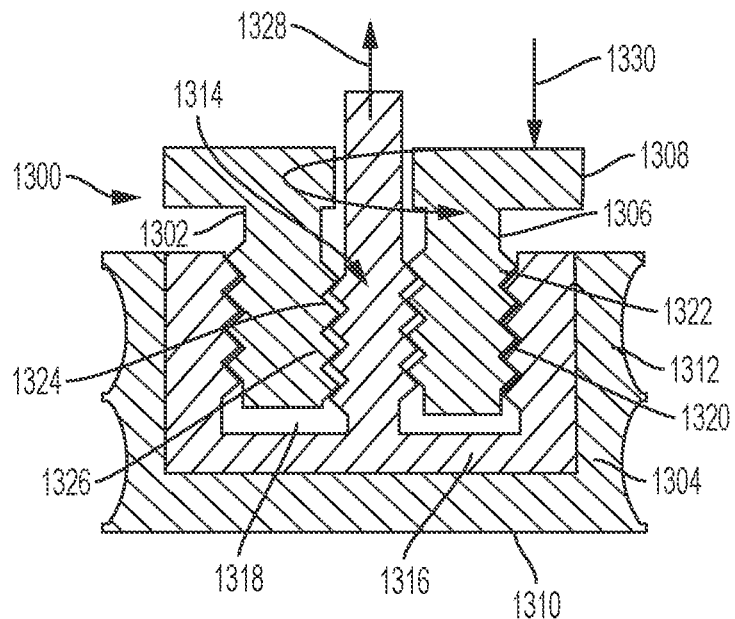

FIG. 113 is a cross-sectional view of a spacer assembly shown in a first position according to one aspect of the present invention.

Figure 114:
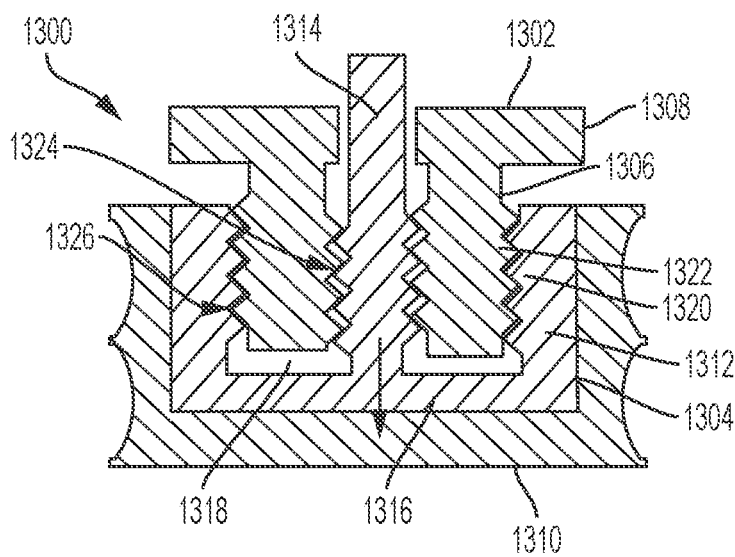

FIG. 114 is a cross-sectional view of the spacer assembly of FIG. 113 shown in a second position according to one aspect of the present invention.

FIG. 115A is a cross-sectional view of a first step in the assembly of the spacer assembly of FIG. 113 according to one aspect of the present invention.

FIG. 115B is a cross-sectional view of a second step in the assembly of the spacer assembly of FIG. 113 according to one aspect of the present invention.

FIG. 115C is a cross-sectional view of a first step in the assembly of the spacer assembly of FIG. 113 according to one aspect of the present invention.

Figure 116:
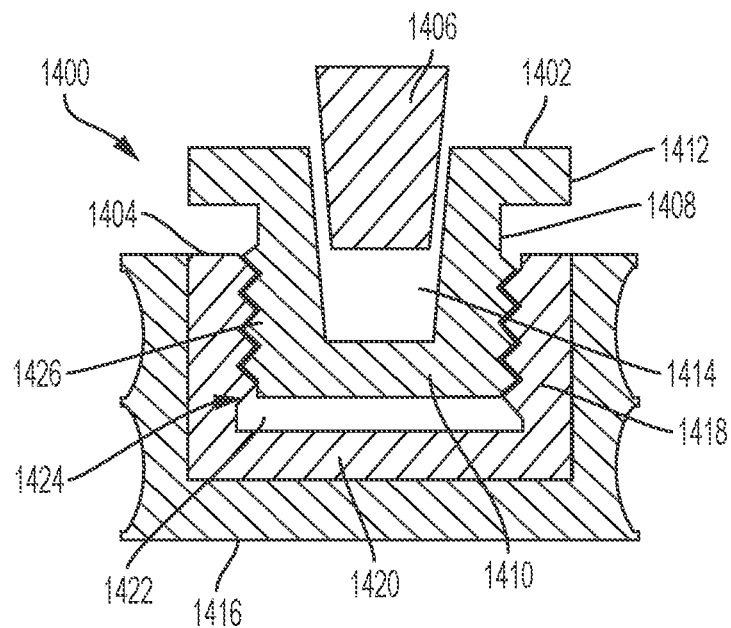

FIG. 116 is a cross-sectional view of a spacer assembly before the insertion of the locking pin according to one aspect of the present invention.

Figure 117:
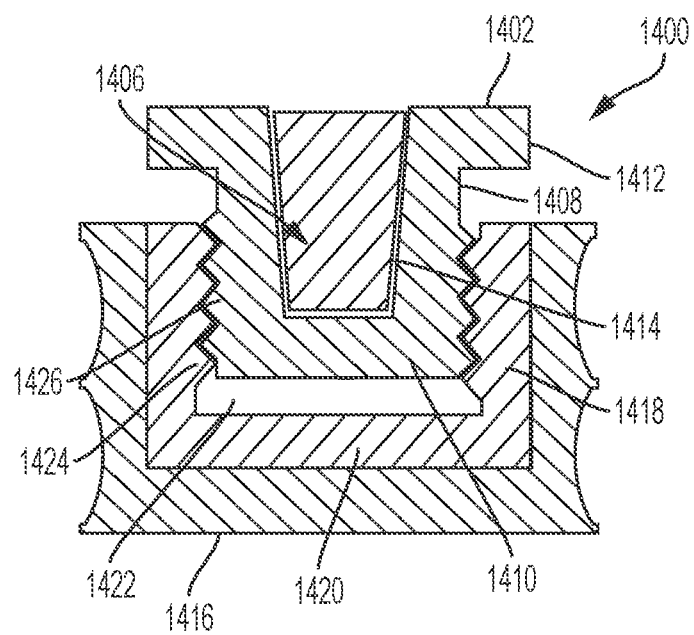

FIG. 117 is a cross-sectional view of a spacer assembly of FIG. 116 after the insertion of the locking pin according to one aspect of the present invention.

Figure 118:
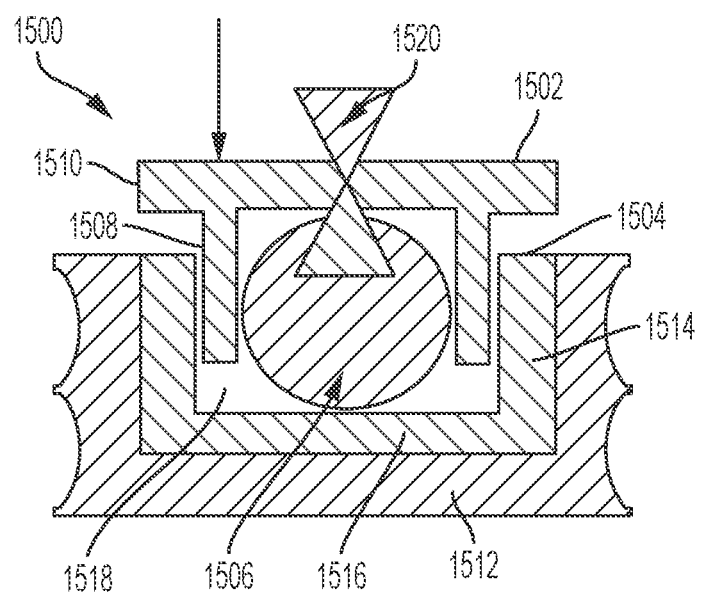

FIG. 118 is a cross-sectional view of a spacer assembly according to one aspect of the present invention.

Figure 119:
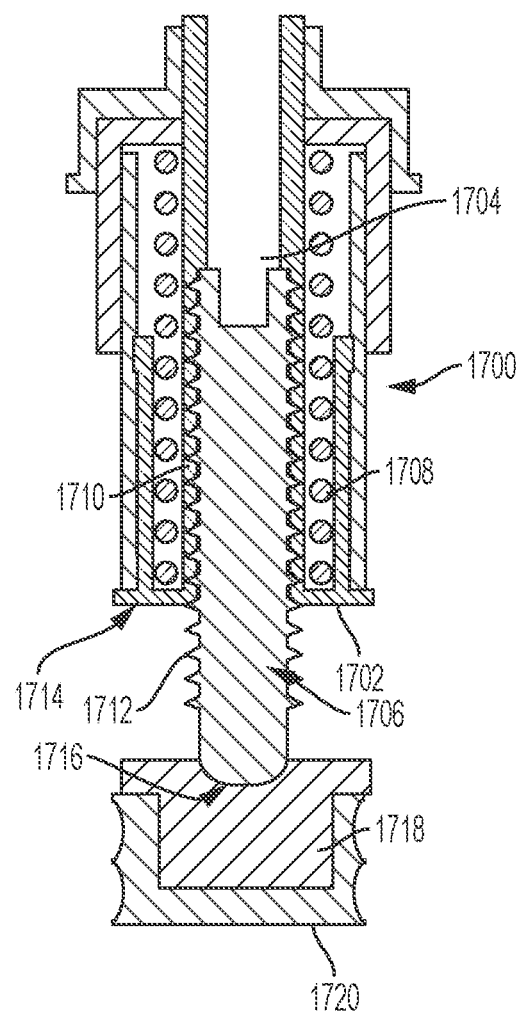

FIG. 119 is a cross-sectional view of an adjustable plunger assembly according to one aspect of the present invention.

The exemplifications set out herein illustrate exemplary aspects of the disclosure, and such exemplifications are not to be construed as limiting the scope of the disclosure in any manner.

DETAILED DESCRIPTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 17:
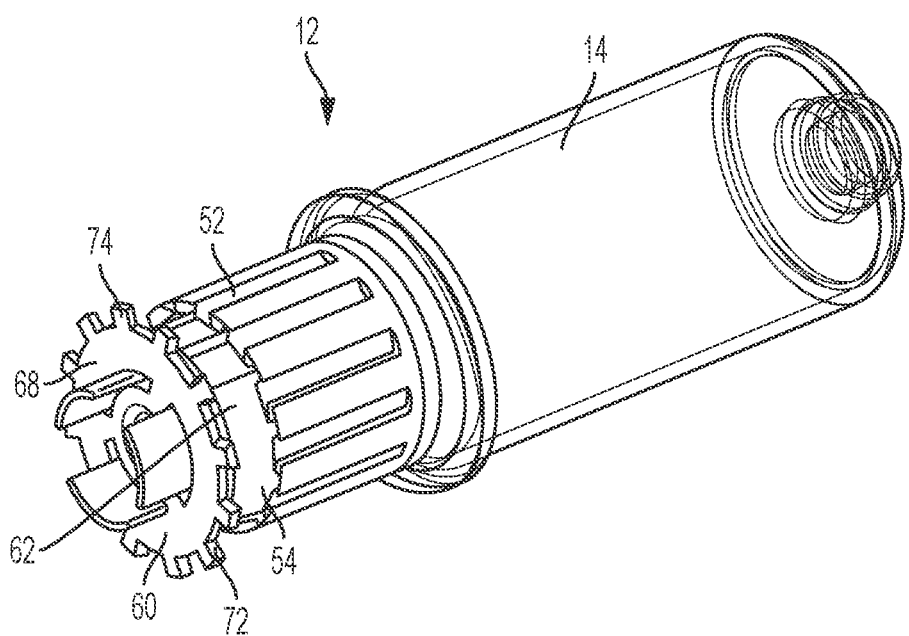
FIG. 17 is a perspective view of a drive assembly for a drug delivery system according to one aspect of the present invention.

Referring to FIGS. 1-16, a drug delivery system 10 according to one aspect of the present invention includes a drive assembly 12, a container 14, a valve assembly 16, and a needle actuator assembly 18. The drive assembly 12, the container 14, the valve assembly 16, and the needle actuator assembly 18 are at least partially positioned within a housing 20. The housing 20 includes a top portion 22 and a bottom portion 24, although other suitable arrangements for the housing 20 may be utilized. In one aspect, the drug delivery system 10 is an injector device configured to be worn or secured to a user and to deliver a predetermined dose of a medicament provided within the container 14 via injection into the user. The system 10 may be utilized to deliver a "bolus injection" where a medicament is delivered within a set time period. The medicament may be delivered over a time period of up to 45 minutes, although other suitable injection amounts and durations may be utilized. A bolus administration or delivery can be carried out with rate controlling or have no specific rate controlling. The system 10 may deliver the medicament at a fixed pressure to the user with the rate being variable. The general operation of the system 10 is described below in reference to FIGS. 1-16 with the specifics of the drive assembly 12, needle actuator assembly 18, and other features of the system 10, discussed below in connection with FIGS. 17-93.

Referring again to FIGS. 1-16, the system 10 is configured to operate through the engagement of an actuation button 26 by a user, which results in a needle 28 of the needle assembly 18 piercing the skin of a user, the actuation of the drive assembly 12 to place the needle 28 in fluid communication with the container 14 and to expel fluid or medicament from the container 14, and the withdrawal of the needle 28 after injection of the medicament is complete. The general operation of a drug delivery system is shown and described in International Publication Nos. 2013/155153 and 2014/179774, which are hereby incorporated by reference in their entirety. The housing 20 of the system 10 includes an indicator window 30 for viewing an indicator arrangement 32 configured to provide an indication to a user on the status of the system 10 and a container window 31 for viewing the container 14. The indicator window 30 may be a magnifying lens for providing a clear view of the indicator arrangement 32. The indicator arrangement 32 moves along with the needle actuator assembly 18 during use of the system 10 to indicate a pre-use status, use status, and post-use status of the system 10. The indicator arrangement 32 provides visual indicia regarding the status, although other suitable indicia, such an auditory or tactile, may be provided as an alternative or additional indicia.

Figure 1:
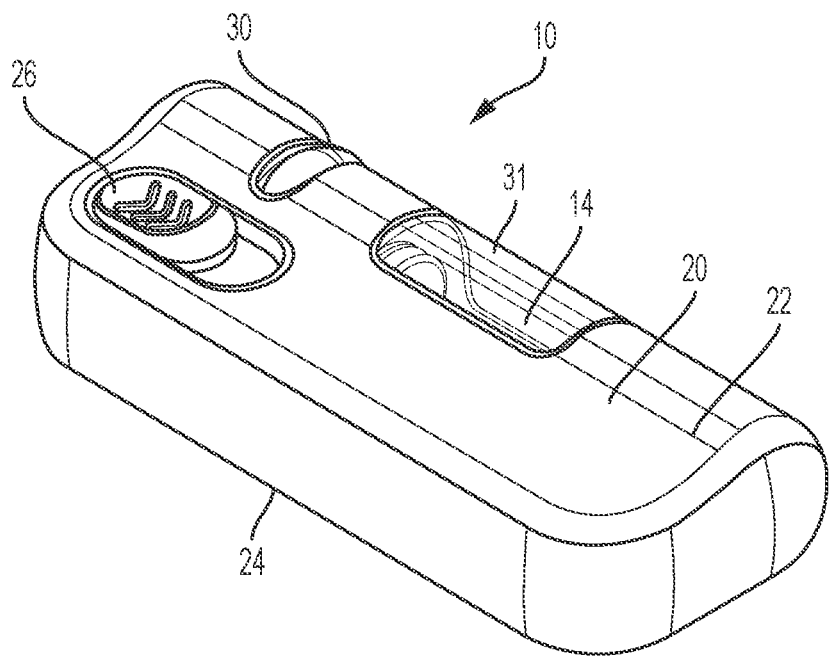
FIG. 1 is a perspective view of a drug delivery system according to one aspect of the present invention.
Figure 2:
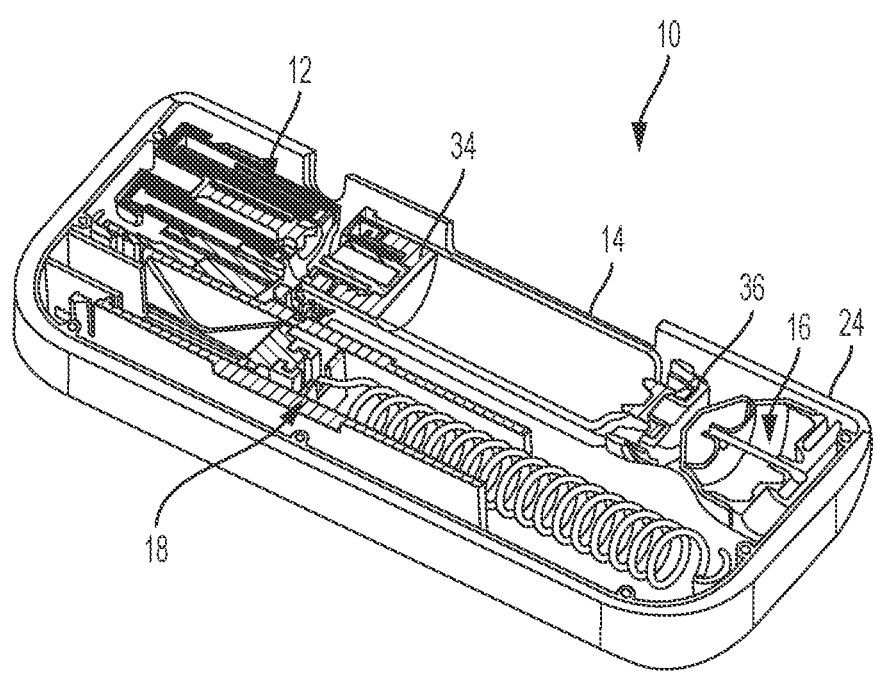
FIG. 2 is a perspective, cross-sectional view of the drug delivery system of FIG. 1 according to one aspect of the present invention.
Figure 3:
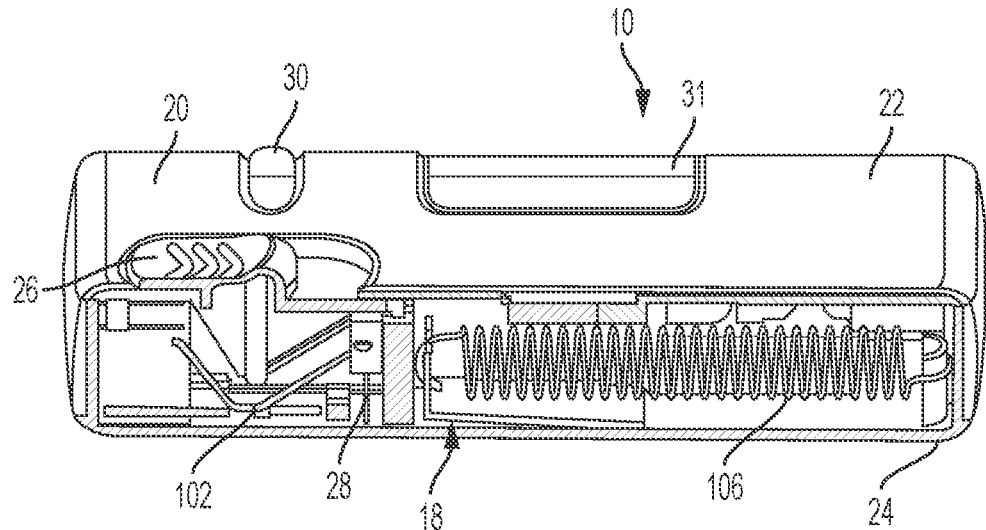
FIG. 3 is a front perspective, cross-sectional view of the drug delivery system of FIG. 1 according to one aspect of the present invention.
Figure 4:
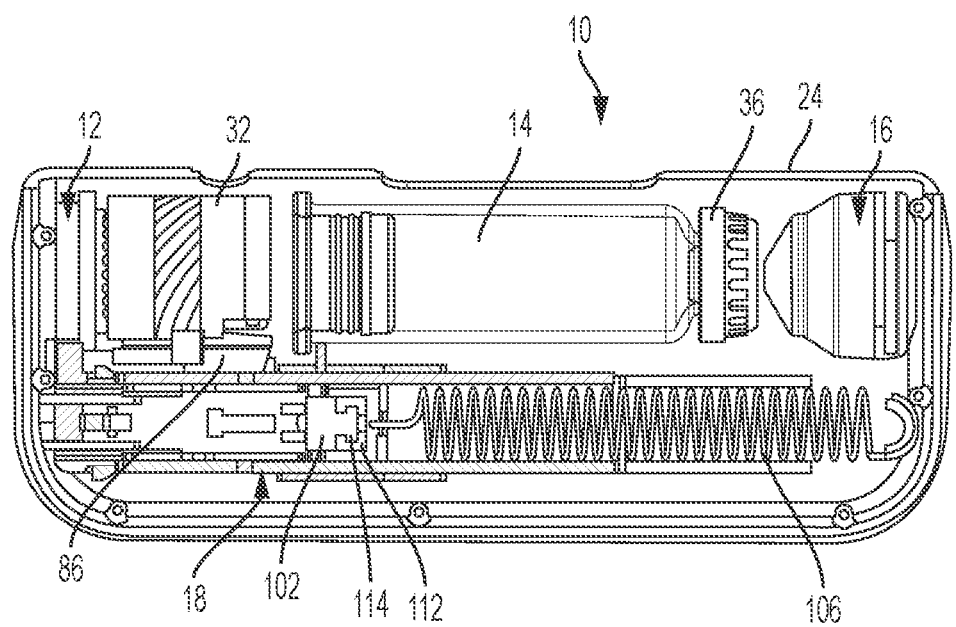
FIG. 4 is a top view of the drug delivery system of FIG. 1 according to one aspect of the present invention, showing a top portion of the housing removed and the drug delivery system in a pre-use position.
Figure 5:
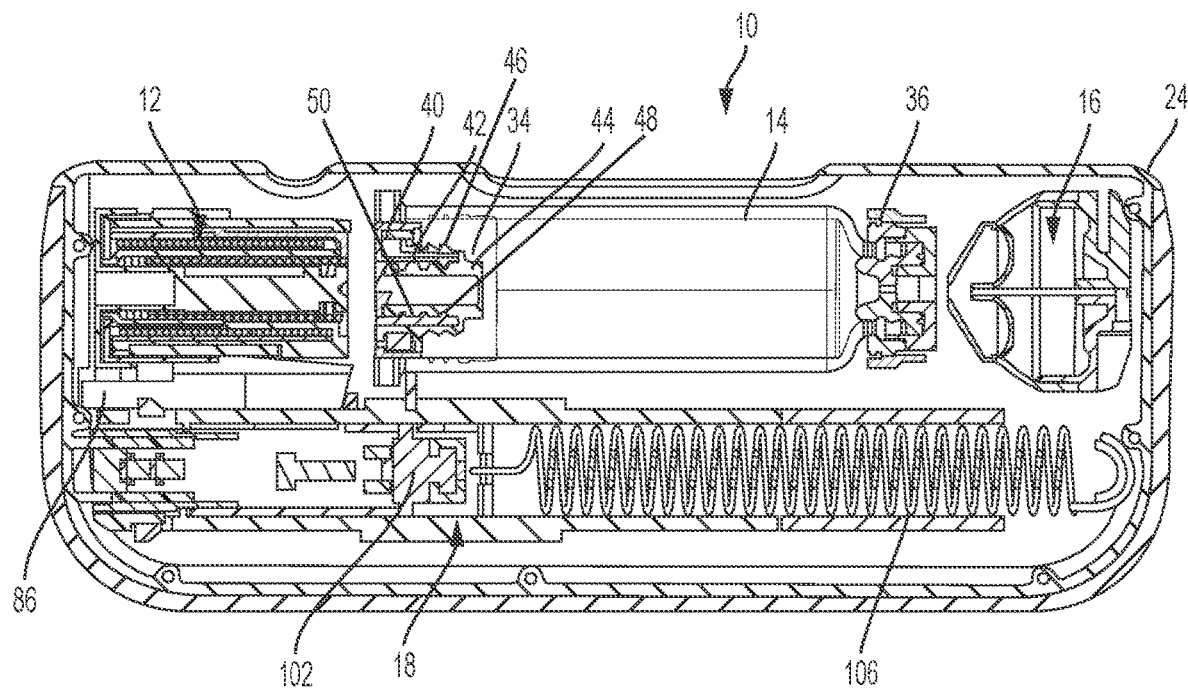
FIG. 5 is a top, cross-sectional view of the drug delivery system of FIG. 1 according to one aspect of the present invention, showing the drug delivery system in a pre-use position.
Figure 6:
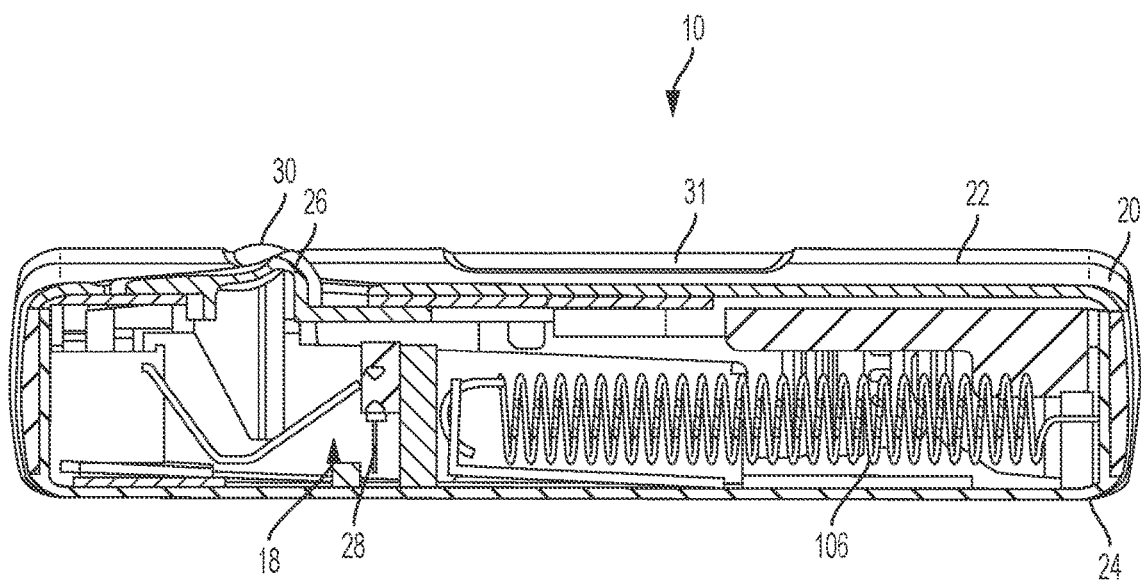
FIG. 6 is a front, cross-sectional view of the drug delivery system of FIG. 1 according to one aspect of the present invention, showing the drug delivery system in a pre-use position.
Figure 7:
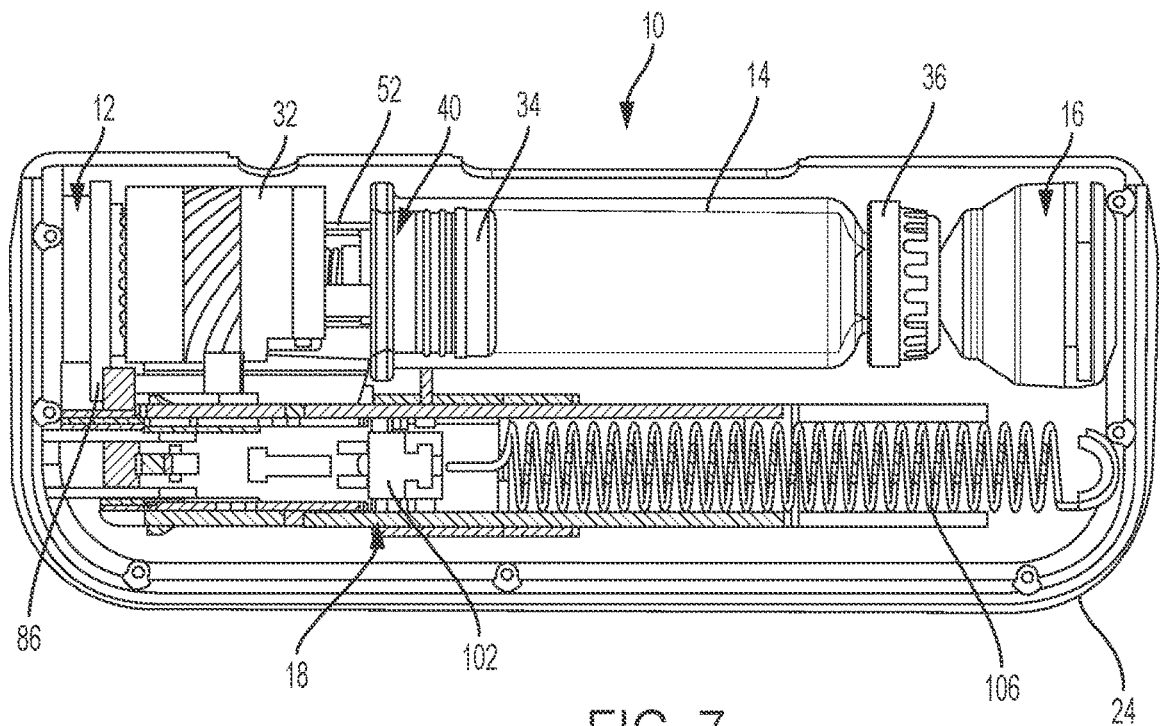
FIG. 7 is a top view of the drug delivery system of FIG. 1 according to one aspect of the present invention, showing a top portion of the housing removed and the drug delivery system in an initial actuation position.
Figure 8:
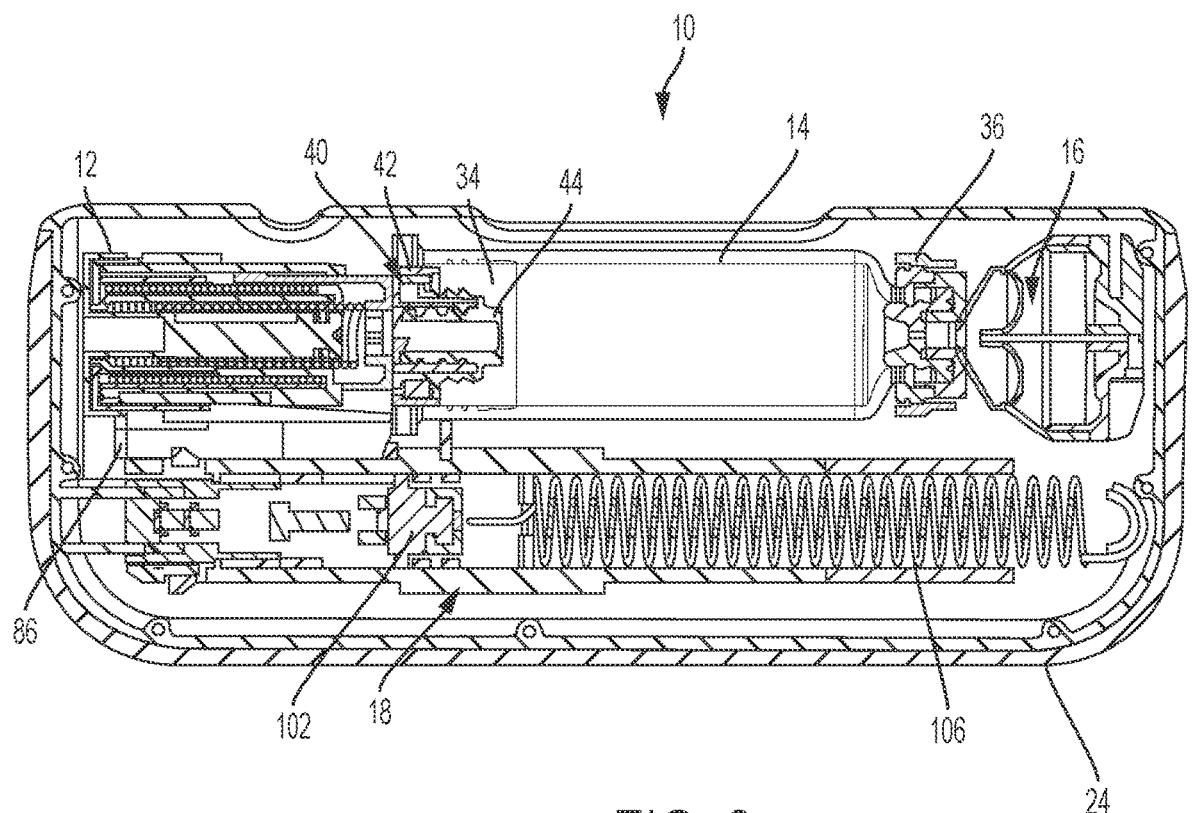
FIG. 8 is a top, cross-sectional view of the drug delivery system of FIG. 1 according to one aspect of the present invention, showing the drug delivery system in an initial actuation position.
Figure 9:
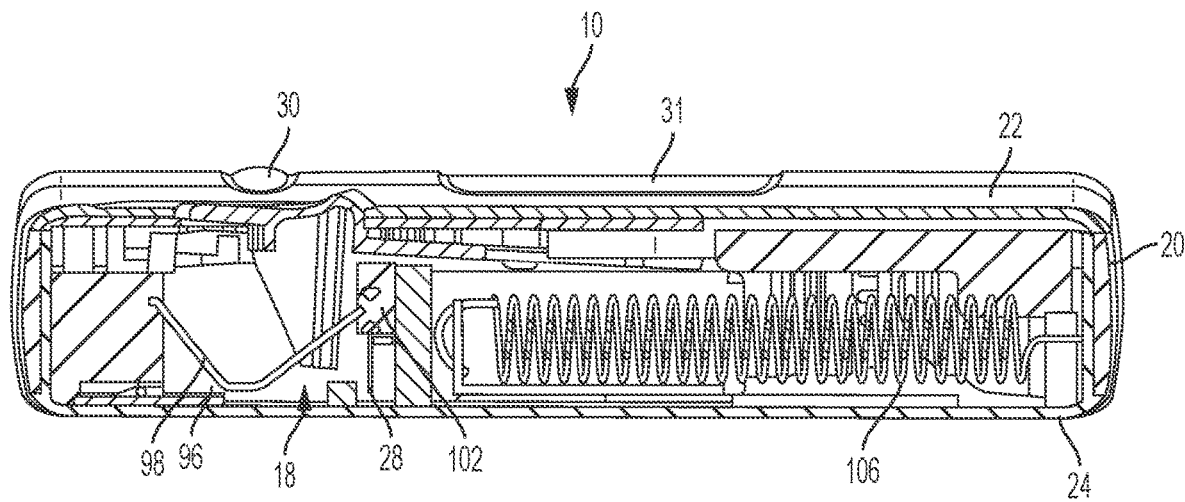
FIG. 9 is a front, cross-sectional view of the drug delivery system of FIG. 1 according to one aspect of the present invention, showing the drug delivery system in an initial actuation position.

Referring to FIGS. 4-6, during a pre-use position of the system 10, the container 14 is spaced from the drive assembly 12 and the valve assembly 16 and the needle 28 is in a retracted position. During the initial actuation of the system 10, as shown in FIGS. 7-9, the drive assembly 12 engages the container 14 to move the container 14 toward the valve assembly 16, which is configured to pierce a closure 36 of the container 14 and place the medicament within the container 14 in fluid communication with the needle 28 via a tube (not shown) or other suitable arrangement. The drive assembly 12 is configured to engage a stopper 34 of the container 14, which will initially move the entire container 14 into engagement with the valve assembly 16 due to the incompressibility of the fluid or medicament within the container 14. The initial actuation of the system 10 is caused by engagement of the actuation button 26 by a user, which releases the needle actuator assembly 18 and the drive assembly 12 as discussed below in more detail. During the initial actuation, the needle 28 is still in the retracted position and about to move to the extended position to inject the user of the system 10.

Figure 10:
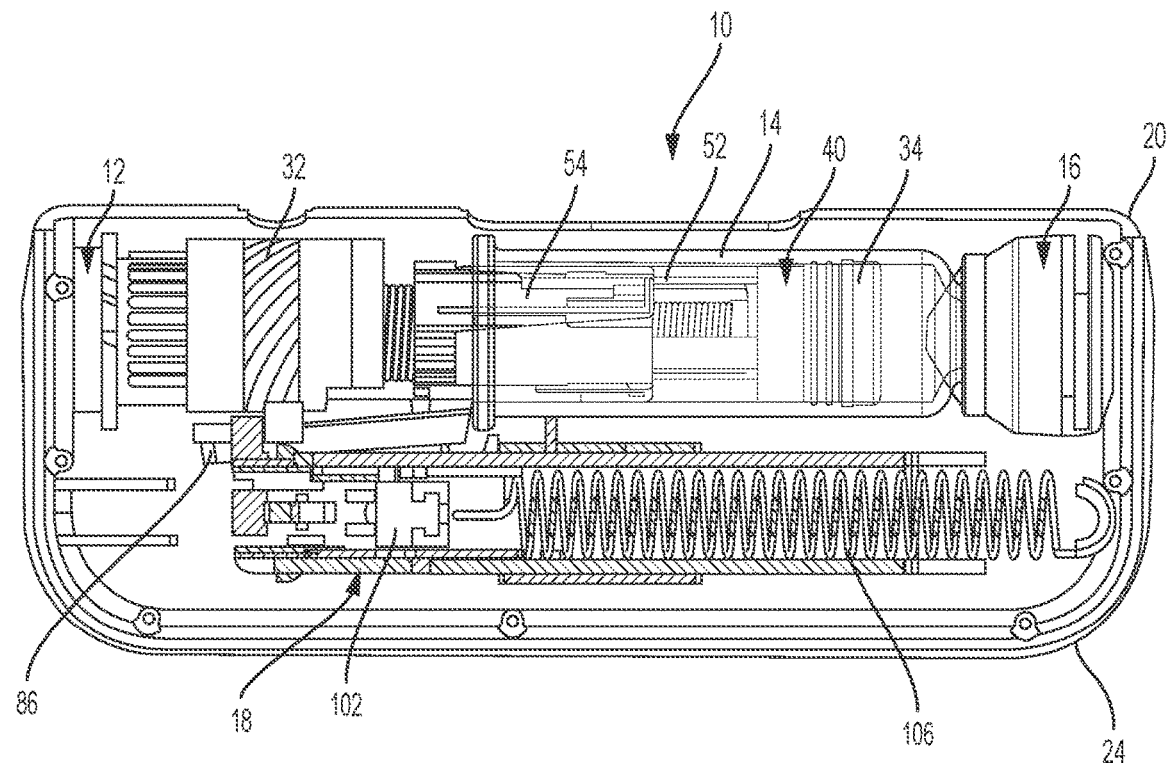
FIG. 10 is a top view of the drug delivery system of FIG. 1 according to one aspect of the present invention, showing a top portion of the housing removed and the drug delivery system in a use position.
Figure 11:
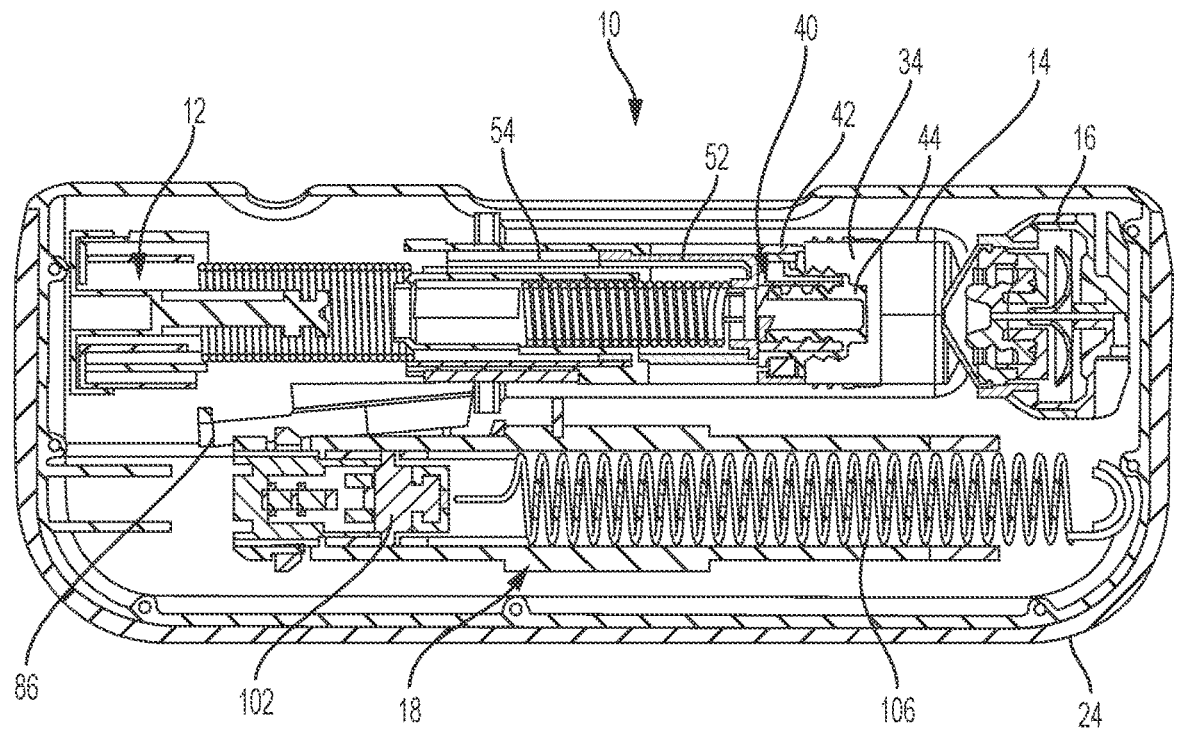
FIG. 11 is a top, cross-sectional view of the drug delivery system of FIG. 1 according to one aspect of the present invention, showing the drug delivery system in a use position.
Figure 12:
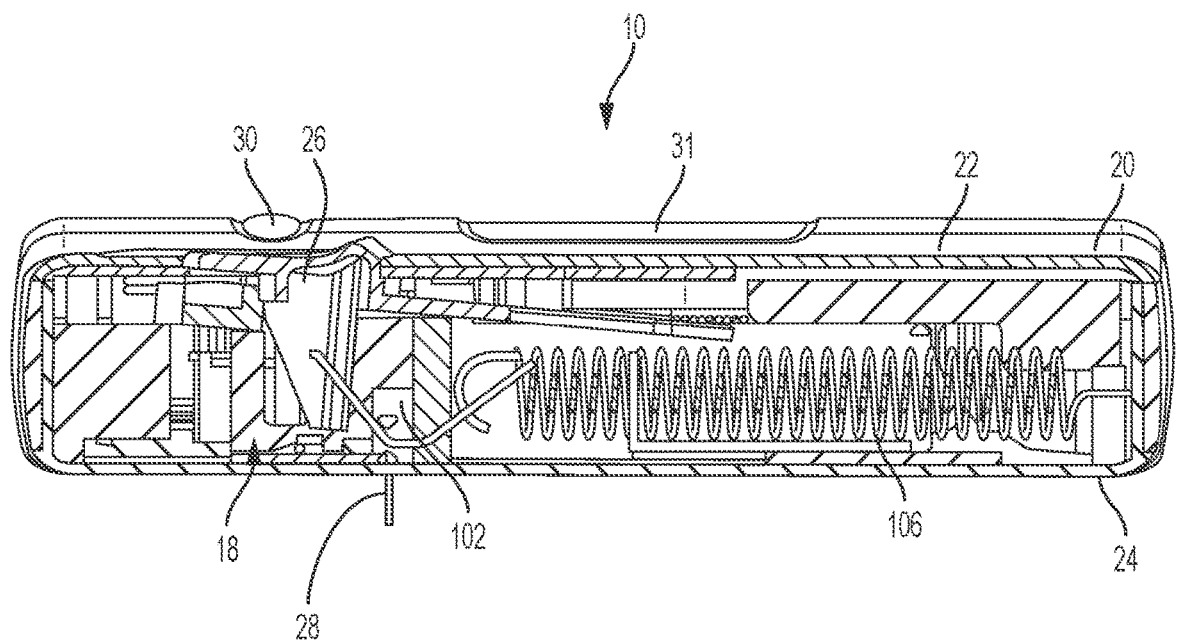
FIG. 12 is a front, cross-sectional view of the drug delivery system of FIG. 1 according to one aspect of the present invention, showing the drug delivery system in a use position.

In the use position of the system 10, as shown in FIGS. 10-12, the needle 28 is in the extended position at least partially outside of the housing 20 with the drive assembly 12 moving the stopper 34 within the container 14 to deliver the medicament from the container 14, through the needle 28, and to the user. In the use position, the valve assembly 16 has already pierced a closure 36 of the container 14 to place the container 14 in fluid communication with the needle 28, which also allows the drive assembly 12 to move the stopper 34 relative to the container 14 since fluid is able to be dispensed from the container 14. At the post-use position of the system 10, shown in FIGS. 13-15A, the needle 28 is in the retracted position and engaged with a pad 38 to seal the needle 28 and prevent any residual flow of fluid or medicament from the container 14. The container 14 and valve assembly 16 may be the container 14 and valve assembly 16 shown and described in International Publication No. WO 2015/081337, which is hereby incorporated by reference in its entirety.

Figure 15A:
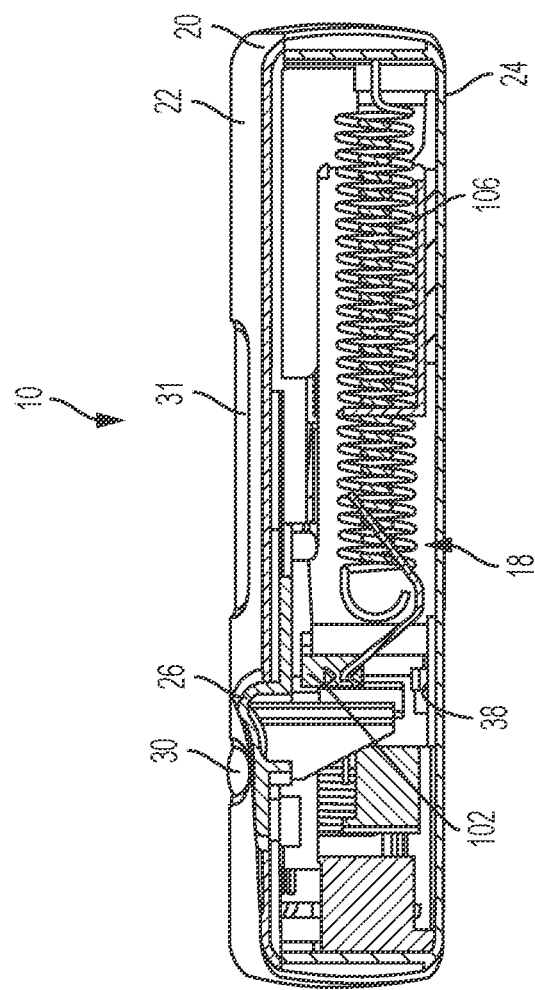
FIG. 15A is a front, cross-sectional view of the drug delivery system of FIG. 1 according to one aspect of the present invention, showing the drug delivery system in a post-use position.
Figure 15B:
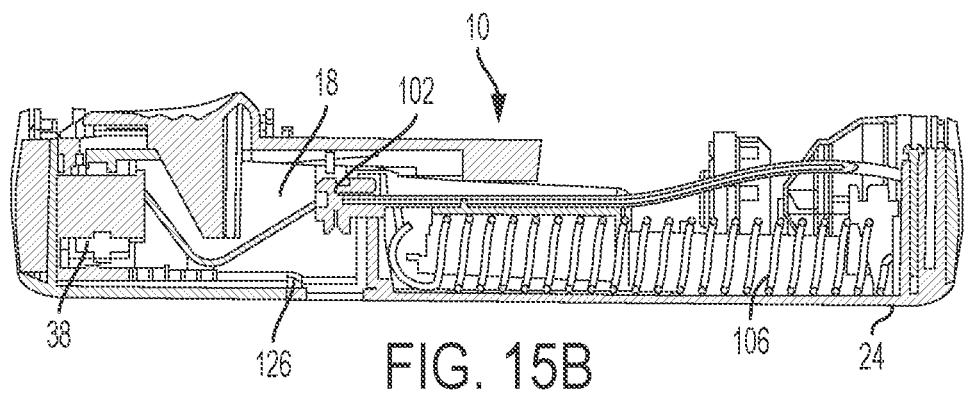
FIG. 15B is a front, cross-sectional view of the drug delivery system of FIG. 1 according to one aspect of the present invention, showing a pad with the drug delivery system in a pre-use position.
Figure 15C:
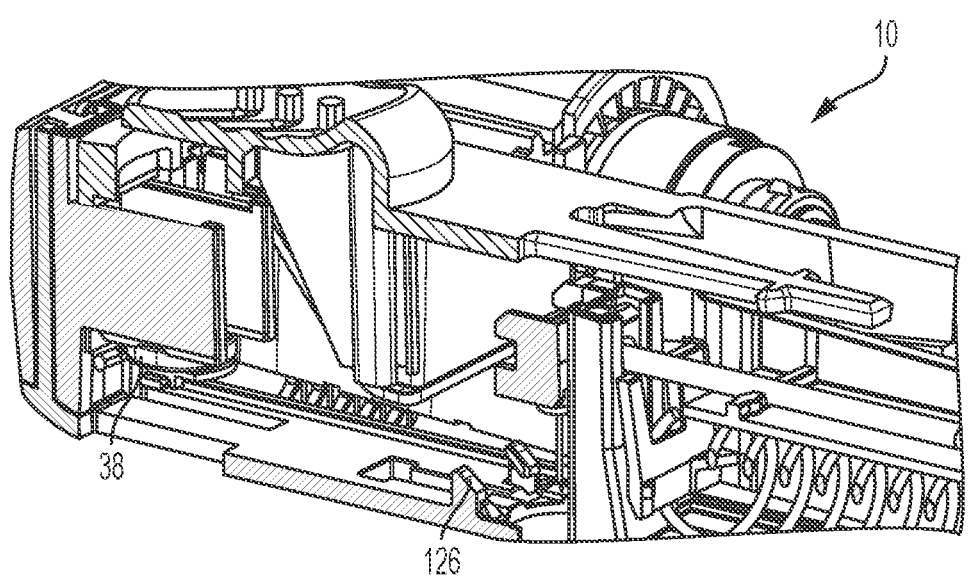
FIG. 15C is a perspective, cross-sectional view of the drug delivery system of FIG. 1 according to one aspect of the present invention, showing a pad with the drug delivery system in a pre-use position.
Figure 15D:
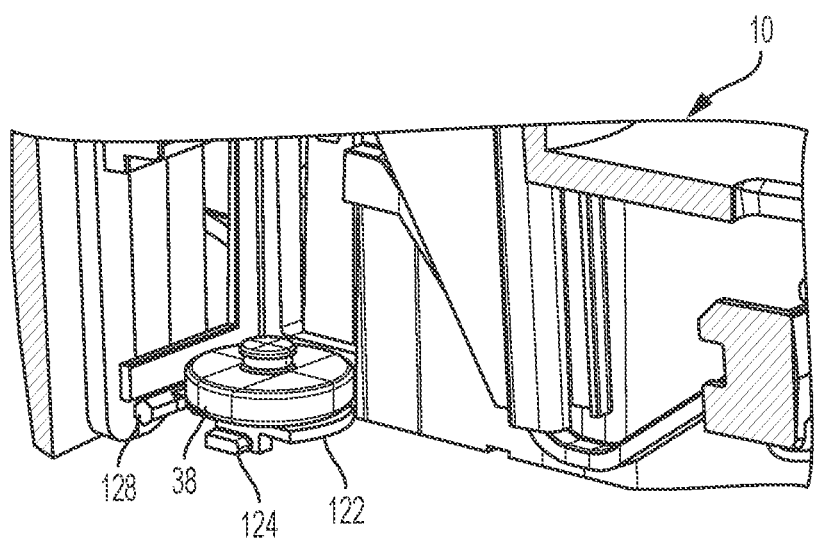
FIG. 15D is a perspective, cross-sectional view of the drug delivery system of FIG. 1 according to one aspect of the present invention, showing a pad with the drug delivery system in a pre-use position.
Figure 16:
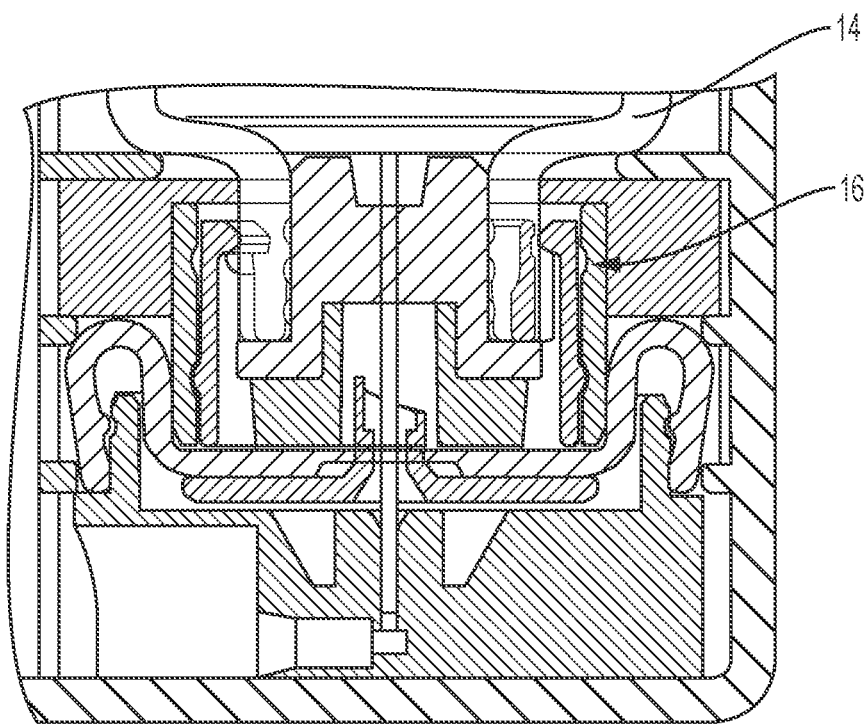
FIG. 16 is a partial cross-sectional view of the drug delivery system of FIG. 1 according to one aspect of the present invention, showing a valve assembly.

Referring to FIGS. 15A-15C, the pad 38 is biased into the pad as the needle actuator body 96 moves from the use position to the post-use position. In particular, the pad 38 is received by a pad arm 122 having a cam surface 124 that cooperates with a cam track 126 on the bottom portion 24 of the housing 20. The pad arm 122 is connected to the needle actuator body 96 via a torsion bar 128. The cam surface 124 is configured to engage the cam track 126 to deflect the pad arm 122 downwards thereby allowing the pad 38 to pass beneath the needle 28 before being biased upwards into the needle 28. The torsion bar 128 allows the pad arm 122 to twist about a pivot of the needle actuator body 96. The pad 38 may be press-fit into an opening of the pad arm 122, although other suitable arrangements for securing the pad 38 may be utilized.

Referring to FIGS. 1-33, the drive assembly 12 according to one aspect of the present invention is shown. As discussed above, the drive assembly 12 is configured to move the container 14 to pierce the closure 36 of the container 14 and also to move the stopper 34 within the container 14 to dispense fluid or medicament from the container 14.

For manufacturing purposes, using one size for a medicament container 14 is often desirable, even if multiple fill volumes or dosages are contemplated for use with the container 14. In such cases, when medicament containers are filled, the differing fill volumes result in different positions of the stopper 34. To accommodate such different stopper 34 positions, as well as accommodate manufacturing differences of the stoppers 34, aspects of the present invention include a bespoke or custom spacer or spacer assembly 40 disposed in a proximal end of the container 14, proximal to the stopper 34. The custom spacer or spacer assembly 40 is selected from a plurality of different size spacers or spacer assemblies 40 to occupy space from a proximal end of the stopper 34 to a proximal end of the container 14. In other words, the custom spacer or spacer assembly 40 provides an option that allows dispensing of a range of manufacturer-set pre-defined fill volumes by selection of different spacers or spacer assemblies 40, and reduces or eliminates the need for assembly configuration operations. The size of the custom spacer or spacer assembly 40 can be employed to account for under-filled volumes of the container 14, and provide a consistent bearing surface at the proximal end of the container 14.

The drive assembly 12 shown in FIGS. 17-33 is configured to engage and cooperate with a spacer assembly 40 received by the stopper 34 of the container 14. The spacer assembly 40 includes a spacer 42 and a spacer holder 44.

The spacer holder 44 is received by the stopper 34 and the spacer 42 is received by the spacer holder 44. The spacer holder 44 includes a first threaded portion 46 that engages a corresponding threaded portion of the stopper 34, although other suitable arrangements may be utilized. The spacer 42 also includes a threaded portion 48 that engages a corresponding second threaded portion 50 of the spacer holder 44 for securing the spacer 42 to the spacer holder 44, although other suitable arrangements may be utilized. The drive assembly 12 is configured to dispense a range of predetermined fill volumes of the container 14 while maintaining the functional features of the system 10 described above, including, but not limited to, retraction of the needle 28 after the end of the dose and providing an indication of the status of the system 10 while also minimizing abrupt engagement of the stopper 34 by the drive assembly 12. A discussed above, the drive assembly 12 is configured to dispense a plurality of discrete fill volume ranges by utilizing a plurality of sizes of the spacers 42. In one aspect, twelve fill volume ranges and twelve spacer 42 sizes are provided.

Referring to FIGS. 17-26, the drive assembly 12 includes a first plunger member 52, a second plunger member 54 received by the first plunger member 52, a first biasing member 56, a second biasing member 58, a plunger actuation member 60, and an index member 62. The first plunger member 52 is moveable from a pre-use position (shown in FIG. 18), to a use position (shown in FIG. 19), to a post-use position (shown in FIG. 20) with the first plunger member 52 configured to engage the spacer assembly 40 and move the stopper 34 within the container 14 to dispense medicament from the container 14. The first plunger member 52 is configured to move axially. The second plunger member 54 and the first plunger member 52 form a telescoping arrangement with the second plunger 54 configured to move axially after the first plunger member 52 moves a predetermined axial distance. The movement of the first and second plunger members 52, 54 is provided by the first and second biasing members 56, 58, which are compression springs, although other suitable arrangements for the biasing members 56, 58 may be utilized.

The first biasing member 56 is received by the second plunger member 54 and is constrained between the plunger actuation member 60 (and index member 62) and a first spring seat 64 of the second plunger member 54. The second biasing member 58 is positioned radially inward from the first biasing member 56 and received by the second plunger member 54. The second biasing member 58 is constrained between a second spring seat 66 of the second plunger member 54 and the first plunger member 52. The second biasing member 58 is configured to bias the first plunger 52 member towards the container 14 from the pre-use position, to the use position, and to the post-use position. The first biasing member 56 is configured to bias the second plunger member 54 towards the container 14, which, in turn, biases the first plunger member 52 towards the container 14 from the pre-use position, to the use position, and to the post-use position. More specifically, the second biasing member 58 is configured to drive the first plunger member 52 against the spacer assembly 40 or stopper 34 to move the container 14 into engagement the valve assembly 16 thereby piercing the closure 36 of the container 14 and placing the container 14 in fluid communication with the needle 28. The first biasing member 56 is configured to move the stopper 34 within the container 14 to dispense the medicament within the container 14. The second biasing member 58 has a different spring constant than the first biasing member 56. In particular, the second biasing 58 member is stiffer than the first biasing member 56 to provide a high force for piercing the closure 36 of the container 14 while the first biasing member 56 provides a lower force for dispensing as appropriate for the viscosity of the fluid or medicament within the container 14.

Referring again to FIGS. 17-26, the plunger actuation member 60 has an annular portion 68 and a spindle portion 70. The plunger actuation member 60 is rotationally moveable relative to the first plunger member 52 between a first rotational position and a second rotational position spaced from the first rotational position. The first rotational position may be 15 degrees from the second rotational position, although other suitable positions may be utilized. The annular portion 68 includes a drive surface 72 including a plurality of gears 74, although other suitable arrangements may be utilized for the drive surface 72. The spindle portion 70 includes an actuator locking surface 76 configured for engagement and release from a plunger locking surface 78 of the first plunger member 52. The plunger locking surface 78 includes a plurality of projections 80 configured to be received by a plurality of slots or cutouts 81 defined by the actuator locking surface 76.

Figure 18:
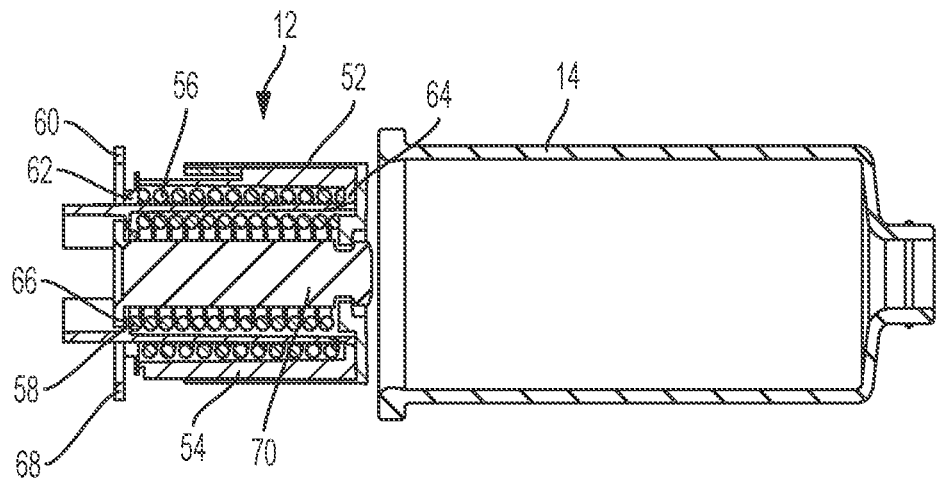
FIG. 18 is a cross-sectional view of the drive assembly of FIG. 17 according to one aspect of the present invention, showing a pre-use position of the drive assembly.
Figure 19:
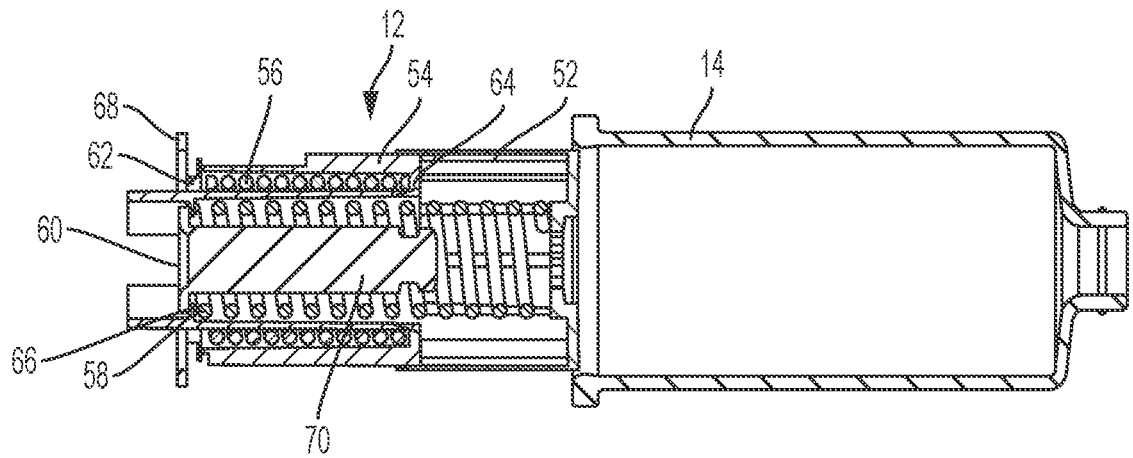
FIG. 19 is a cross-sectional view of the drive assembly of FIG. 17 according to one aspect of the present invention, showing a use position of the drive assembly.
Figure 20:
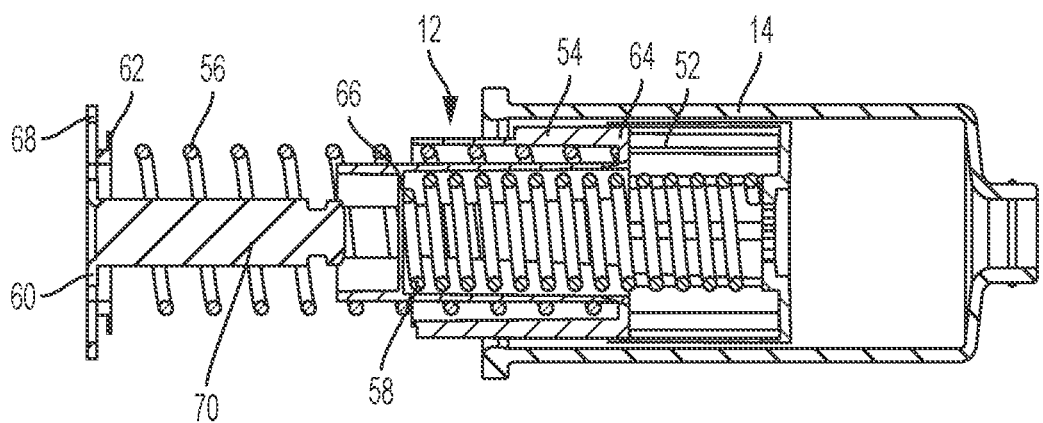
FIG. 20 is a cross-sectional view of the drive assembly of FIG. 17 according to one aspect of the present invention, showing a post-use position of the drive assembly.
Figure 21:
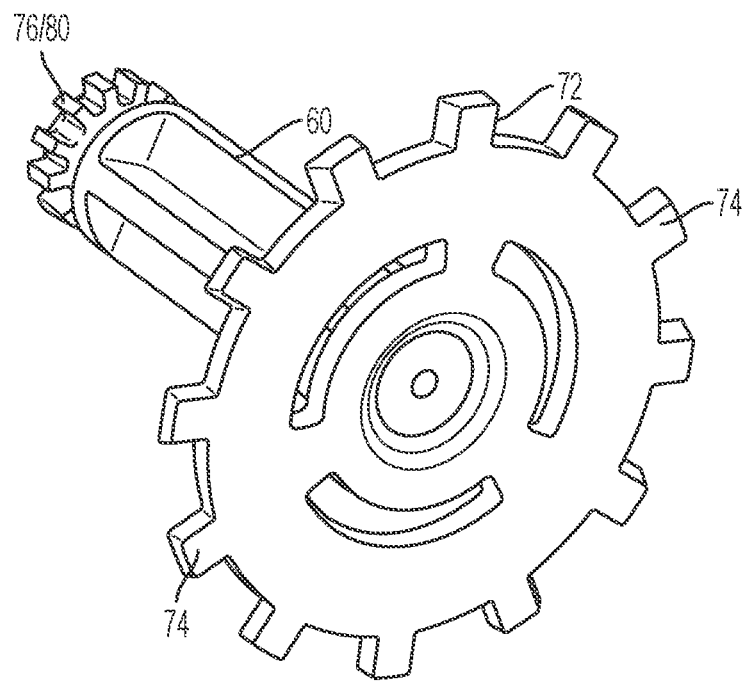
FIG. 21 is a perspective view of a plunger actuation member of the drive assembly of FIG. 17 according to one aspect of the present invention.
Figure 22:
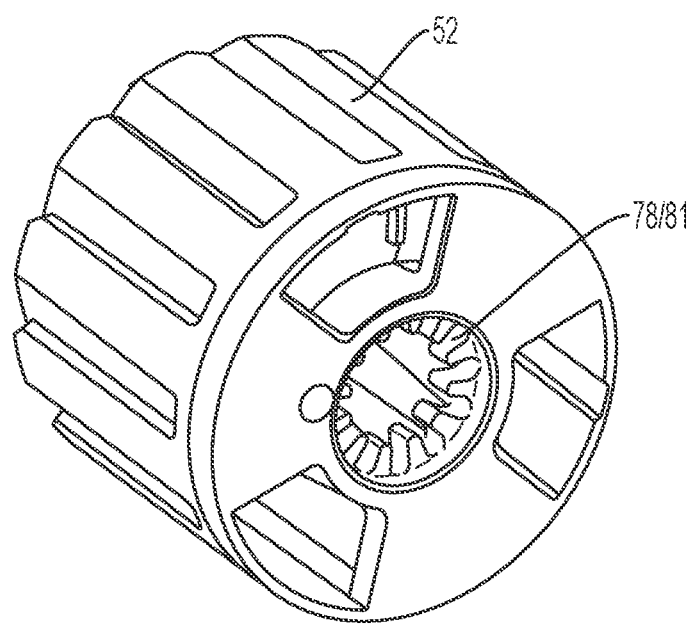
FIG. 22 is a perspective view of a first plunger member of the drive assembly of FIG. 17 according to one aspect of the present invention.
Figure 23:
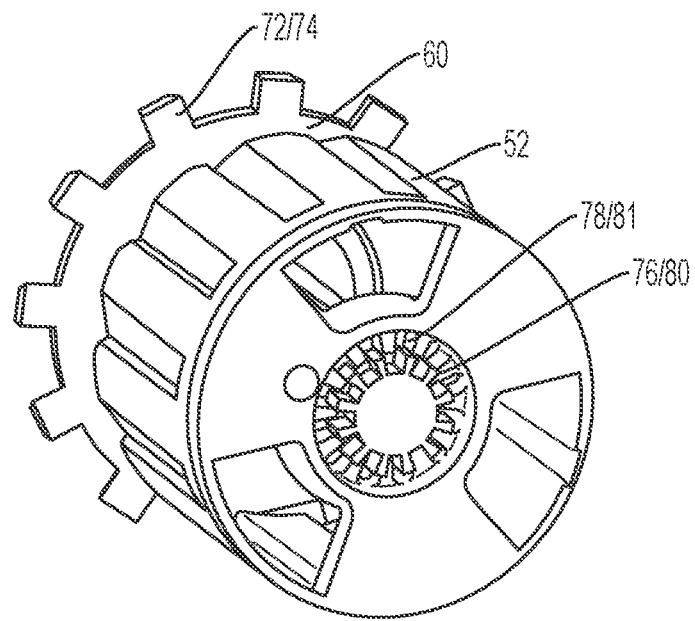
FIG. 23 is a perspective view of a plunger actuation member and first plunger member of the drive assembly of FIG. 17 according to one aspect of the present invention, showing the plunger actuation member engaged with the first plunger member.
Figure 24:
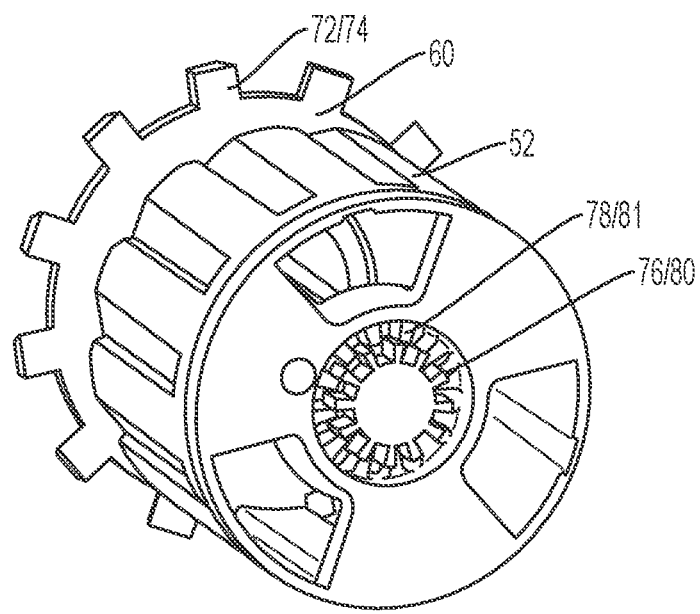
FIG. 24 is a perspective view of a plunger actuation member and first plunger member of the drive assembly of FIG. 17 according to one aspect of the present invention, showing the plunger actuation member disengaged from the first plunger member.
Figure 25:
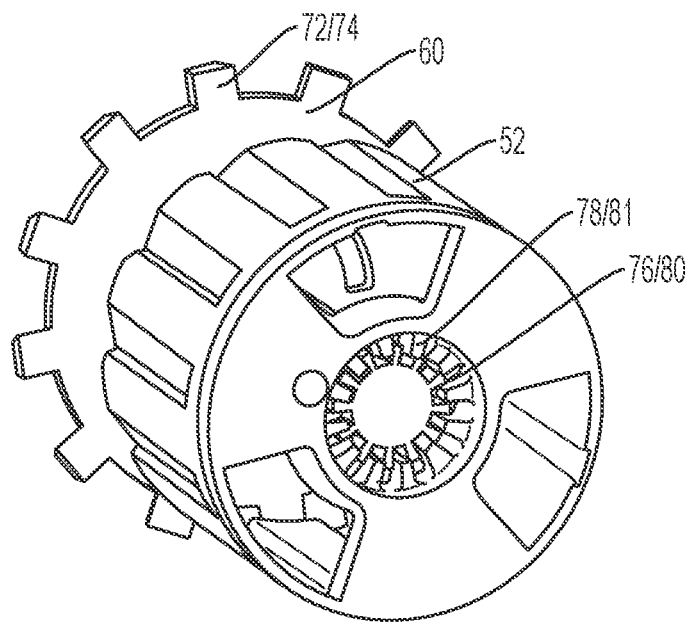
FIG. 25 is a perspective view of a plunger actuation member and first plunger member of the drive assembly of FIG. 17 according to one aspect of the present invention, showing the plunger actuation member disengaged from and axially displaced relative to the first plunger member.

As shown in FIGS. 18 and 23, in the first rotational position of the plunger actuation member 60, the plurality of projections 80 and the plurality of slots or cutouts 81 are out of alignment such that the plunger actuation member 80 is engaged with the first plunger member 52 to prevent movement of the first and second plunger members 52, 54 with the first and second biasing members 56, 58 biasing the first and second plunger members 52, 54 away from the plunger actuation member 60. As shown in FIGS. 19 and 24, in the second rotational position of the plunger actuation member 60, the plurality of projections 80 and the plurality of slots or cutouts 81 are aligned with each other such that the plunger actuation member 60 is disengaged with the first plunger member 52 to allow movement of the first and second plunger members 52, 54 thereby starting the dispensing process from the container 14.

Figure 33:
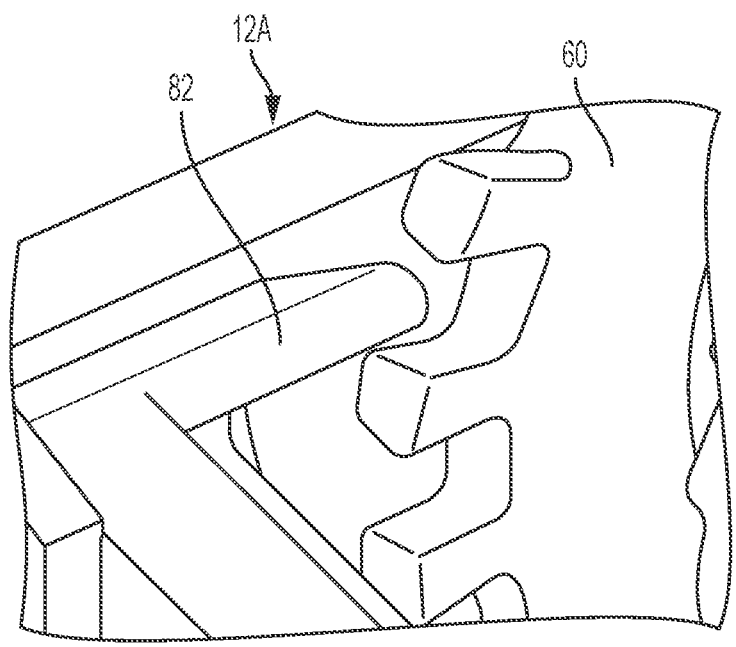
FIG. 33 is an enlarged perspective view of the drive assembly of FIG. 27 according to one aspect of the present invention, showing engagement of the drive assembly with a portion of a needle actuator in an initial actuation position of the drive assembly.
Figure 34:
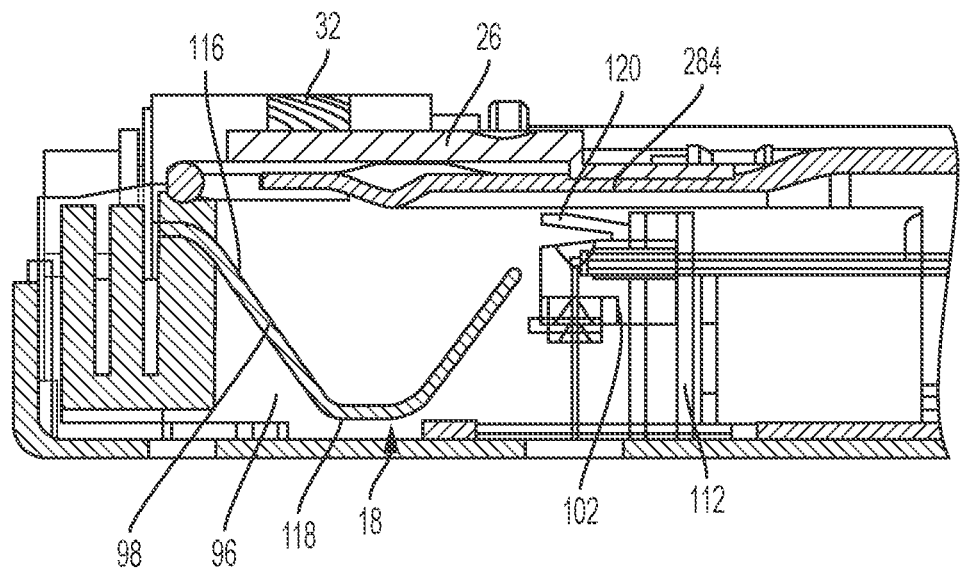
FIG. 34 is a front view of a needle actuator assembly according to one aspect of the present invention.
Figure 35:
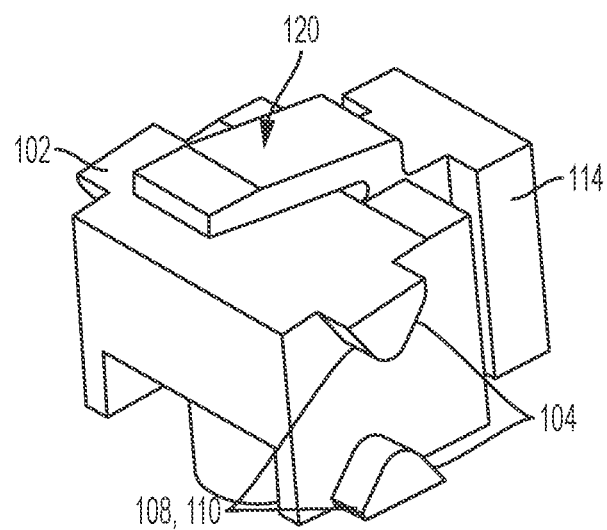
FIG. 35 is a left side perspective view of a needle shuttle of the needle actuator assembly of FIG. 34 according to one aspect of the present invention.
Figure 36:
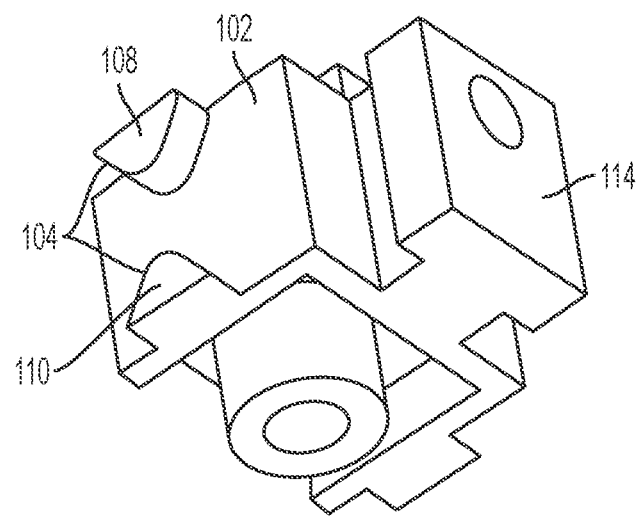
FIG. 36 is a right side perspective view of a needle shuttle of the needle actuator assembly of FIG. 34 according to one aspect of the present invention.
Figure 37A:
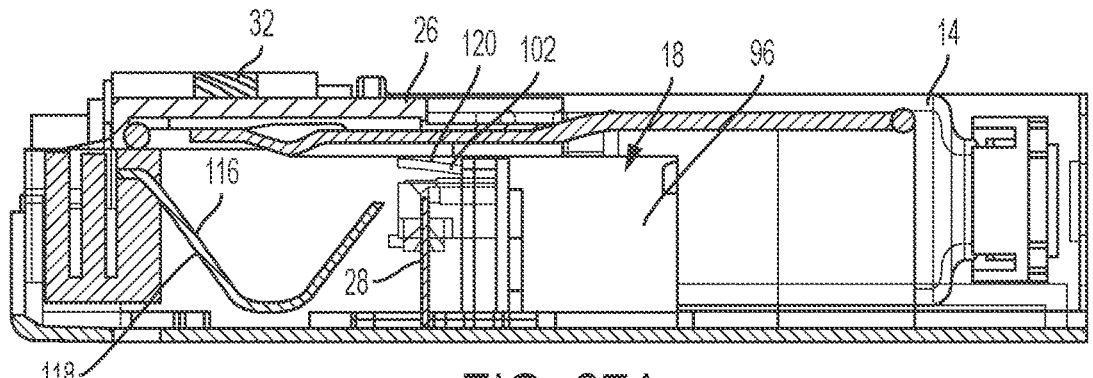
FIG. 37A is a front view of the needle actuator assembly of FIG. 34 according to one aspect of the present invention, showing the needle actuator assembly in a pre-use position.
Figure 37B:
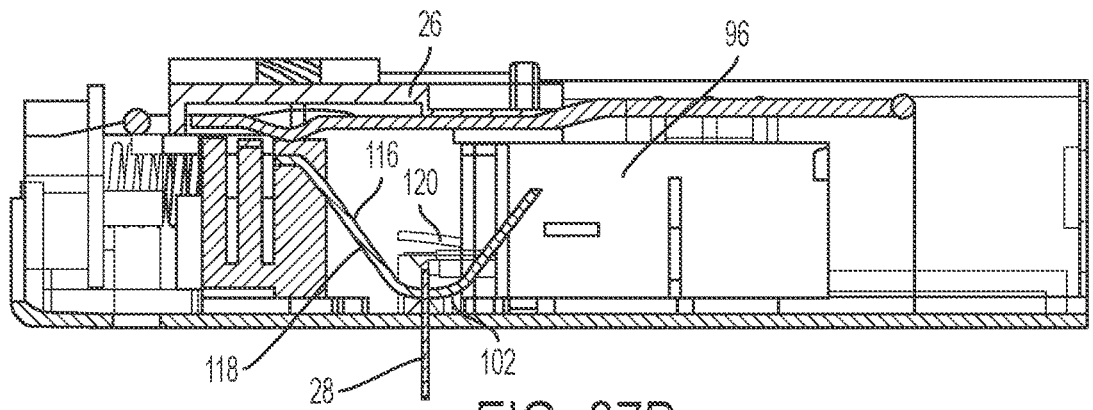
FIG. 37B is a front view of the needle actuator assembly of FIG. 34 according to one aspect of the present invention, showing the needle actuator assembly in a use position.
Figure 37C:
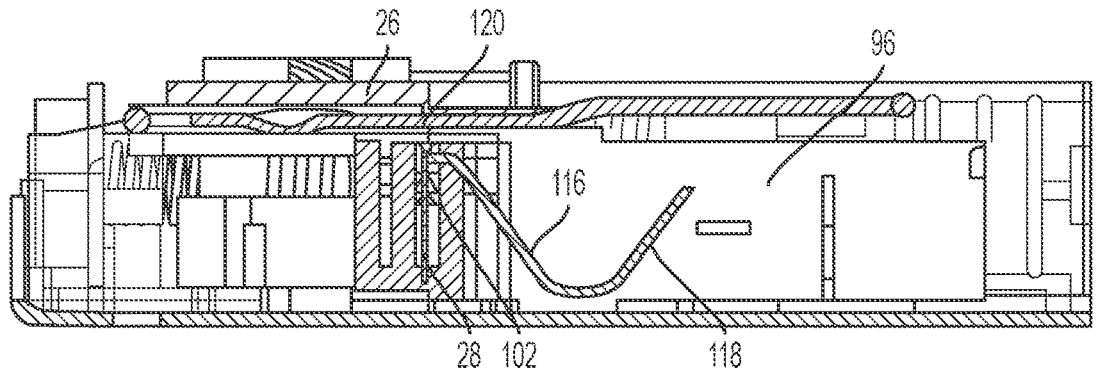
FIG. 37C is a front view of the needle actuator assembly of FIG. 34 according to one aspect of the present invention, showing the needle actuator assembly in an initial post-use position.
Figure 37D:
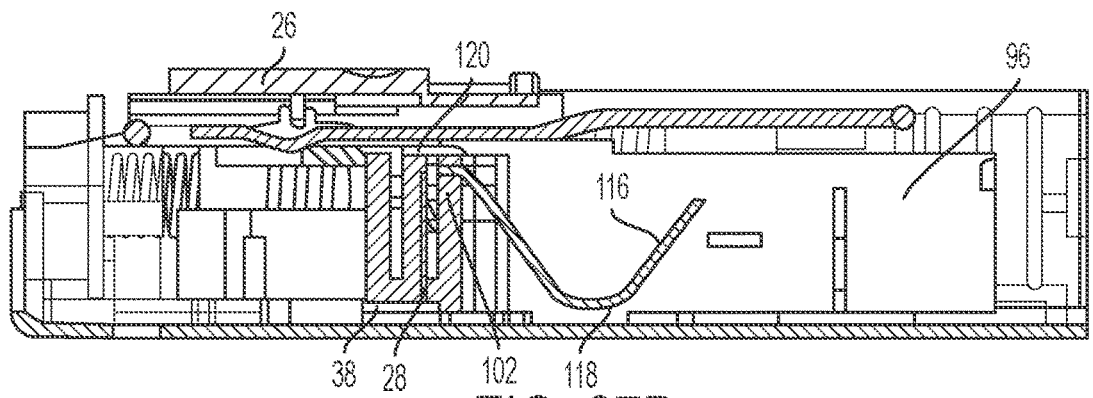
FIG. 37D is a front view of the needle actuator assembly of FIG. 34 according to one aspect of the present invention, showing the needle actuator assembly in a post-use position.
Figure 38A:
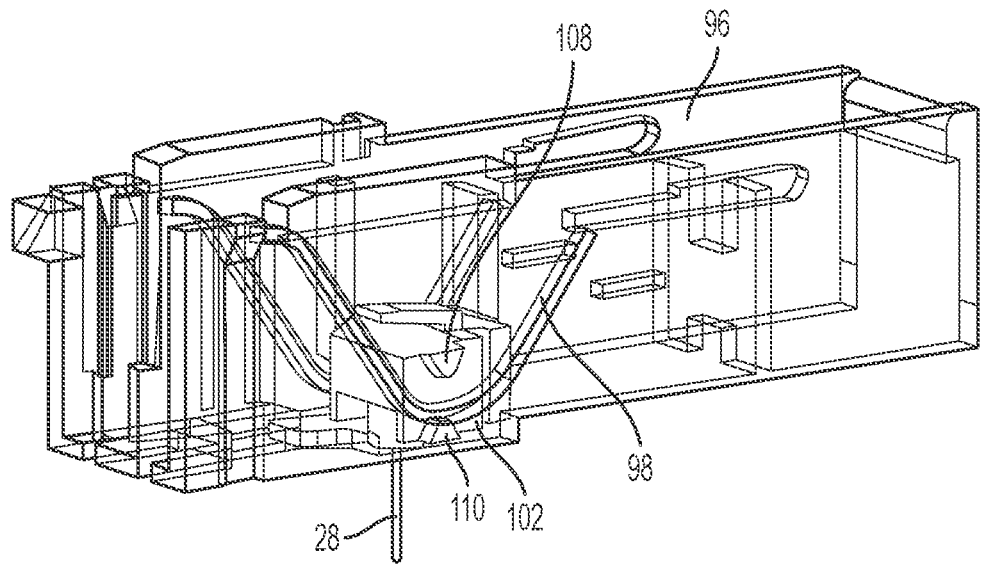
FIG. 38A is a perspective view of the needle actuator assembly of FIG. 34 according to one aspect of the present invention, showing the needle actuator assembly in a use position.
Figure 38B:
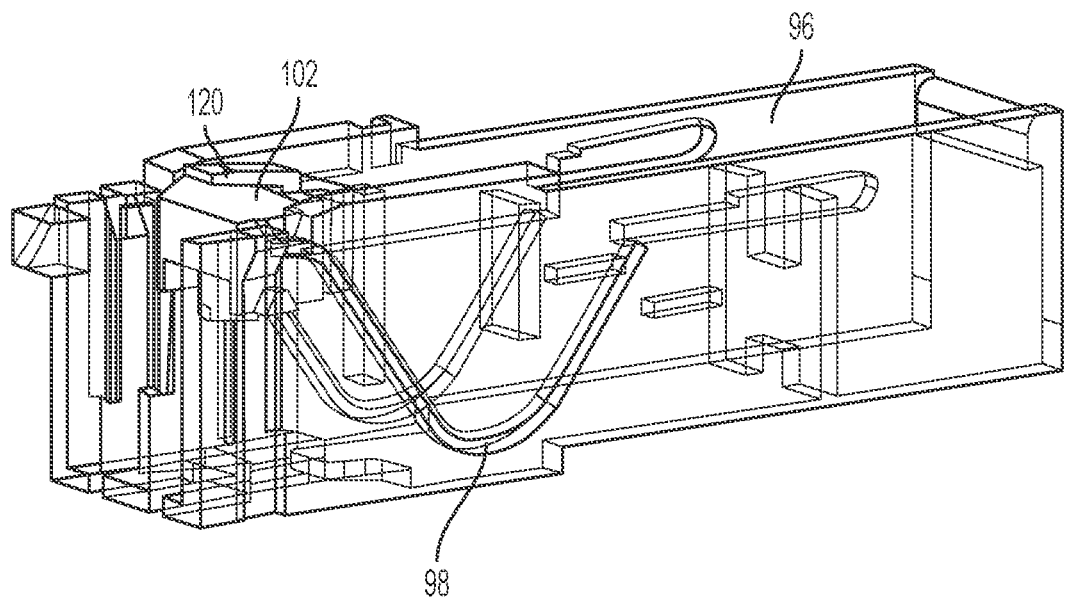
FIG. 38B is a perspective view of the needle actuator assembly of FIG. 34 according to one aspect of the present invention, showing the needle actuator assembly in an initial post-use position.

Referring to FIGS. 7 and 33, the drive surface 72 of the plunger actuation member 60 is configured to be engaged by a portion of the needle actuator assembly 18. After engagement of the actuator button 26 and release of the needle actuator assembly 18, which is discussed in more detail below, the needle actuator assembly 18 moves within the housing 20 from the pre-use position, to the use position, and to the post-use position. During the initial movement of the needle actuator assembly 18, a portion of the needle actuator assembly 18 engages the drive surface 72 of the plunger actuation member 60 to move the plunger actuation member 60 from the first rotational position to the second rotational position. As shown in FIG. 33, an angled blade portion 82 of the needle actuator assembly 18 engages the drive surface 72 of the plunger actuation member 60 to cause rotation of the plunger actuation member 60.

Figure 13:
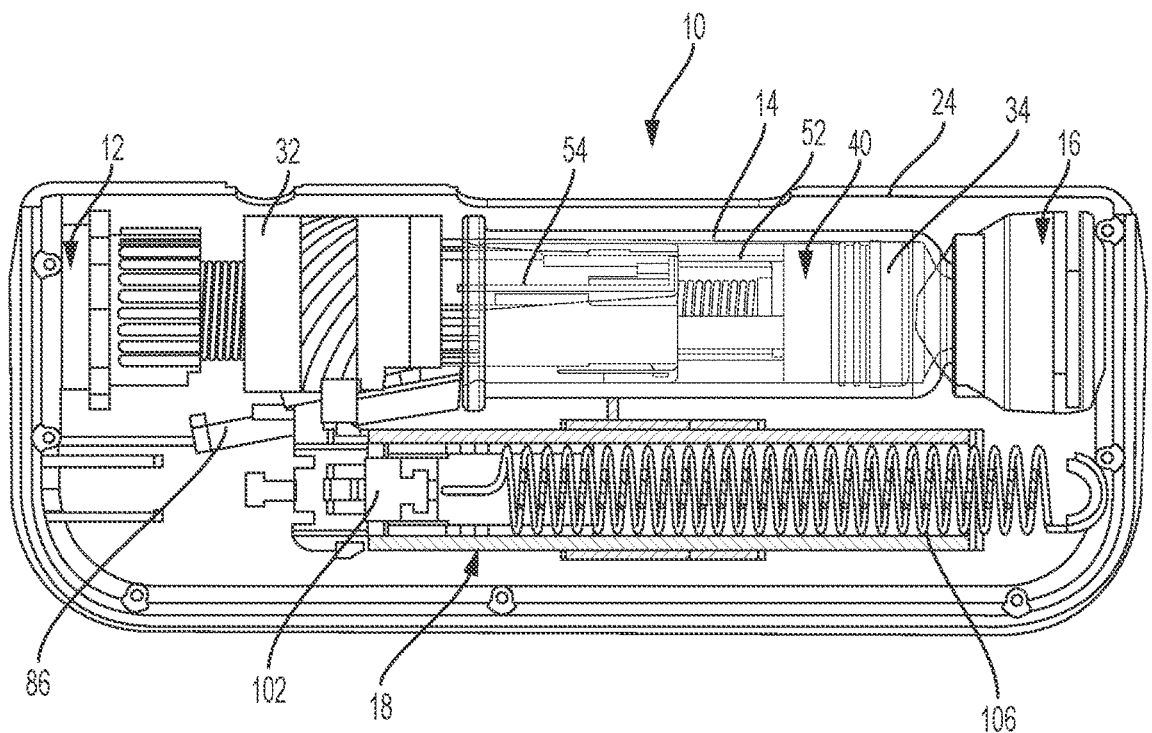
FIG. 13 is a top view of the drug delivery system of FIG. 1 according to one aspect of the present invention, showing a top portion of the housing removed and the drug delivery system in a post-use position.
Figure 14:
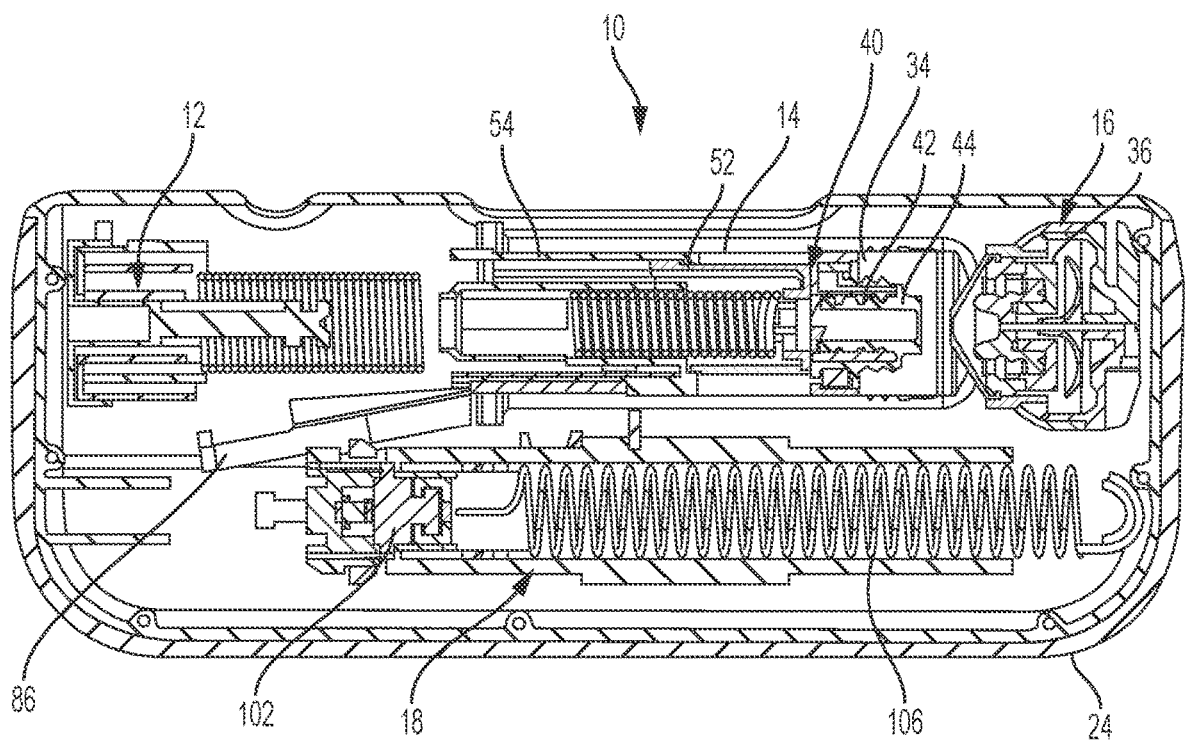
FIG. 14 is a top, cross-sectional view of the drug delivery system of FIG. 1 according to one aspect of the present invention, showing the drug delivery system in a post-use position.
Figure 26:
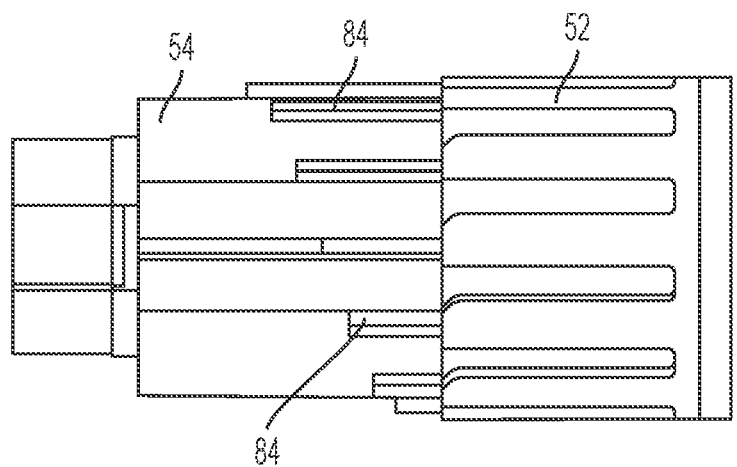
FIG. 26 is a front view of a first plunger member and a second plunger member of the drive assembly of FIG. 17 according to one aspect of the present invention.
Figure 27:
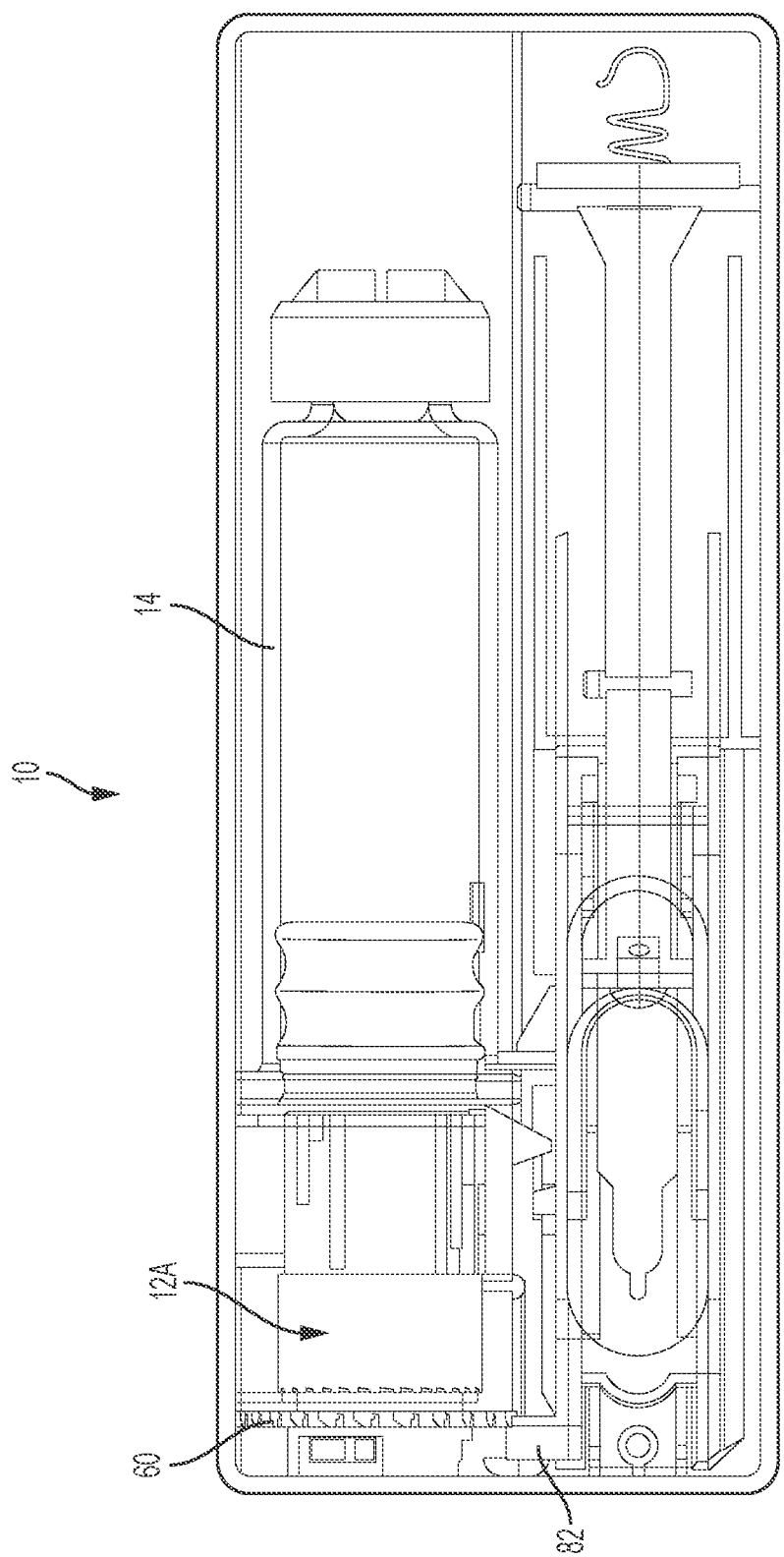
FIG. 27 is a top view of a drive assembly for a drug delivery system according to a further aspect of the present invention.
Figure 28:
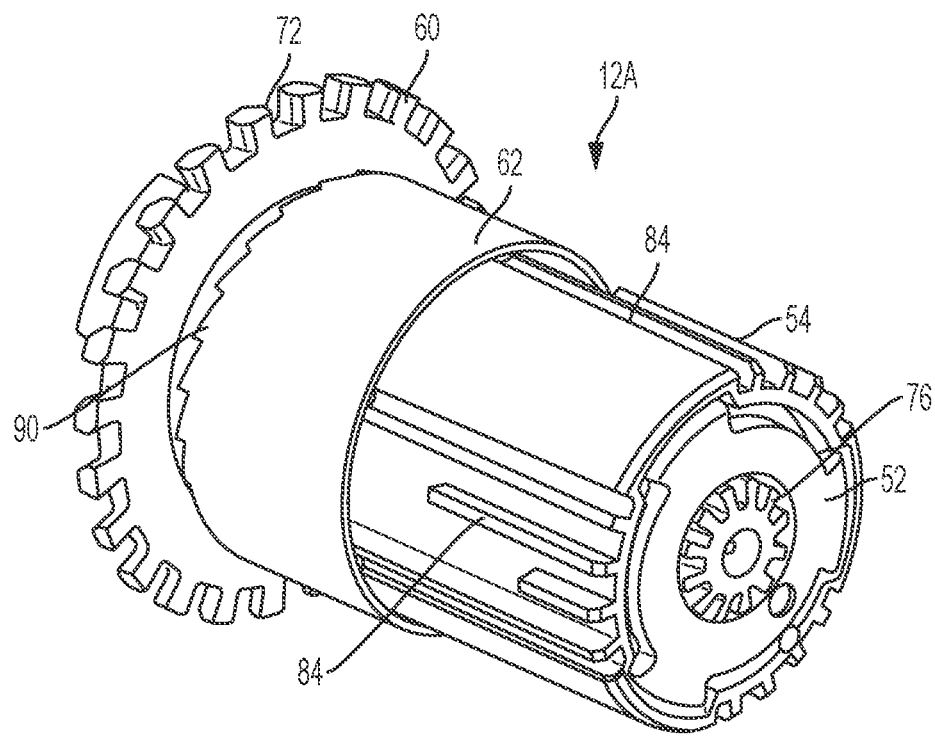
FIG. 28 is a perspective view of the drive assembly of FIG. 27 according to one aspect of the present invention.
Figure 29:
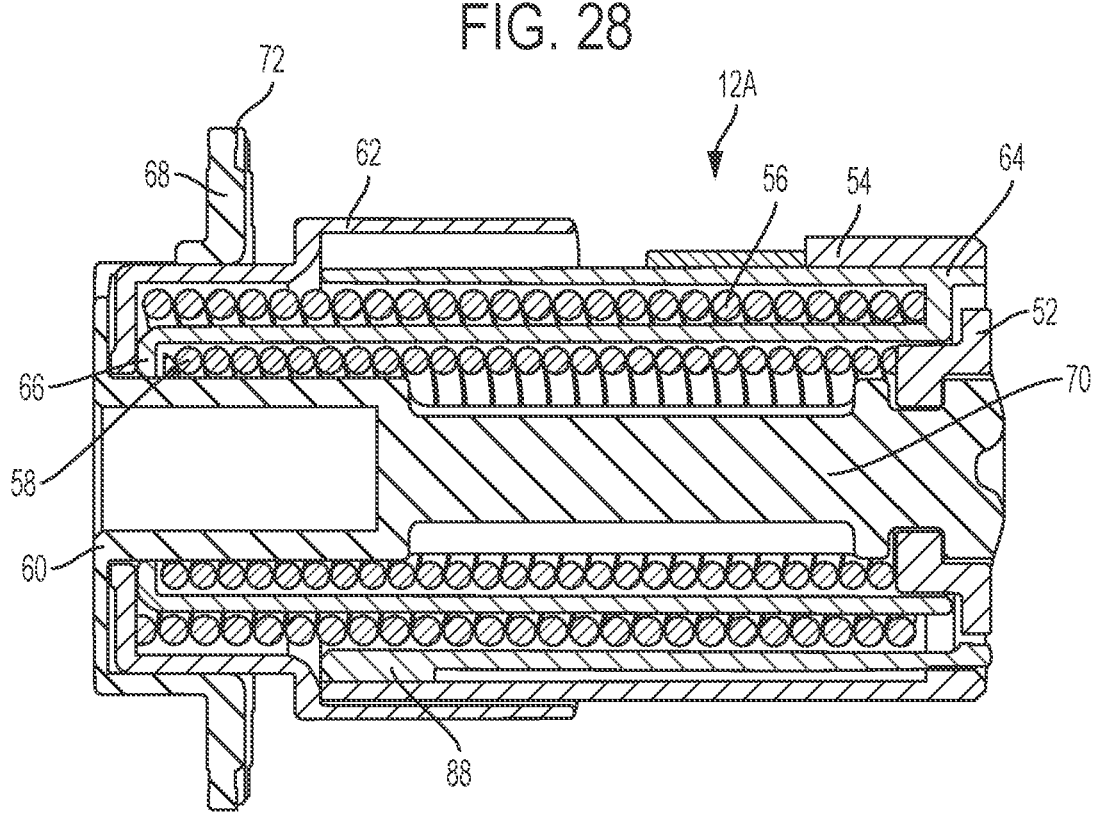
FIG. 29 is a cross-sectional view of the drive assembly of FIG. 27 according to one aspect of the present invention, showing a pre-use position of the drive assembly.
Figure 30:
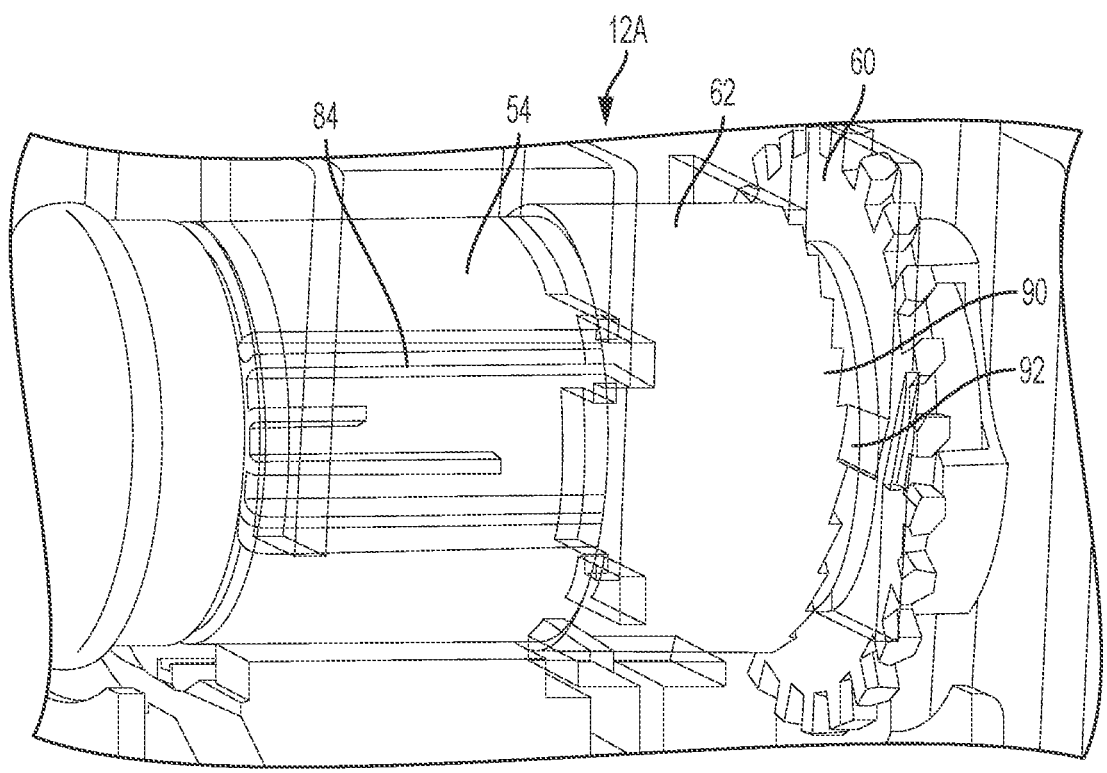
FIG. 30 is a perspective view of the drive assembly of FIG. 27 according to one aspect of the present invention, showing the drive assembly received by a bottom portion of a housing.
Figure 31:
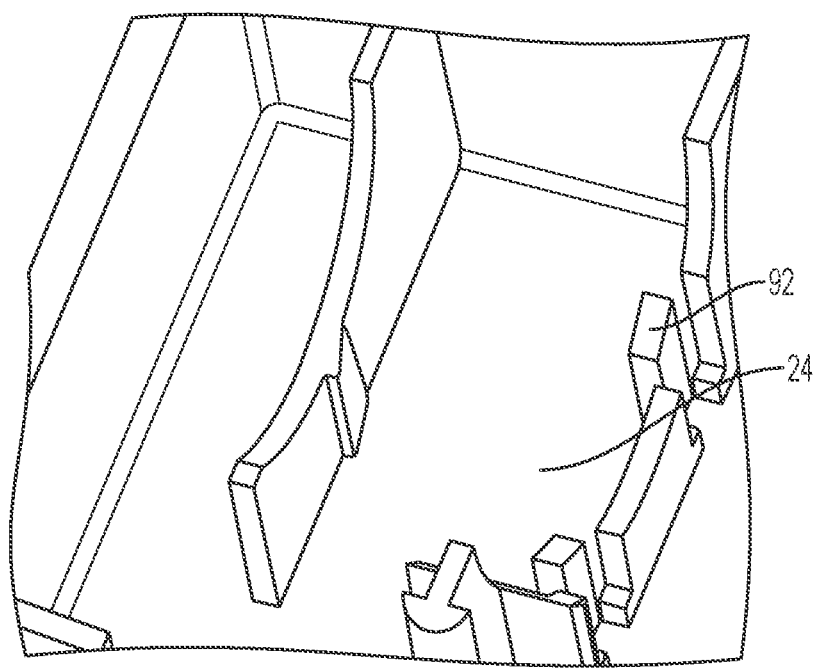
FIG. 31 is a perspective view of the housing of FIG. 30 according to one aspect of the present invention.
Figure 32:
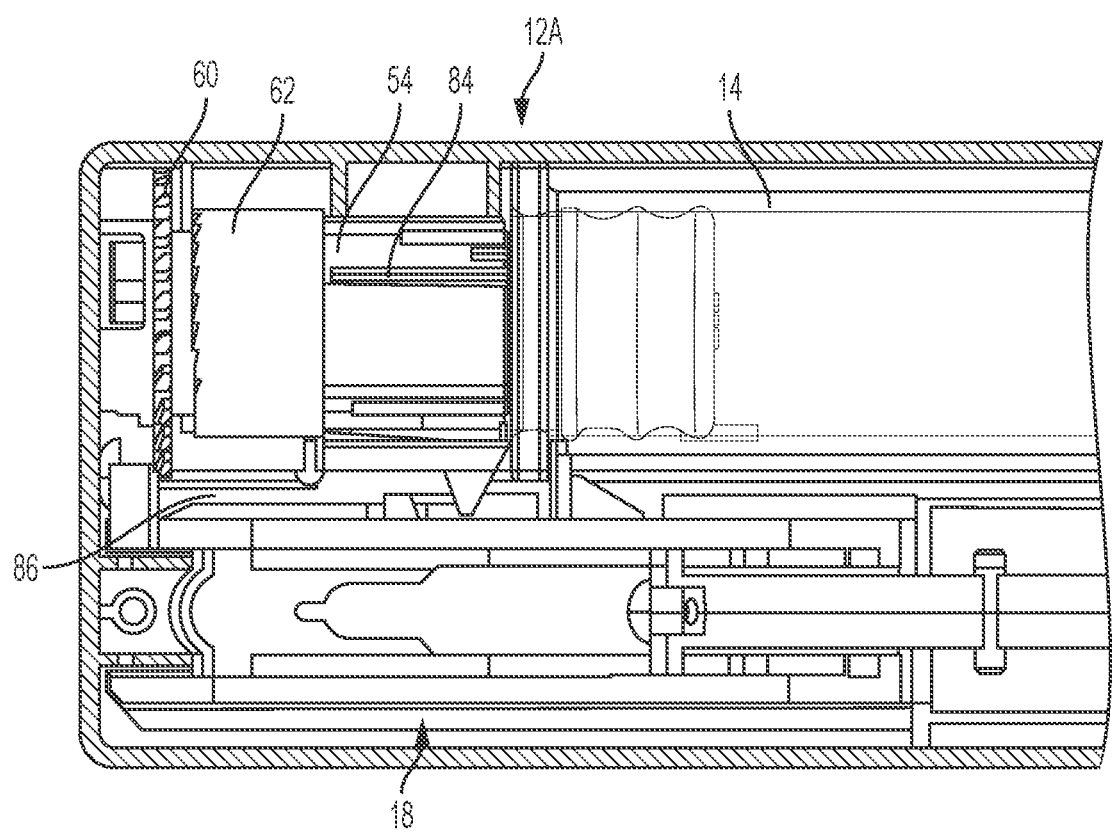
FIG. 32 is a top view of the drive assembly of FIG. 27 according to one aspect of the present invention, showing engagement of the drive assembly with a portion of a needle actuator in an initial actuation position of the drive assembly.

Referring to FIGS. 11, 13, and 26, the second plunger member 52 includes a plurality of coded projections 84 with a preselected one of the plurality of coded projections 84 configured to engage a restriction member 86 of the system 10. As discussed in more detail below, the restriction member 86 cooperates with the needle actuation assembly 18 and restricts movement of the needle actuator assembly 18 from the use position to the post-use position until a predetermined end-of-dose position of the stopper 34 is reached. In one aspect, the restriction member 86 is configured to restrict axial movement of the needle actuation assembly 18 from the use position through engagement between the restriction member 86 and a portion of the needle actuation assembly 18. Such engagement between the restriction member 86 and the needle actuation assembly 18 is released by rotation of the restriction member 86 when the stopper 34 reaches the end-of-dose position. During the use position of the needle actuator assembly 18, the restriction member 86 is biased in a rotational direction with the rotation of the restriction member 86 being prevented through engagement between the restriction member 86 and one of the plurality of coded projections 84 of the second plunger member 54. The plurality of coded projections 84 may be axial ribs of varying length, although other suitable arrangements may be utilized. Each coded projection 84 defines a point at which the restriction member 86 is able to rotate thereby releasing the needle actuator assembly 18. The smooth portion of the second plunger member 52 may also provide a further "code" for determining when the system 10 transitions to the end-of-dose position.

As discussed above, the indicator arrangement 32 moves with different portions of the indicator arrangement 32 visible through the indicator window 30 as the system 10 moves from the pre-use, use, and post-use or end-of-dose positions. More specifically, the indicator arrangement 32 engages a portion of the restriction member 86 and moves along with the restriction member 86 through the various stages of the system 10 to provide an indication to the user regarding the state of the system 10.

During assembly of the system 10, the dosage of the container 14 is matched with a specific spacer 42 having a set length and a corresponding one of the plurality of coded projections 84 is aligned with the restriction member 86. Accordingly, as discussed above, the container 14 may be provided with a plurality of dosage volumes with each volume corresponding to a specific spacer 42 and coded projection 84. Thus, even for different dosage volumes, the system 10 is configured to inject the needle 28 into the user to deliver a dose of medicament from the container 14, retract the needle 28 after the end of the dose, and provide an indication of the status of the system 10 while minimizing abrupt engagement of the stopper 34 by the drive assembly 12. In particular, the size of the stopper 34 may be selected to minimize the distance between the first plunger member 52 and the spacer assembly 40 and does not require the use of damping.

Referring to FIGS. 27-33, a drive assembly 12A according to a further aspect of the present invention is shown. The drive assembly 12A shown in FIGS. 27-33 is similar to and operates in the same manner as the drive assembly 12 shown in FIGS. 17-26 and described above. In the drive assembly of FIGS. 27-33, however, the first plunger member 52 is received by the second plunger member 54 and extends from the second plunger member 54 during axial movement from the pre-use position to the use position. Further, the first plunger member 52 includes an extension portion 88 configured to engage the second plunger member 54 after the first plunger member 52 moves predetermined axial distance such that the first and second plunger members 52, 54 move together. The first and second biasing members 56, 58 engage and act on the first and second plunger members 52, 54 in the same manner as the drive assembly 12 of FIGS. 17-26.

Referring to FIGS. 27-32, the index member 62 is positioned about the first and second plunger members 52, 54 and includes a plurality of ratchet teeth 90 configured to engage a flexible tab 92 positioned on the bottom portion 24 of the housing 20. When the drive assembly 12, 12A is installed into the bottom portion 24 of the housing 20, the engagement of the ratchet teeth 90 of the index member 62 with the flexible tab 92 of the housing 20 provide a one-way rotation of the index member 62. The index member 62 is configured to rotate to align one of the coded projections 84 of the second plunger member 52 with the restriction member 86 based on the dosage volume and spacer 42 size as discussed above. The index member 62 may provide the drive assembly 12, 12A with 24 rotational positions of which 12 may have unique dose values associated with them.

Referring to FIGS. 1-16 and 34-40B, the needle actuator assembly 18 according to one aspect of the present invention is shown. The needle actuator assembly 18 includes a needle actuator body 96 having guide surfaces 98, a needle shuttle 102 having cam surfaces 104, and the needle 28 received by the needle shuttle 102 and configured to be in fluid communication with the container 14 as discussed above. The needle actuator body 96 is generally rectangular with the guide surfaces 98 protruding radially inward. The needle shuttle 102 is received within the needle actuator body 96. As described above, the needle actuator body 96 is moveable within the housing 20 from a pre-use position (shown in FIGS. 4-6), an initial actuation position (FIGS. 7-9), a use position (FIGS. 10-12), and a post-use position (FIGS. 13-15A). The needle actuator body 96 is biased from the pre-use position to the post-use position via an extension spring 106, although other suitable biasing arrangements may be utilized. The needle actuator body 96 is released and free to move from the pre-use position to the use position upon engagement of the actuator button 26, which is discussed in more detail below. The needle actuator body 96 moves from the use position to the post-use position after rotation of the restriction member 86 as discussed above in connection with FIGS. 17-33.

Referring to FIGS. 34-40B, the needle shuttle 102 is moveable along a vertical axis between a retracted position where the needle 28 is positioned within the housing 20 and an extended position where at least a portion of the needle 28 extends out of the housing 20. The needle shuttle 102 is configured to move between the retracted position and the extended position through engagement between the guide surfaces 98 of the needle actuator 96 and the cam surfaces 104 of the needle shuttle 102. The cam surfaces 104 are provided by first and second cam members 108, 110, with the first cam member 108 spaced from the second cam member 110. The housing 20 includes a guide post 112 having recess configured to receive a T-shaped projection 114 on the needle shuttle 102, although other shapes and configurations may be utilized for the guide post 112 and T-shaped projection 114. The needle shuttle 102 moves along the guide post 112 between the retracted and extended positions. The guide post 112 is linear and extends about perpendicular from the housing 20, although other suitable arrangements may be utilized. The guide surfaces 98 of the needle actuator body 86 are non-linear and each include a first side 116 and a second side 118 positioned opposite from the first side 116.

As discussed below, the guide surfaces 98 of the needle actuator body 96 cooperate with the cam members 108, 110 of the needle shuttle 102 to move the needle shuttle 102 vertically between the retracted and extended positions as the needle actuator body 96 moves axially from the pre-use position to the post-use position. The needle shuttle 102 also includes a shuttle biasing member 120 configured to engage the housing 20 or the actuator button 26. In particular, the shuttle biasing member 120 engages the housing 20 or actuator button 26 and provides a biasing force when the needle actuator body 96 is transitioning from the use position to the post-use position. When the needle actuator body 96 is fully transitioned to the post-use position, the cam members 108, 110 of the needle shuttle 102 are disengaged from the guide surfaces 98 of the needle actuator body 96 and the shuttle biasing member 120 biases the needle shuttle 102 downward such that the needle 28 engages the pad 38, as discussed above. As discussed above in connection with FIGS. 1-16, however, the pad 38 may also be biased into the needle 28 rather than biasing the needle shuttle 102 downwards via the shuttle biasing member 120. The needle actuator body 96 may interact with the actuator button 26 to prevent the actuator button 26 from popping back up until the post-use position is reached, which is discussed below in more detail.

Figure 39:
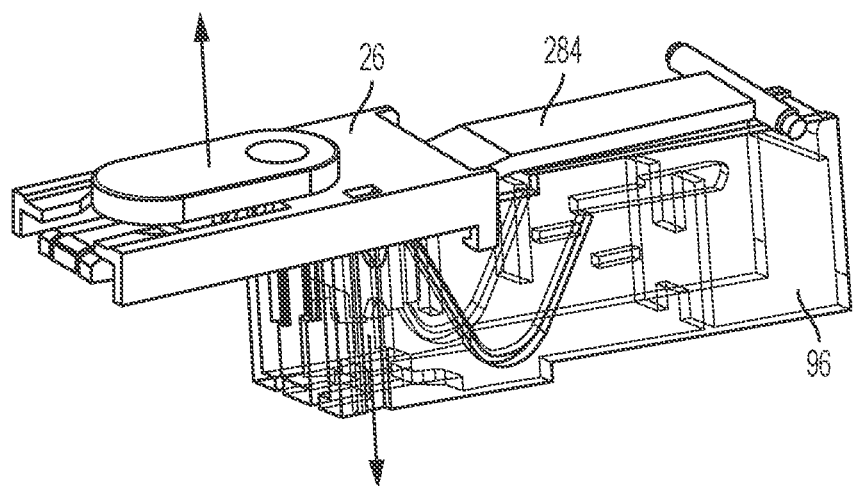
FIG. 39 is a perspective view of an actuator button and the needle actuator assembly of FIG. 34 according to one aspect of the present invention, showing the needle actuator assembly in an initial post-use position.
Figure 40A:
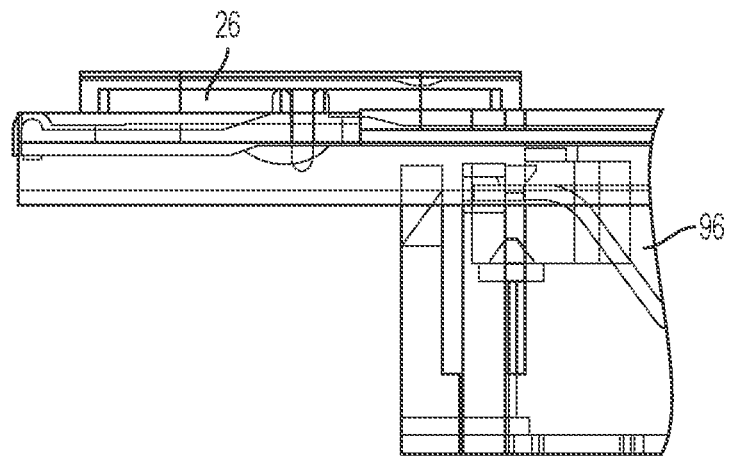
FIG. 40A is a cross-sectional view of an actuator button and the needle actuator assembly of FIG. 34 according to one aspect of the present invention, showing the needle actuator assembly in an initial post-use position.
Figure 40B:
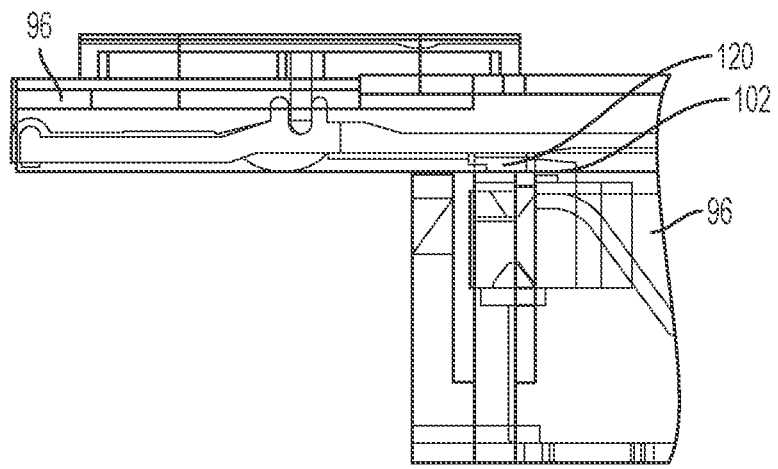
FIG. 40B is a perspective view of an actuator button and the needle actuator assembly of FIG. 34 according to one aspect of the present invention, showing the needle actuator assembly in a post-use position.
Figure 41:
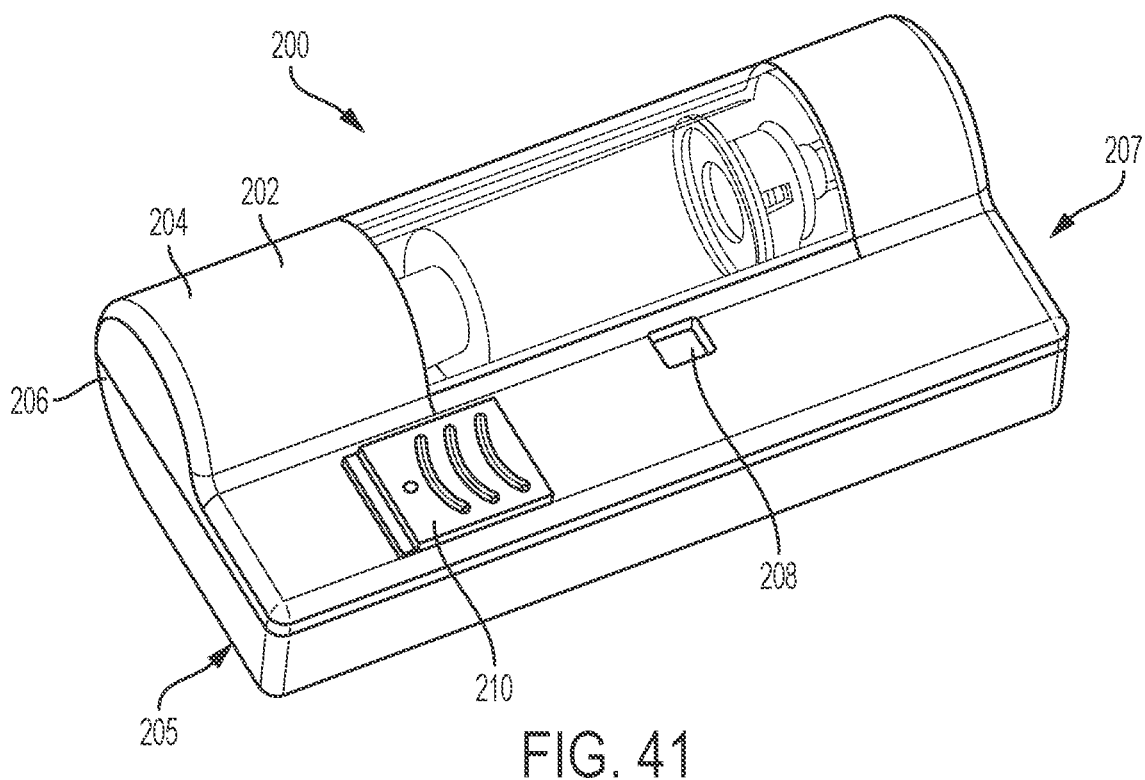
FIG. 41 is a perspective view of a drive assembly for a drug delivery system according to a further aspect of the present invention.
Figure 42:
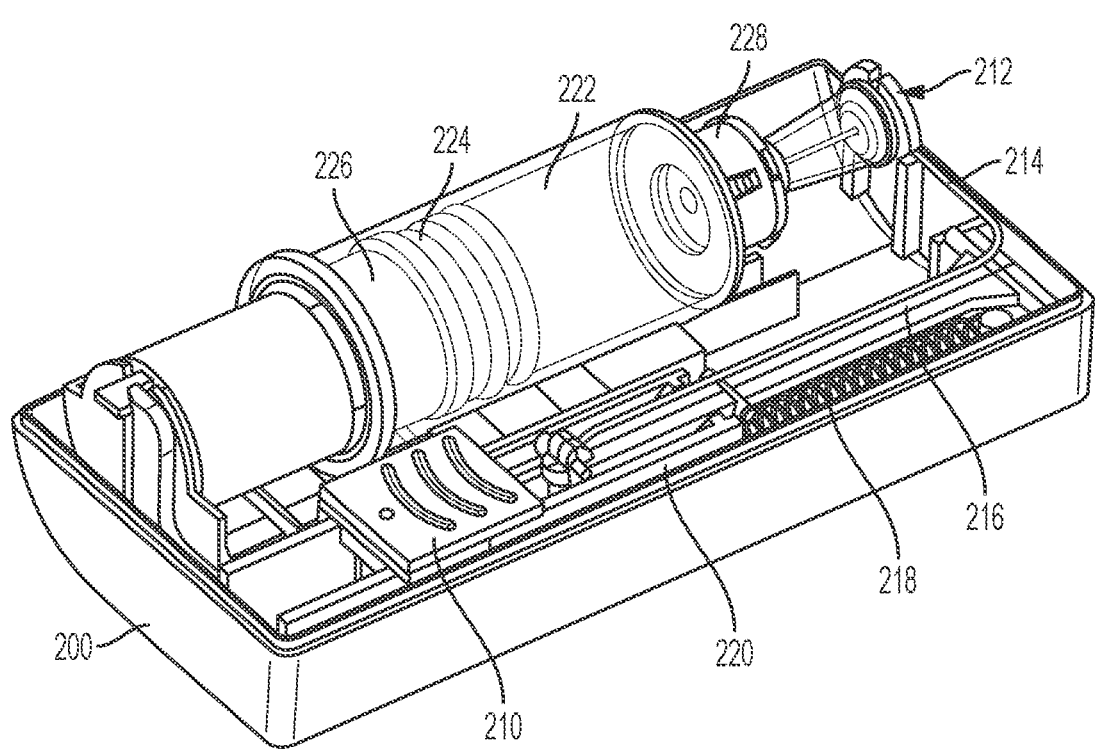
FIG. 42 is a perspective view of the drive assembly of FIG. 41 according to one aspect of the present invention, showing a top portion of a housing removed.
Figure 43:
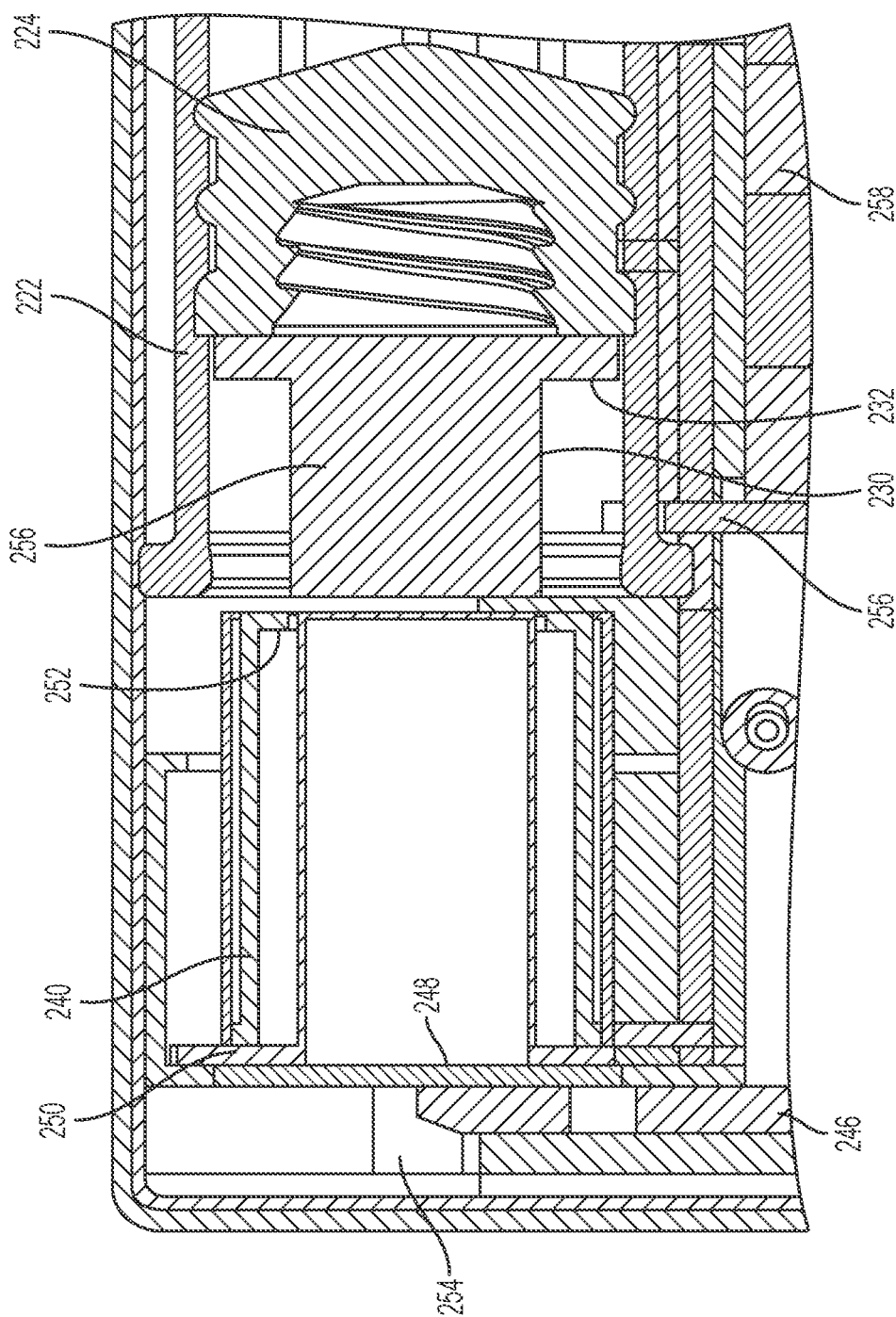
FIG. 43 is a cross-sectional view of the drive assembly of FIG. 41 according to one aspect of the present invention.
Figure 44:
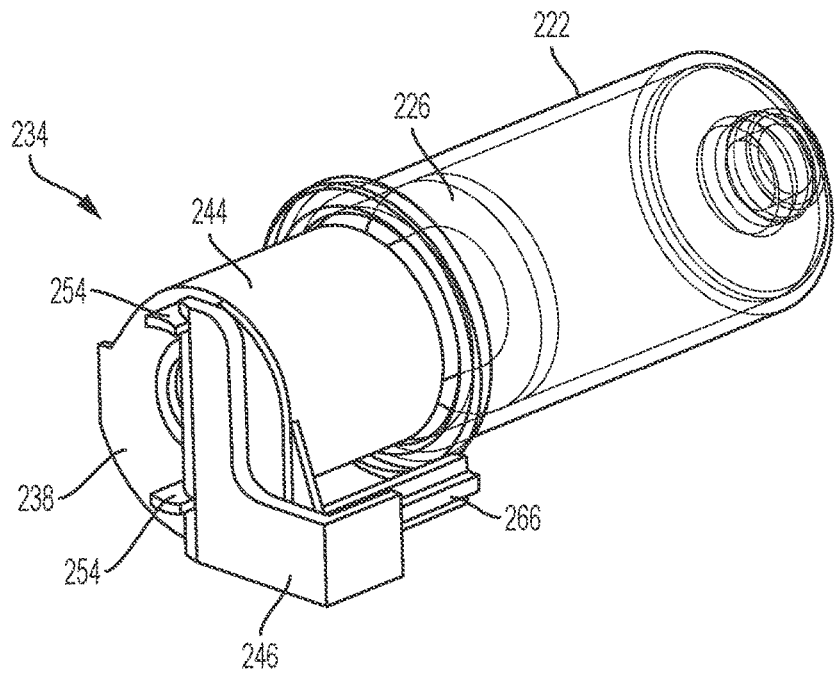
FIG. 44 is a perspective view of the drive assembly of FIG. 41 according to one aspect of the present invention.

Referring to FIGS. 37A-40B, in a pre-use position (FIG. 37A), the needle shuttle 102 is in the retracted position with the cam members 108, 110 spaced from the guide surface 98 of the needle actuator body 96. As the needle actuator body 96 moves to the use position (FIGS. 37B and 38A), the second cam member 110 of the needle shuttle 102 engages the second side 118 of the guide surfaces 98 to move the needle shuttle 102 from the retracted position to the extended position. During the transition from the use position to the post-use position of the needle actuator body 96 (FIG. 37C), the first cam member 108 of the needle shuttle 102 is engaged with the first side 116 of the guide surfaces 98 to move the needle shuttle 102 from the second position to the first position. After the needle actuator body 96 is fully transitioned to the post-use position (FIGS. 37D and 38B), the shuttle biasing member 120 biases the needle shuttle 102 downward as the cam members 108, 110 disengage from the guide surfaces 98 of the needle actuator body 96 with the needle 28 engaging the pad 38. The transition of the needle actuator body 96 and the corresponding position of the needle shuttle 102 is also shown in FIGS. 39-40B. The interaction between the actuator button 26 and the needle actuator body 96 is discussed in detail in connection with FIGS. 65A-67. Referring to FIGS. 41-64, a drug delivery system 200 according to a further embodiment is shown. The system 200 includes a housing 202 having an upper housing 204 and a lower housing 206. The housing has a proximal end 205 and a distal end 207. The upper housing 204 has a status view port 208 so that a user can view the operating status of the system 200. The system 200 also includes a valve assembly 212, a tube 214 fluidly connecting the valve assembly 214 with a patient needle 215 that is disposed in a proximal end of a needle arm 216. A spring 218 biases a needle actuator 220 distally.

As shown in FIGS. 42-46, the system 200 additionally includes a container or medicament container 222 with a stopper 224 movably disposed therein, although the stopper 224 is omitted from various figures to aid clarity. Preferably, the distal end of the medicament container 222 has a septum assembly 228 that is spaced apart from the valve assembly 212 prior to actuation of the device 222, as best shown in FIG. 47.

Figure 45:
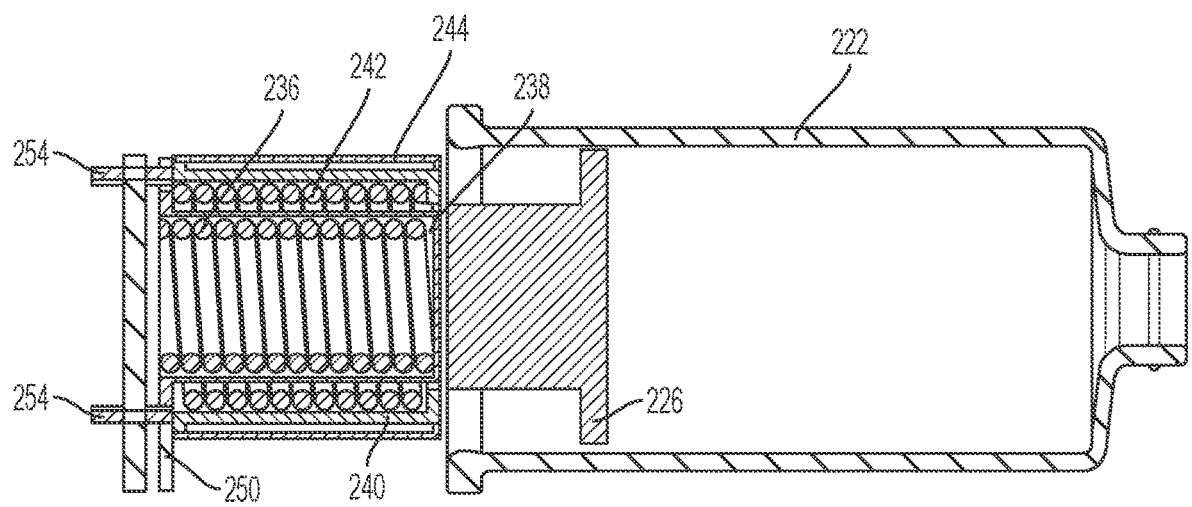
FIG. 45 is a cross-sectional view of the drive assembly of FIG. 41 according to one aspect of the present invention, showing the drive assembly in a pre-use position.
Figure 46:
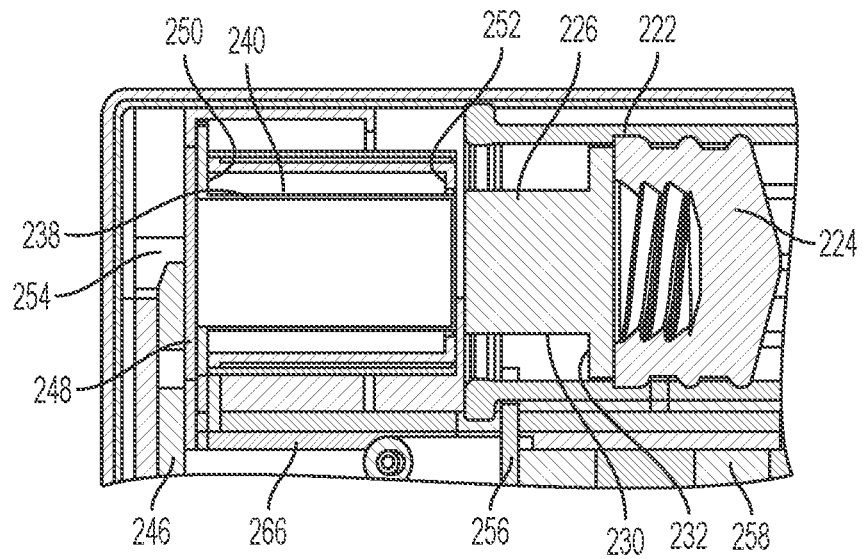
FIG. 46 is a cross-sectional view of the drive assembly of FIG. 41 according to one aspect of the present invention, showing the drive assembly in a pre-use position.
Figure 47:
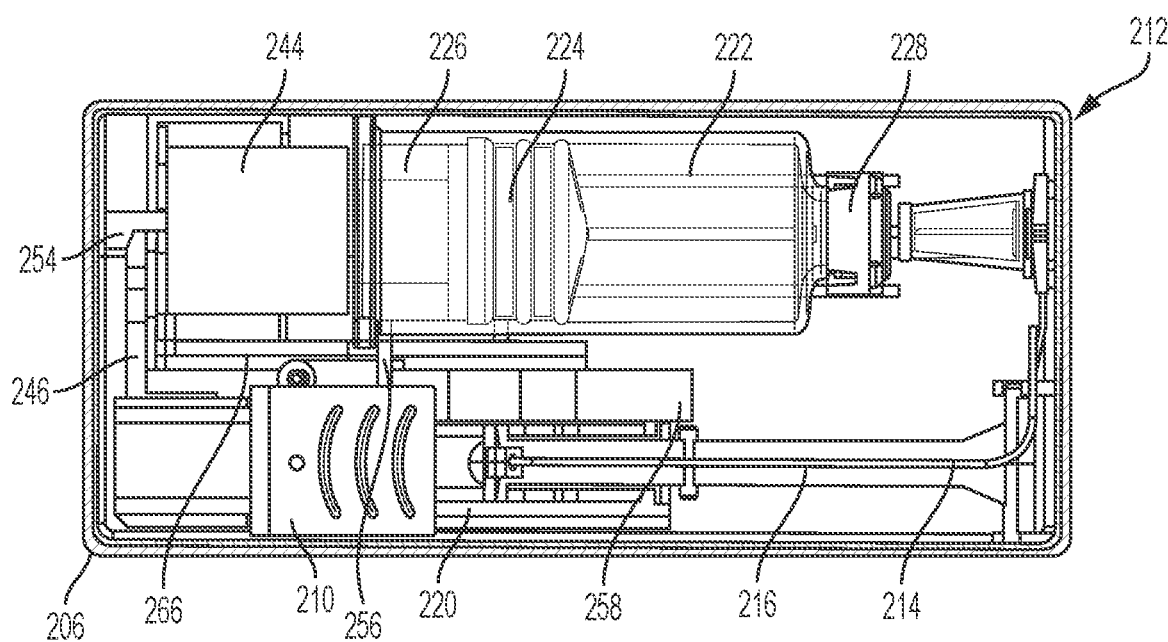
FIG. 47 is a top view of the drive assembly of FIG. 41 according to one aspect of the present invention, showing the drive assembly in a pre-use position.
Figure 48:
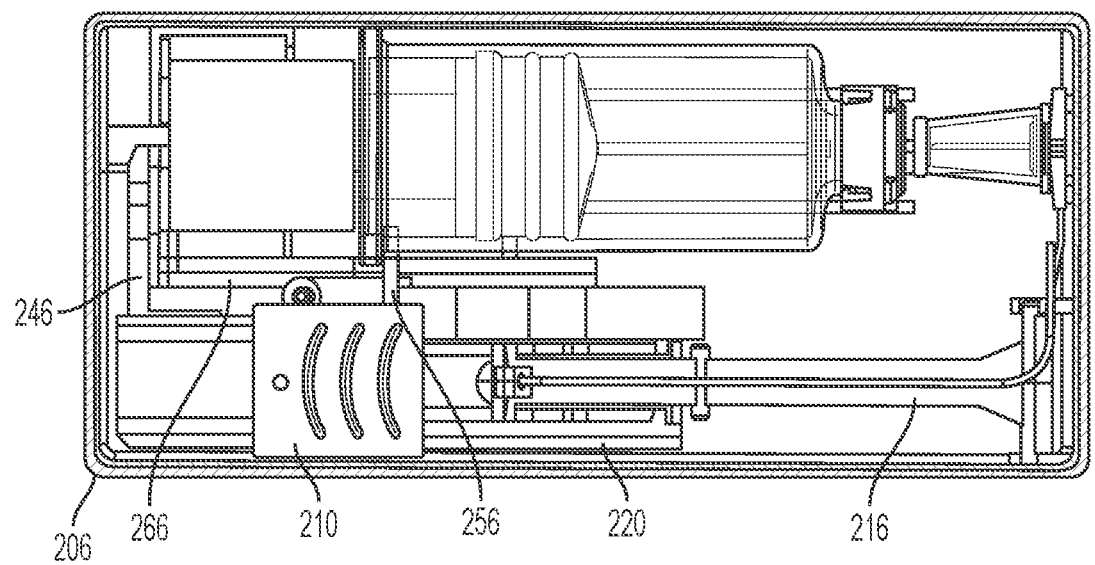
FIG. 48 is a top view of the drive assembly of FIG. 41 according to one aspect of the present invention, showing the drive assembly in an initial actuation position.

As shown in FIGS. 45-47, the spacer 226 is selected from a plurality of different size spacers 226 to occupy space from a proximal end of the stopper 224 to a proximal end of the container 222. The spacer 226 is substantially flush with the proximal end of the container 222. Additionally, the spacer 226 has a "top hat" shape, which includes a central column 230 and a distal flange 232, as best shown in FIG. 45.

Returning to FIGS. 44-47, the system 200 also includes a drive assembly 234 for displacing the container 222 distally to establish the fluid connection between the container 222 and the patient needle 215, as well as dispensing the medicament from the container 222. In more detail, the drive assembly 234 includes an inner spring 236 disposed within a central plunger 238, an outer plunger 240, an outer spring 242 disposed between the central plunger 238 and the outer plunger 240, a telescoping member 244, and a release gate 246.

Preferably, the inner spring 236 has a greater spring constant than the outer spring 242, and is therefore, stronger or stiffer than the outer spring 242. The inner spring 236 is disposed inside the central plunger 238, and pushes between a spring flange 248 in the lower housing (best shown in FIG. 46) and the central plunger 238, which bears directly on the proximal end of the spacer 226 subsequent to device activation. The outer spring 242 is disposed inside outer plunger 240, and pushes between a proximal external flange 250 of the central plunger 238 and a distal internal flange 252 of the outer plunger 240. Thus, the inner and outer springs 236 and 242 are nested, and can provide a more compact drive assembly (and thus, a more compact system 200) than employing a single spring.

According to one aspect, the inner spring 236 acts only to displace the container 222 to establish the fluid connection with the patient needle 215, and the outer spring 242 acts only to subsequently dispense the medicament from the container 222. According to another aspect, the inner spring 236 acts to displace the container 222 to establish the fluid connection with the patient needle 215, and also acts to begin dispensing the medicament from the container 222, and the outer spring 242 acts to complete dispensing the medicament. In a further aspect, the inner spring 236 causes the initial piercing of the container 222 with the outer spring 242 completing the piercing and dispensing of the medicament from the container 222.

As shown in FIGS. 44-47, and as subsequently described in greater detail, the outer plunger 240 includes a pair of proximal flanges or feet 254 that each have a slanted surface that interacts with a corresponding slanted surface (or surfaces) on the release gate to retain and subsequently release the power module subsequent to actuation of the device 200.

As best shown in FIGS. 46 and 47, as initially assembled, the container 222 is disposed in clearance from the drive assembly 234 and the valve assembly 212. A lateral flange 256 on the needle actuator 220 axially retains the medicament container 222, and the needle actuator 220 prevents the release gate 246 from displacing laterally. According to one embodiment, a spring (not shown) biases the needle actuator 220 distally, but the actuation button 210 (and/or its associated assembly) prevents distal displacement of the needle actuator 220 prior to actuation of the device 200. A status bar 258 is disposed on the needle actuator 220, and has a top surface that is visible through the status view port 208. According to one embodiment, the top surface of the status bar has a plurality of colors or patterns, and when the device is in a pre-actuated state, a first color or pattern, such as yellow, is visible through the status view port 208.

Figure 49:
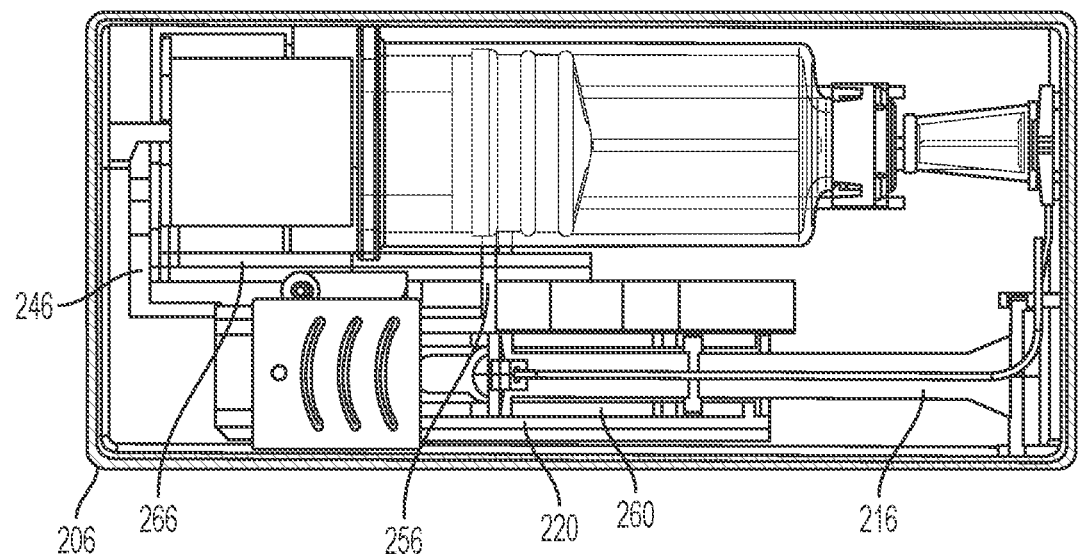
FIG. 49 is a top view of the drive assembly of FIG. 41 according to one aspect of the present invention, showing the drive assembly in an initial actuation position.

FIGS. 48-52 are top views of the system 200 illustrating the operation of events at and subsequent to actuation of the system 200. In FIG. 47, a user slides the actuation button 210 proximally and then displaces the button 210 vertically into the housing 202, thereby freeing the needle actuator 220 to displace distally under the influence of the spring (omitted for clarity). As shown in FIG. 49, as the needle actuator displaces distally, tracks 260 on the needle actuator 220 interact with lateral bosses 262 on the needle arm 216 to insert the patient needle 215. Preferably at this stage, the proximal end of the needle actuator 220 has not yet cleared the release gate 246, and thus, the drive assembly 234 has not yet been released. But the lateral flange 256 has displaced distally and therefore, the container 222 is unrestrained.

Figure 50:
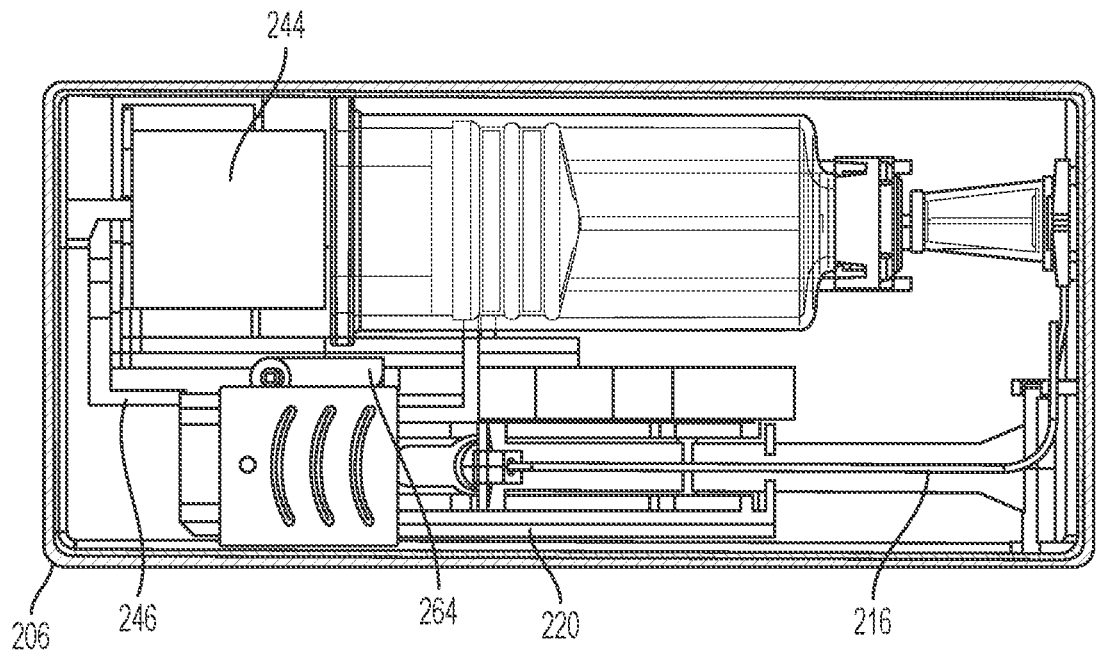
FIG. 50 is a top view of the drive assembly of FIG. 41 according to one aspect of the present invention, showing the drive assembly an initial actuation position.
Figure 51:
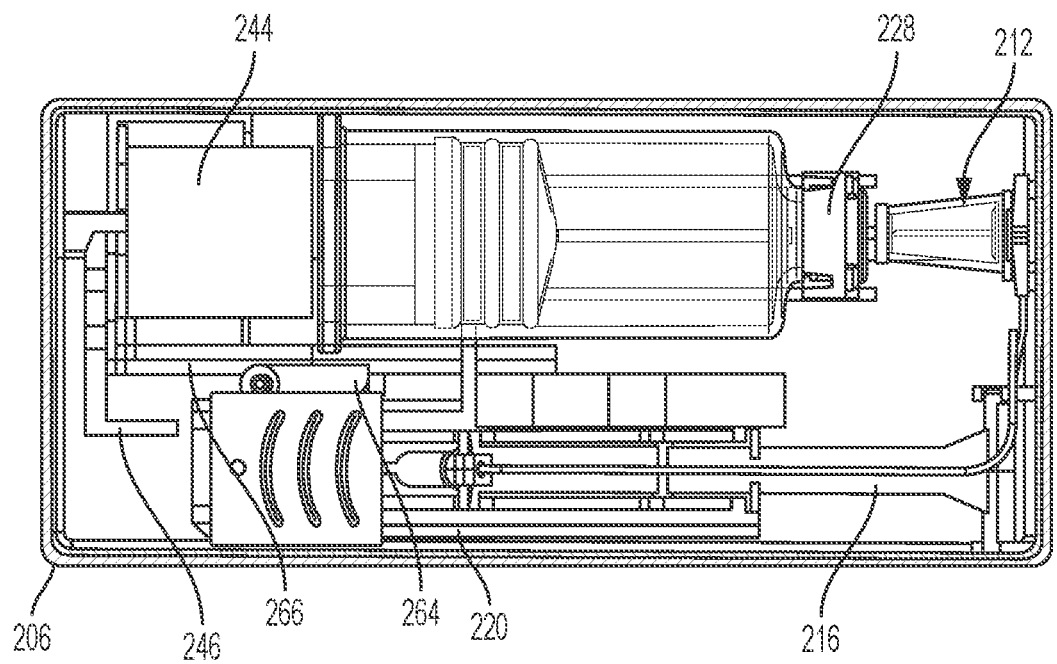
FIG. 51 is a top view of the drive assembly of FIG. 41 according to one aspect of the present invention, showing the drive assembly in a use position.

Subsequently, as shown in FIGS. 50 and 51, with continued distal displacement, the proximal end of the needle actuator 220 clears the release gate 246 (thereby releasing the drive assembly 234). The needle actuator 220 comes to temporarily rest against a feature on a rotatable release flipper 264, driving the release flipper 264 against an outrigger 266 (best shown in FIGS. 44 and 59) of the telescoping member 244. The needle actuator 220 remains in this position until the medicament has been dispensed. In this position, preferably, a second color or pattern of the status bar 258, such as green, is visible through the status view port 208.

At this stage, the force of the springs 236 and 242 and the interaction of the angled surfaces of the proximal flanges or feet 254 with the corresponding angled surface (or surfaces) on the release gate 246 causes the release gate 246 to displace laterally, thereby freeing the outer plunger 240 from restraining interaction with the release gate 246. Up to this point, the outer plunger 240 has been restraining the central plunger 238.

Figure 52:
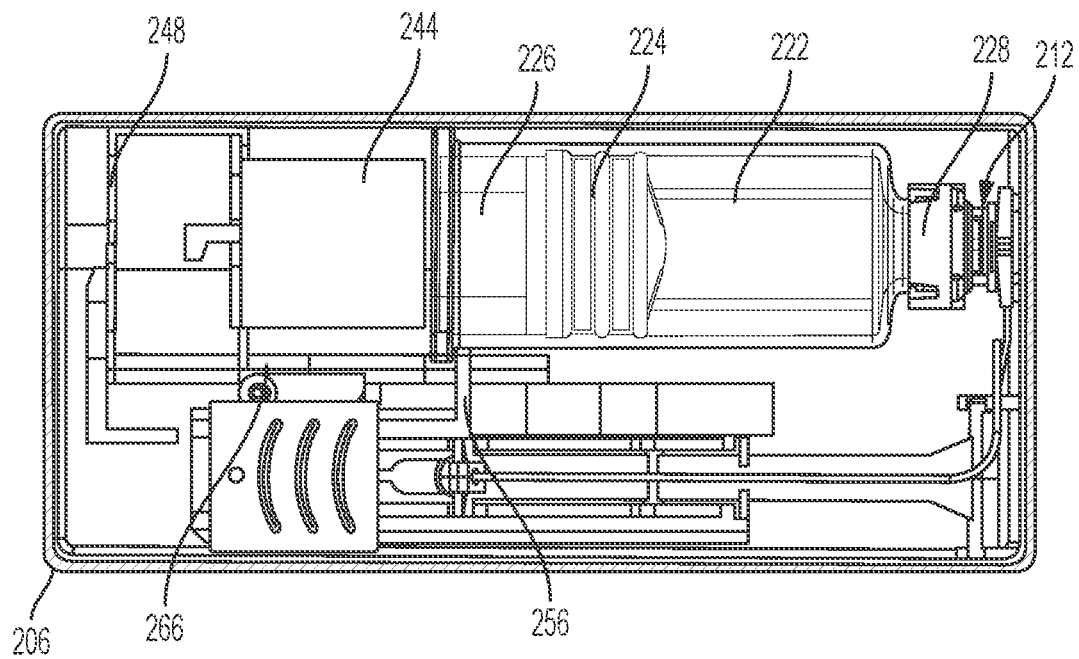
FIG. 52 is a top view of the drive assembly of FIG. 41 according to one aspect of the present invention, showing the drive assembly in a use position.
Figure 53:
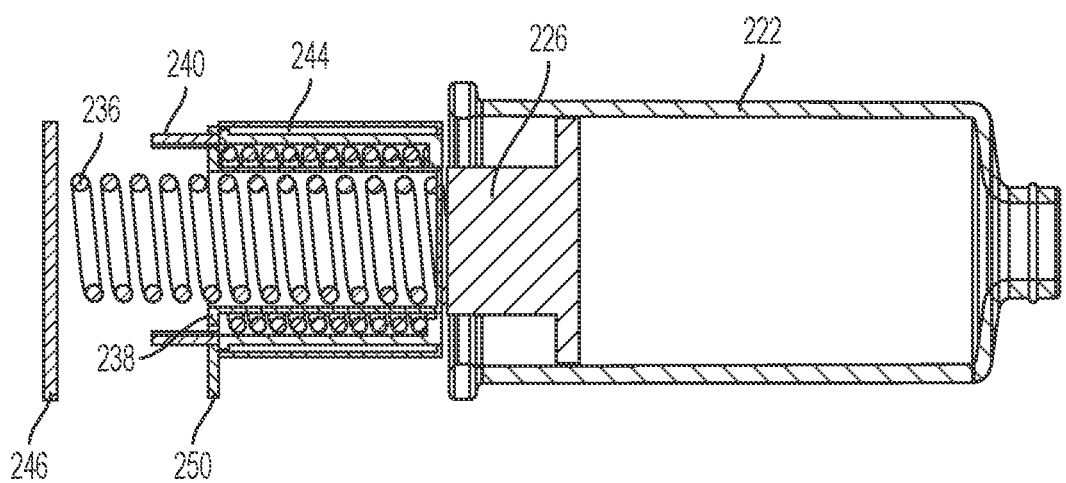
FIG. 53 is a cross-sectional view of the drive assembly of FIG. 41 according to one aspect of the present invention, showing the drive assembly in a use position.

Referring to FIGS. 52 and 53 (the inner spring 236 is omitted from FIG. 52 for clarity), the stiff inner spring 236 distally drives central plunger 238 to contact the spacer 226. Because the medicament container 222 is filled with a substantially incompressible fluid, the continued distal displacement of the central plunger 238 distally displaces the spacer 226, the stopper 224, and the container 222 relative to the housing 202. This distal displacement causes the septum assembly 228 to be pierced by the valve assembly 212, establishing fluid communication between the container 222 and the patient needle 215. The central plunger 238 travels distally until its proximal external flange 250 (best shown in FIG. 59) contacts a flange on the lower housing 206, thereby limiting the "piercing travel." Preferably, another flange on the lower housing 206 and/or the lateral flange 256 of the needle actuator 220 limits distal travel of the container 222.

Figure 54:
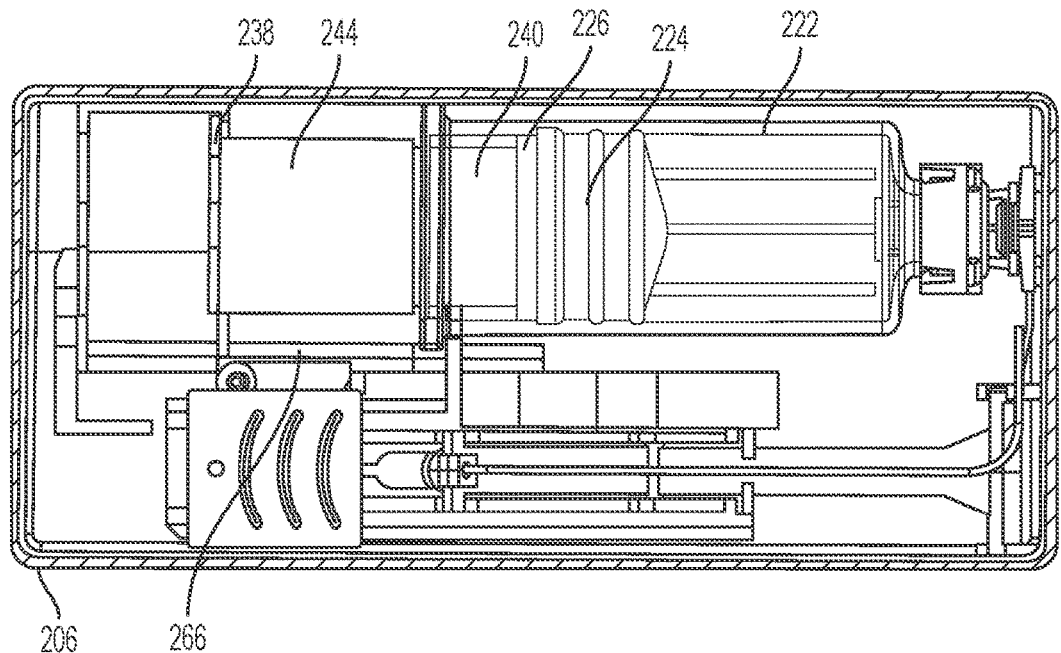
FIG. 54 is a top view of the drive assembly of FIG. 41 according to one aspect of the present invention, showing the drive assembly in a use position.
Figure 55:
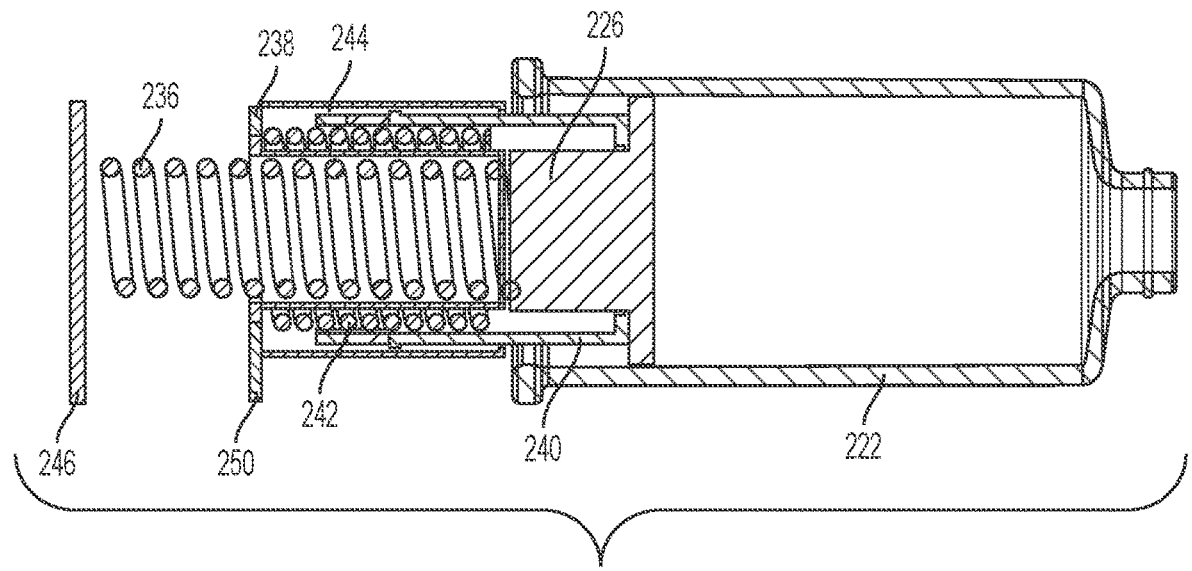
FIG. 55 is a cross-sectional view of the drive assembly of FIG. 41 according to one aspect of the present invention, showing the drive assembly in a use position.

Subsequently, because the inner spring 236 can no longer distally displace the central plunger 238, the lighter outer spring 242 distally displaces the outer plunger 240 relative to the central plunger 238 to contact the distal flange 232 of the spacer 226, as shown in FIGS. 54 and 55. As subsequently described in greater detail, preferably, the contact between the outer plunger 240 and the spacer 226 is damped to minimize the impact force. Further expansion of the outer spring 242 distally displaces the outer plunger 240 to dispense the medicament.

Figure 56:
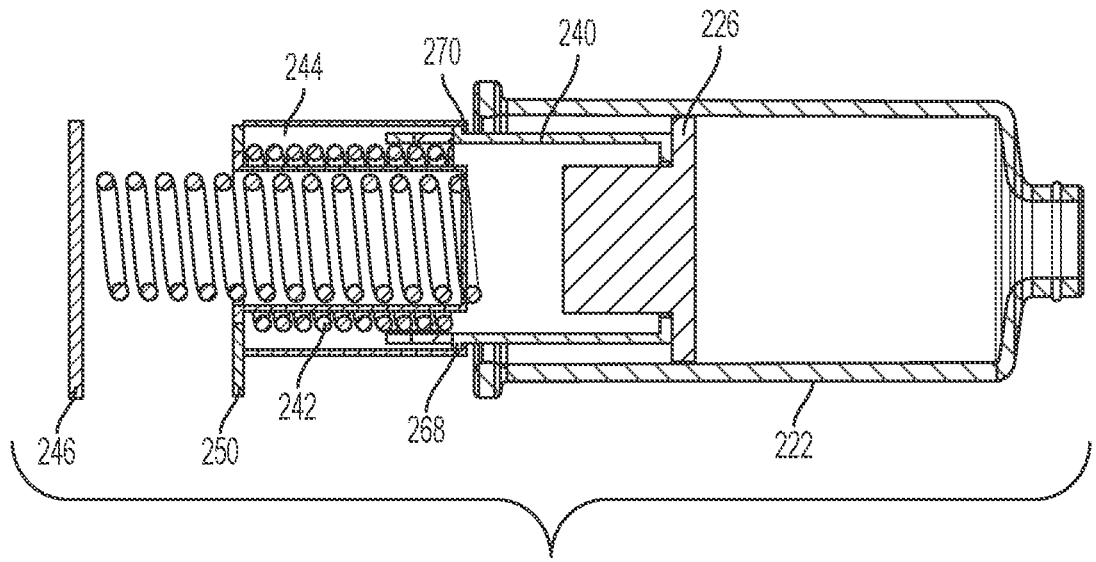
FIG. 56 is a cross-sectional view of the drive assembly of FIG. 41 according to one aspect of the present invention, showing the drive assembly in a use position.
Figure 57:
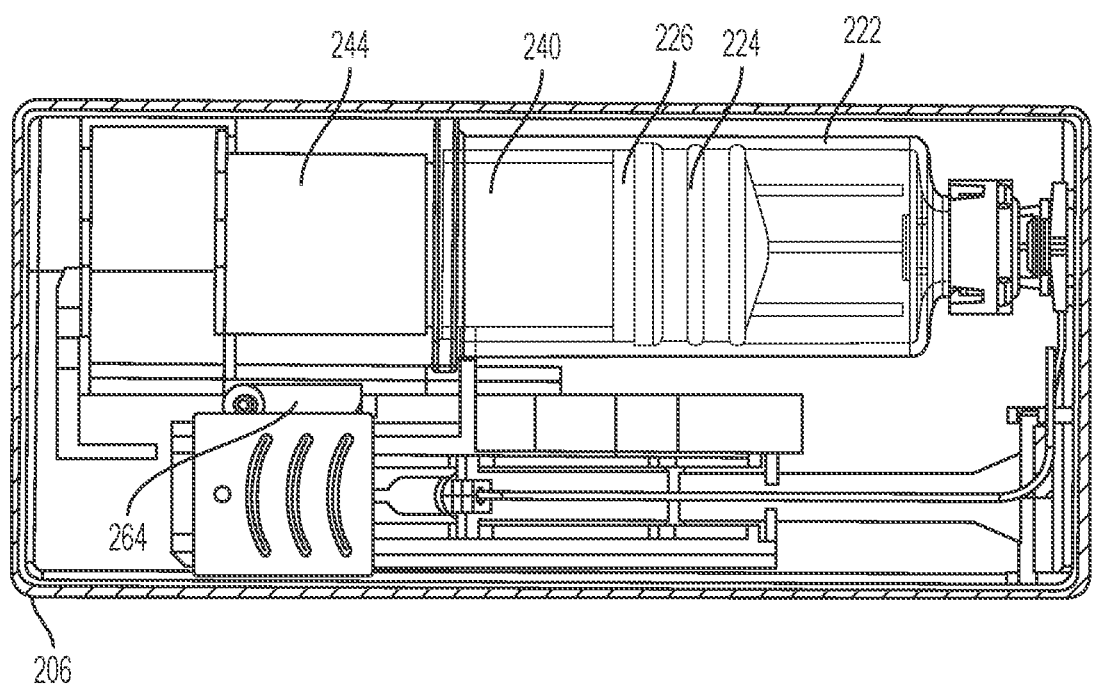
FIG. 57 is a top view of the drive assembly of FIG. 41 according to one aspect of the present invention, showing the drive assembly in a use position.

As shown in FIGS. 56 and 57, as the outer spring 242 continues to expand and distally displace the outer plunger 240, upon a predetermined distal displacement of the outer plunger 240 relative to the telescoping member 244, an external feature or flange 268 of the outer plunger 240 interacts with an internal distal feature or flange 270 of the telescoping member 244 to "pick up" the telescoping member 244. This ensures that further distal displacement of the outer plunger 240 causes corresponding distal displacement of the telescoping member 244. This paired distal displacement continues until the end of the medicament dispensing.

Figure 58:
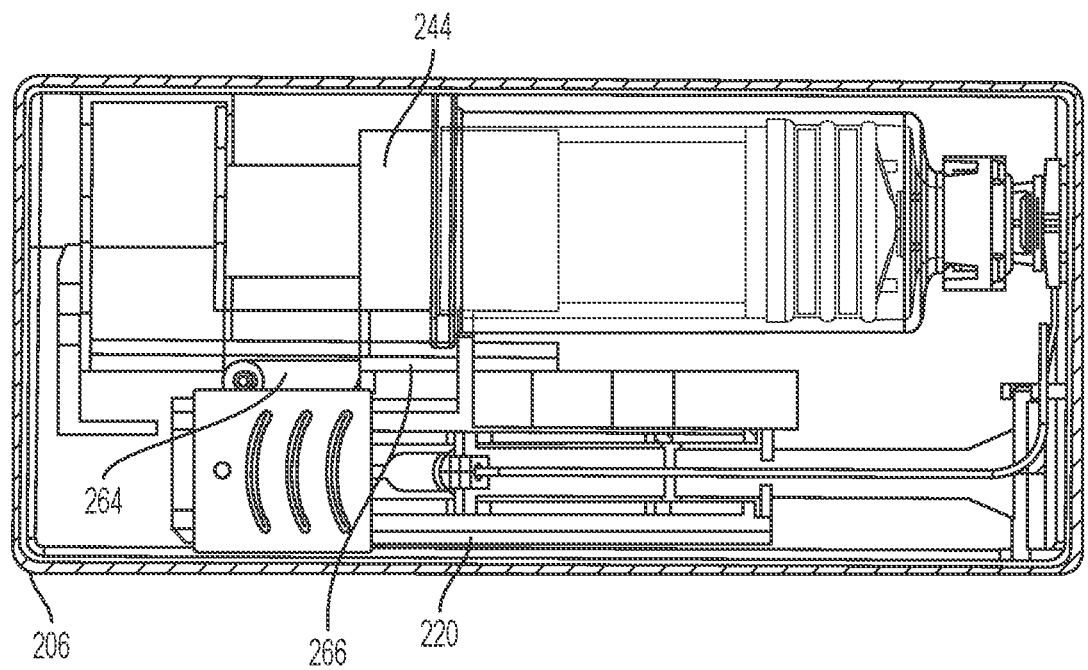
FIG. 58 is a top view of the drive assembly of FIG. 41 according to one aspect of the present invention, showing the drive assembly in an initial post-use position.
Figure 59:
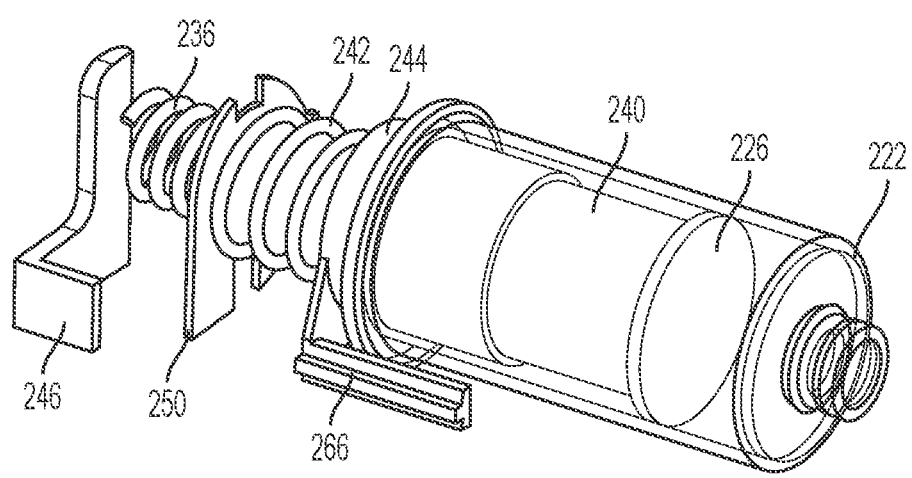
FIG. 59 is a perspective view of the drive assembly of FIG. 41 according to one aspect of the present invention, showing the drive assembly in an initial post-use position.
Figure 60:
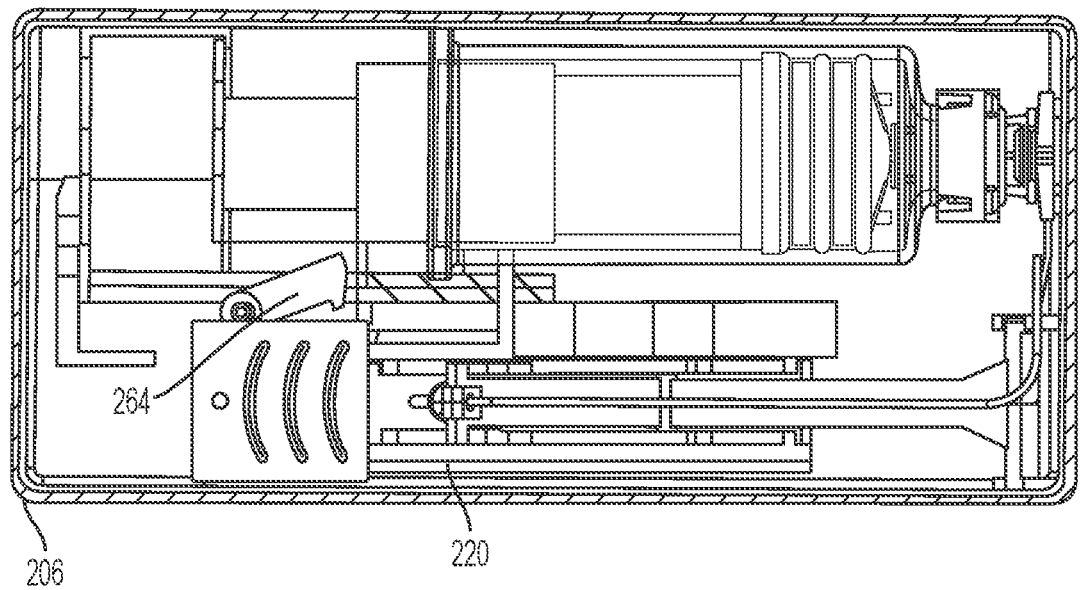
FIG. 60 is a top view of the drive assembly of FIG. 41 according to one aspect of the present invention, showing the drive assembly in a post-use position.
Figure 61:
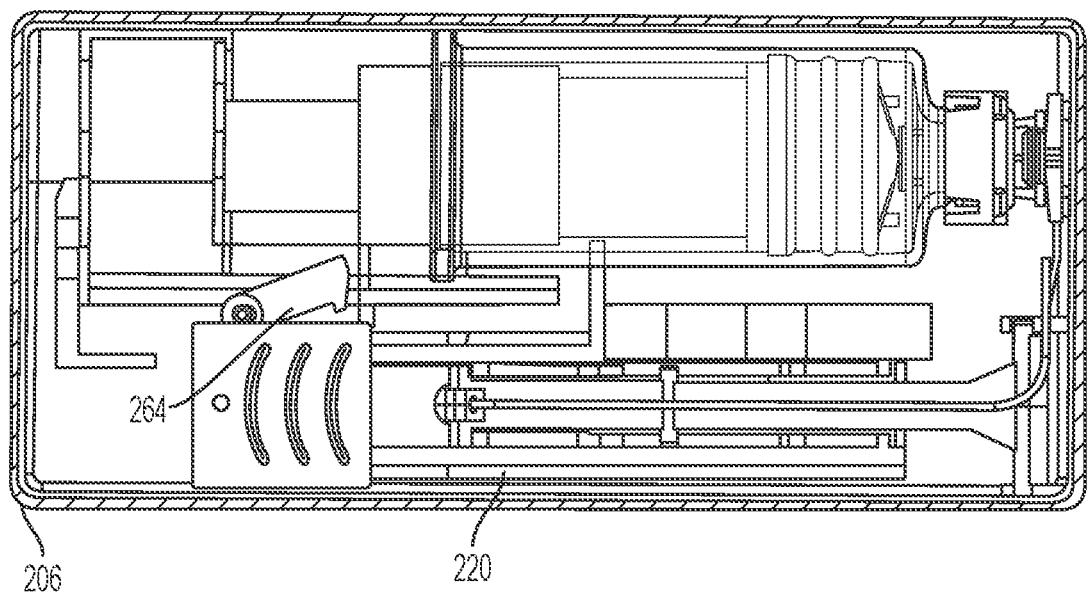
FIG. 61 top view of the drive assembly of FIG. 41 according to one aspect of the present invention, showing the drive assembly in a post-use position.

As previously noted, the outrigger 266 is disposed on the telescoping member 244. The axial length of the outrigger and the distal travel of the telescoping member 144 controls the timing of the disengagement of the outrigger 266 with the release flipper 264. As shown in FIGS. 58 and 59, at the end of medicament dispensing, the proximal end of the outrigger 266 bypasses the release flipper 264. This allows the release flipper 264 to rotate out of engagement with the needle actuator 220 (FIG. 60), and allows the needle actuator 220 to continue its distal displacement and withdraw the patient needle 215 (FIG. 61). At this stage, another color or pattern of the status bar 258, such as red, is visible through the status view port 208, signifying that the device 200 has completed operation.

Figure 62:
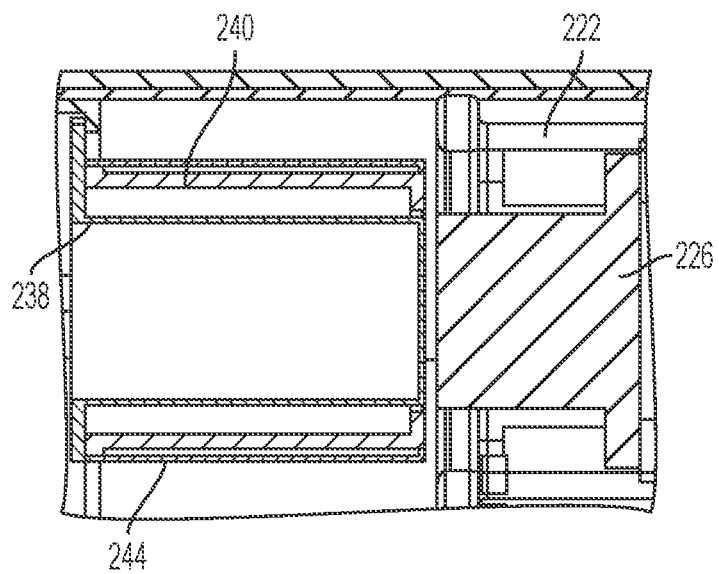
FIG. 62 is a cross-sectional view of the drive assembly of FIG. 41 according to one aspect of the present invention, showing the drive assembly in a pre-use position.
Figure 63:
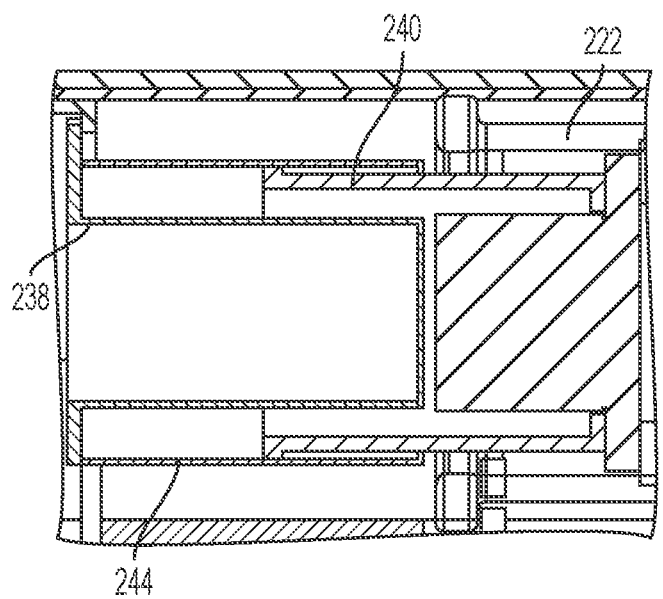
FIG. 63 is a cross-sectional view of the drive assembly of FIG. 41 according to one aspect of the present invention, showing the drive assembly in a use position.

As previously noted, the contact between the outer plunger 240 and the spacer 226, as illustrated in FIGS. 62 and 63, is preferably damped to minimize the impact force. The highest level of energy dissipation is desirable for under-filled syringes containing viscous fluid, as the outer spring 242 will be stiffer to provide desired dispense rates. The lowest level of energy dissipation is desirable for maximum-filled syringes containing low-viscosity fluid, as the outer spring can be less stiff to provide desired dispense rates. Various methods can be employed to adjust damping levels, such as air damping, or closed-cell foam damping.

Figure 64:
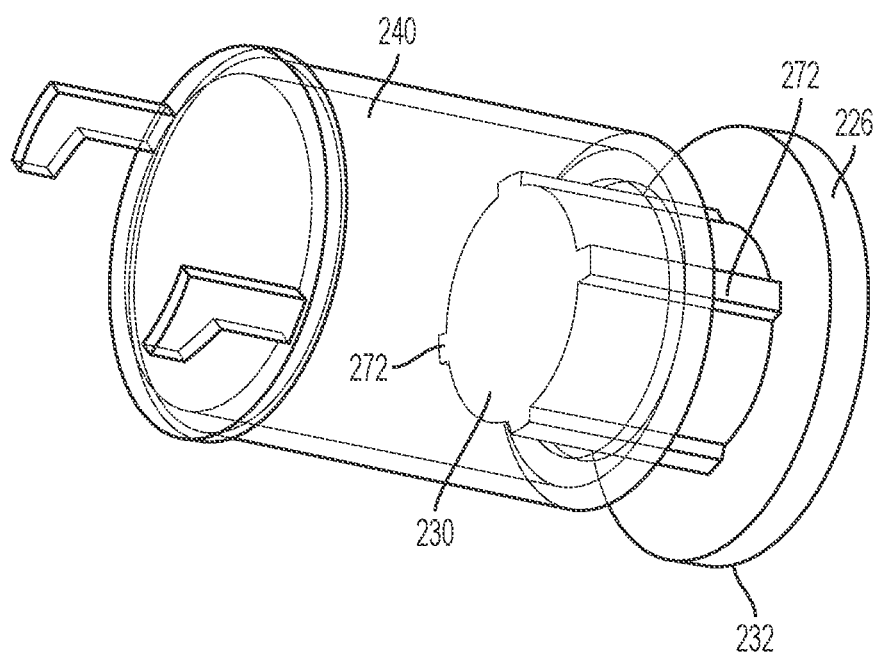
FIG. 64 is a perspective view of a drive assembly according to a further aspect of the present invention.

As another method of damping the impact force, FIG. 64 illustrates an embodiment of a spacer 226 in which one or more axial interface ribs 272 are circumferentially arrayed about the central column 230 of the spacer 226. In this embodiment, the outer plunger 240 must drive past the interference ribs 272, which provide frictional resistance to the distal displacement of the outer plunger 240 relative to the spacer 226. The frictional force created by the interference between interference ribs 272 and the outer plunger 240 is independent of plunger speed. Preferably, the frictional force does not exceed the minimum dispense spring load, to avoid stalling weaker springs. The interference can be tuned to give the desired level of frictional resistance. For different fluid viscosities, there can be different sizing (axial and/or radial) of the interference ribs 272. This could mean a bespoke or custom spacer for each viscosity and fill-level combination, or, depending on the number of springs required for a viscosity range, there can be a number of tined positions, whereby the spacer can be set to a particular position for a particular modular spring (the position have had the interference/damping tuned for that particular spring load/viscosity scenario).

Figure 65A:
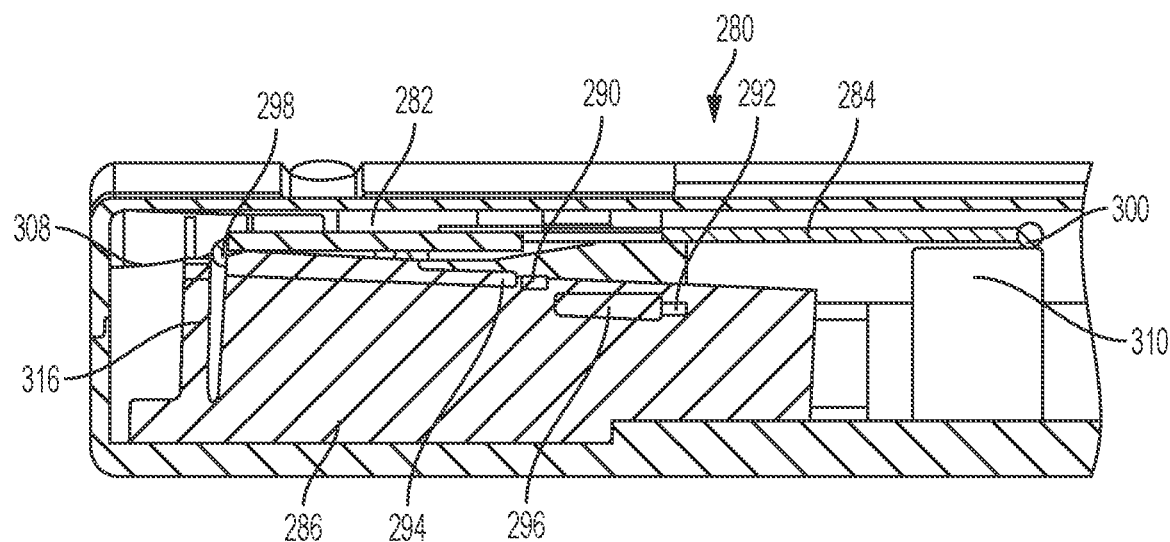
FIG. 65A is a front view of a needle actuator assembly according to one aspect of the present invention, showing the needle actuator assembly in a use position.
Figure 65B:
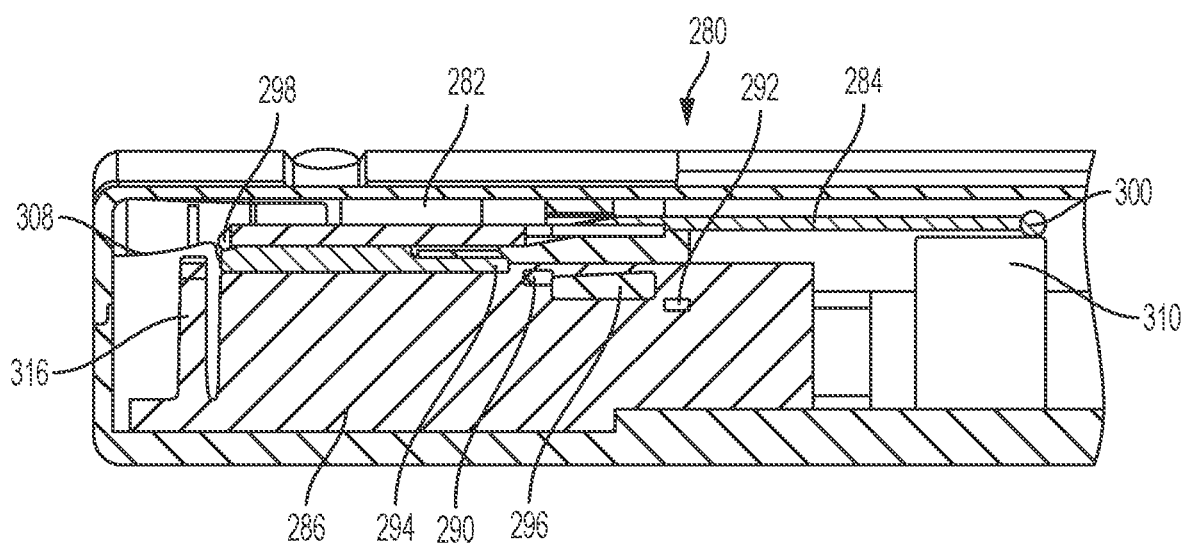
FIG. 65B is a front view of the needle actuator assembly of FIG. 65A according to one aspect of the present invention, showing the needle actuator assembly in a use position.
Figure 65C:
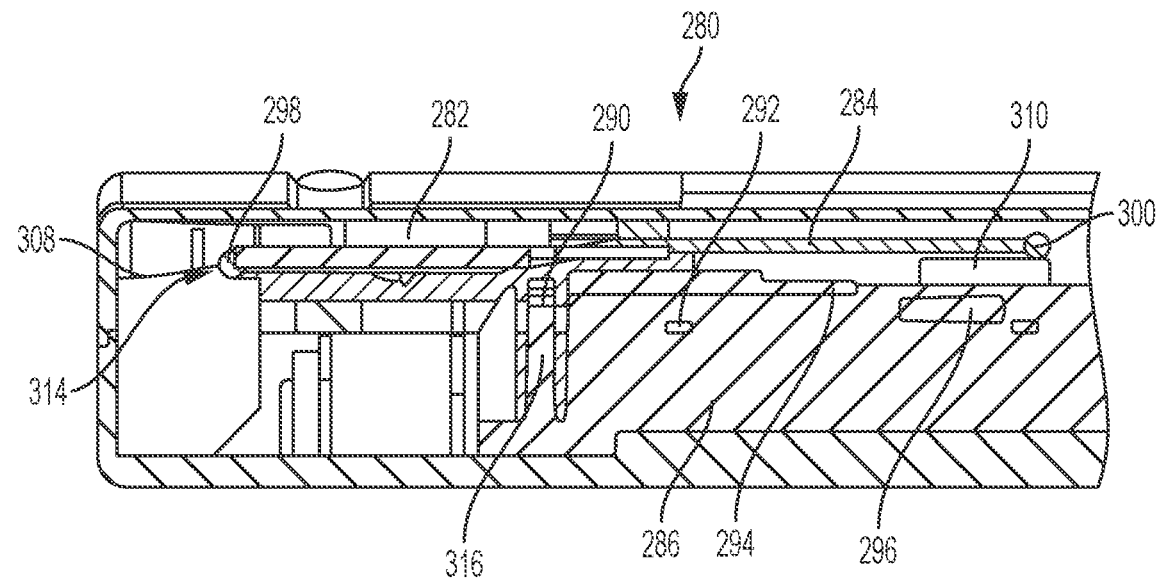
FIG. 65C is a front view of the needle actuator assembly of FIG. 65A according to one aspect of the present invention, showing the needle actuator assembly in an initial post-use position.
Figure 65D:
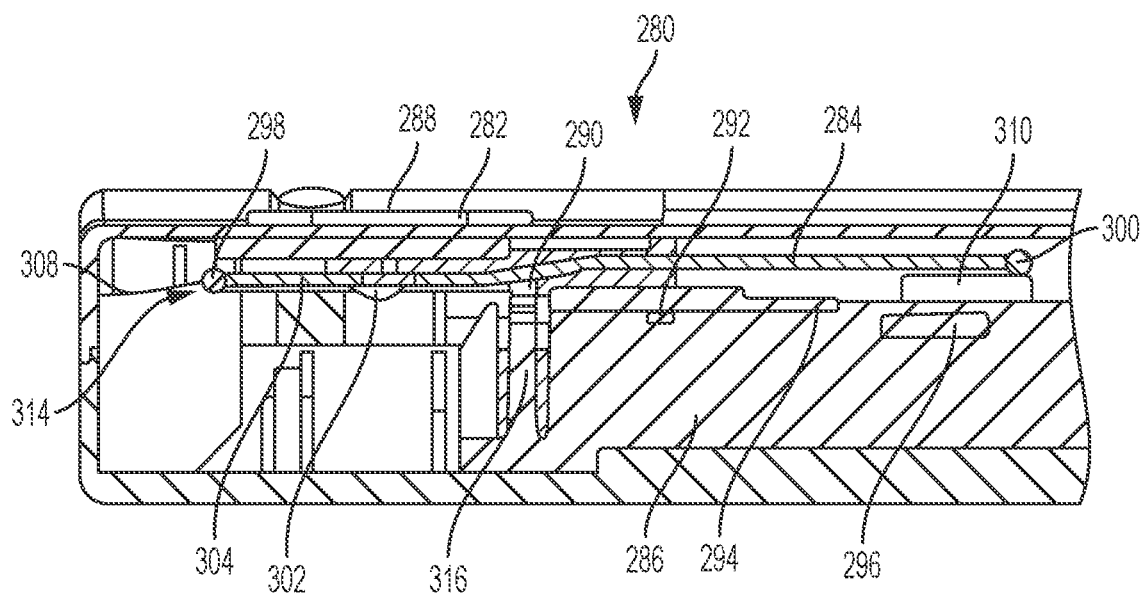
FIG. 65D is a front view of the needle actuator assembly of FIG. 65A according to one aspect of the present invention, showing the needle actuator assembly in a post-use position.
Figure 65E:
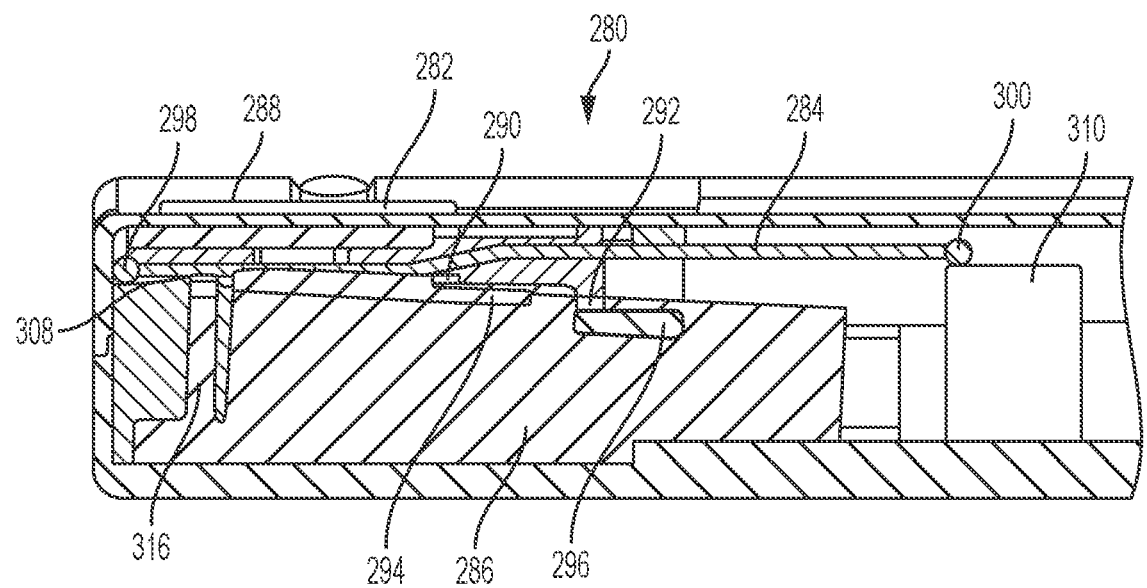
FIG. 65E is a front view of the needle actuator assembly of FIG. 65A according to one aspect of the present invention, showing the needle actuator assembly in a pre-use position.
Figure 65F:
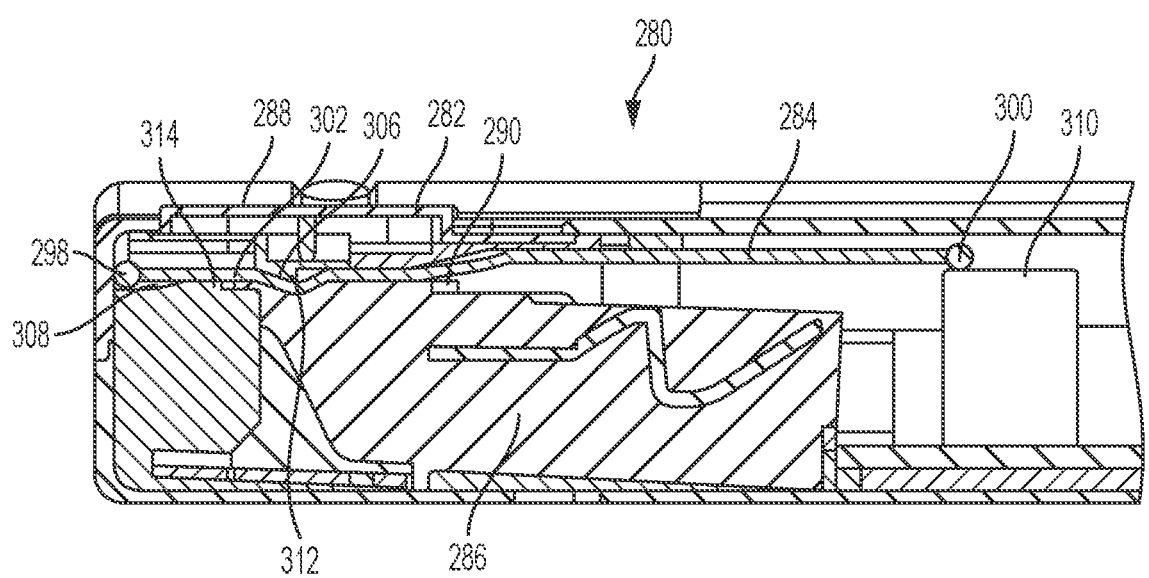
FIG. 65F is a cross-sectional view of the needle actuator assembly of FIG. 65A according to one aspect of the present invention, showing the needle actuator assembly in a pre-use position.
Figure 65G:
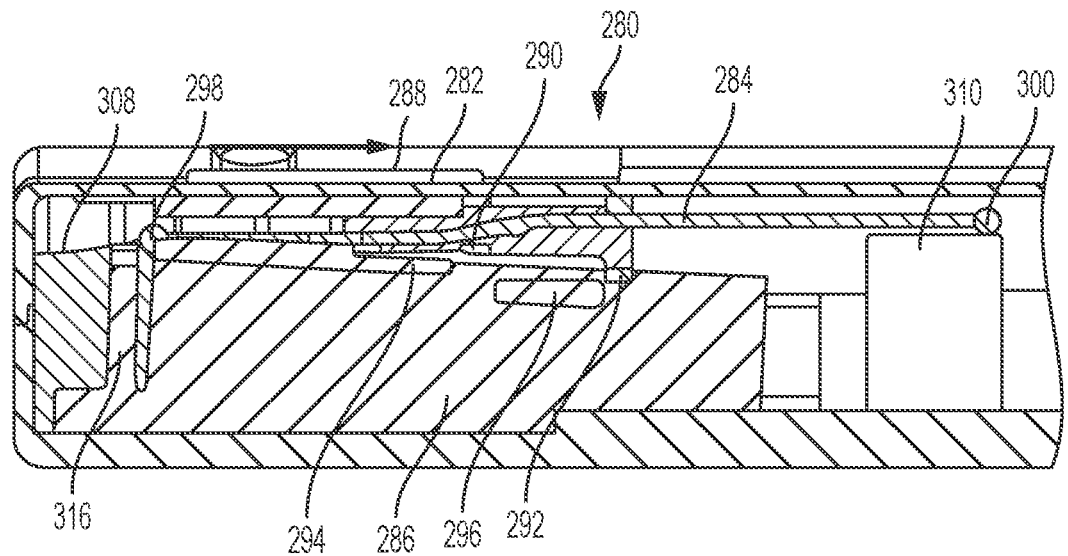
FIG. 65G is a front view of the needle actuator assembly of FIG. 65A according to one aspect of the present invention, showing the needle actuator assembly in a pre-use position with a button actuator axially displaced.
Figure 65H:
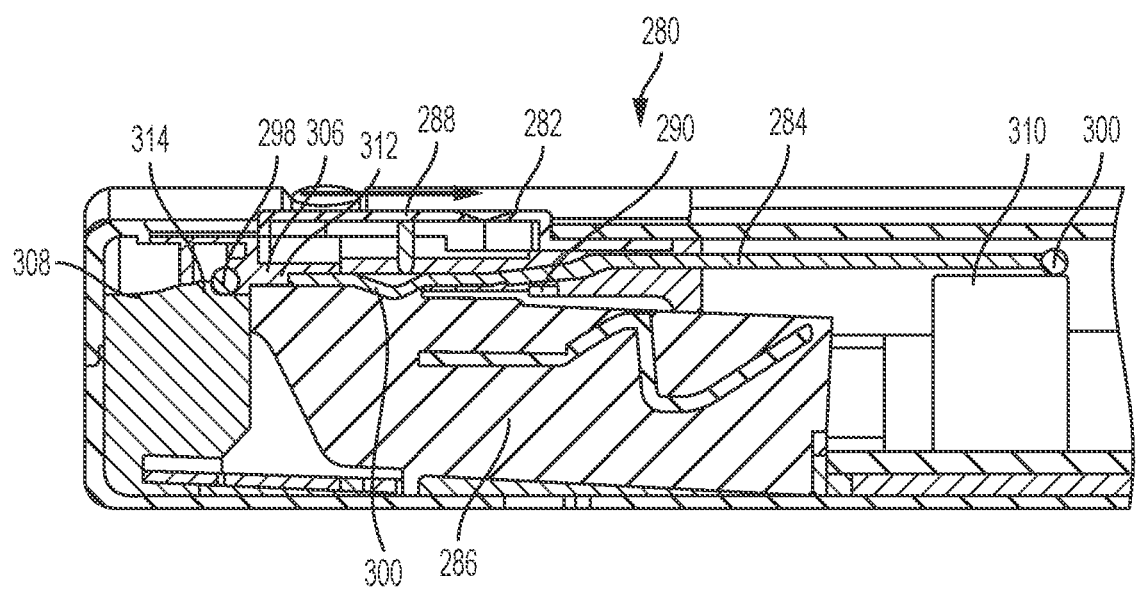
FIG. 65H is a cross-sectional view of the needle actuator assembly of FIG. 65A according to one aspect of the present invention, showing the needle actuator assembly in a pre-use position with a button actuator axially displaced.
Figure 66:
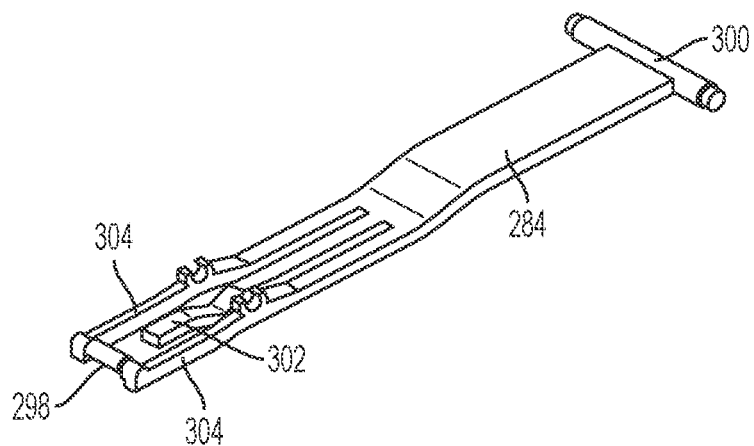
FIG. 66 is a perspective view of a button spring of the needle actuator assembly of FIG. 65A according to one aspect of the present invention.
Figure 67:
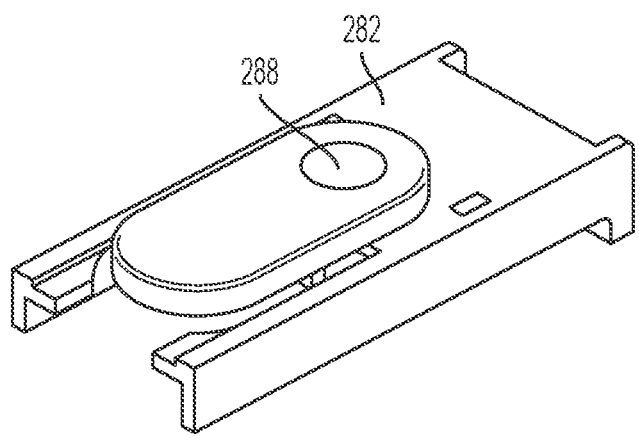
FIG. 67 is a perspective view of an actuator button of the needle actuator assembly of FIG. 65A according to one aspect of the present invention.
Figure 68A:
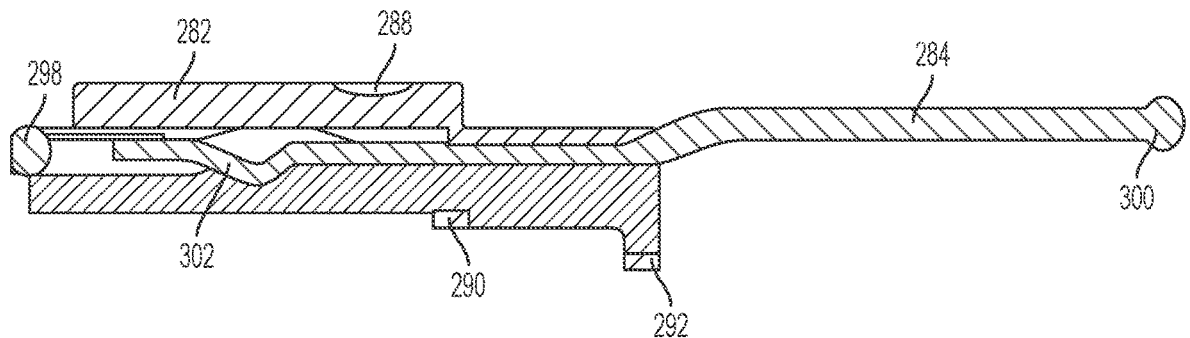
FIG. 68A is a cross-sectional view of a button spring and actuator button of the needle actuator assembly of FIG. 65A according to one aspect of the present invention.
Figure 68B:
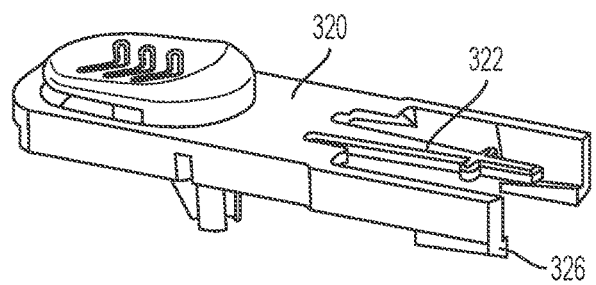
FIG. 68B is a perspective view of an actuator button of the needle actuator assembly of FIG. 65A according to a further aspect of the present invention.
Figure 68C:
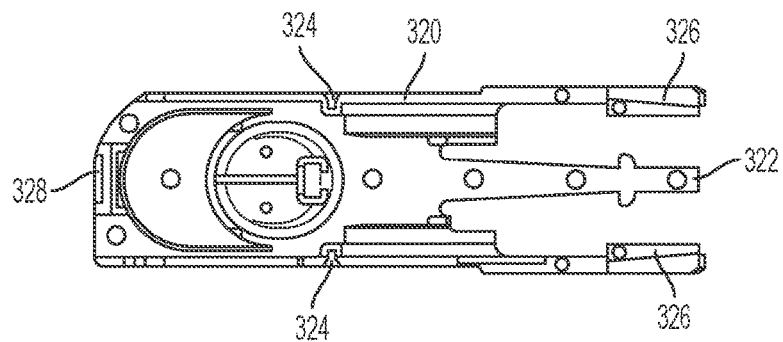
FIG. 68C is a bottom view of an actuator button of the needle actuator assembly of FIG. 65A according to a further aspect of the present invention.
Figure 68D:
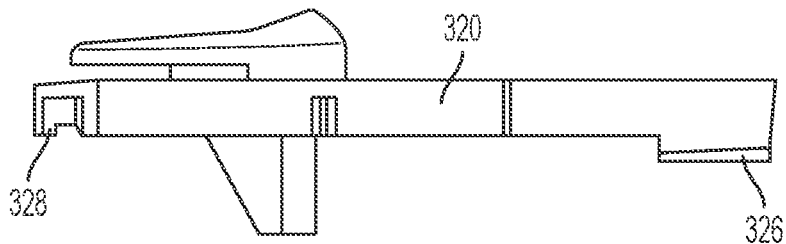
FIG. 68D is a front view of an actuator button of the needle actuator assembly of FIG. 65A according to a further aspect of the present invention.
Figure 68E:
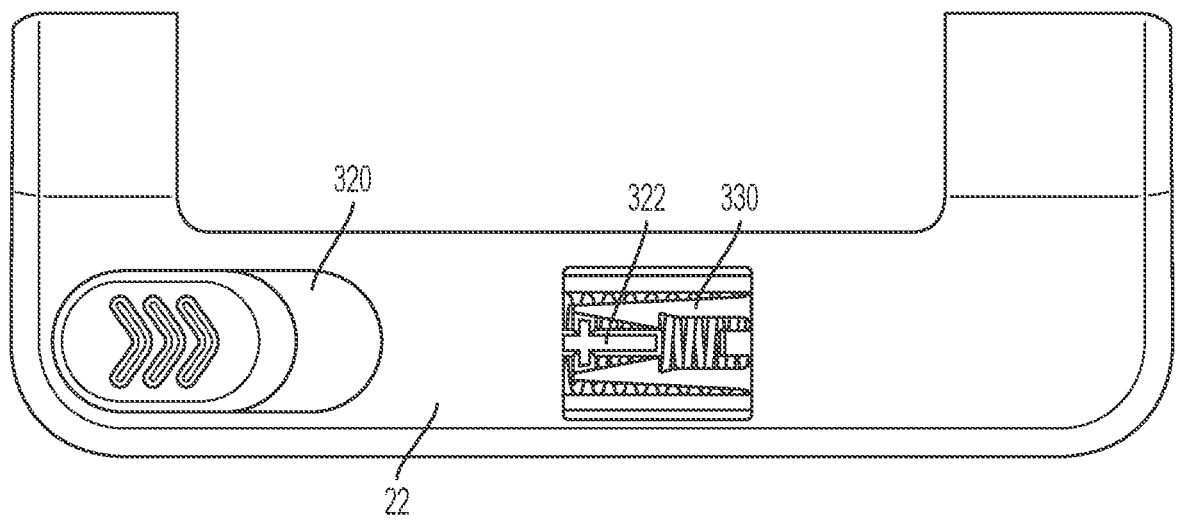
FIG. 68E is a top view of an actuator button of the needle actuator assembly of FIG. 65A according to a further aspect of the present invention, showing the actuator button in a pre-use position.
Figure 68F:
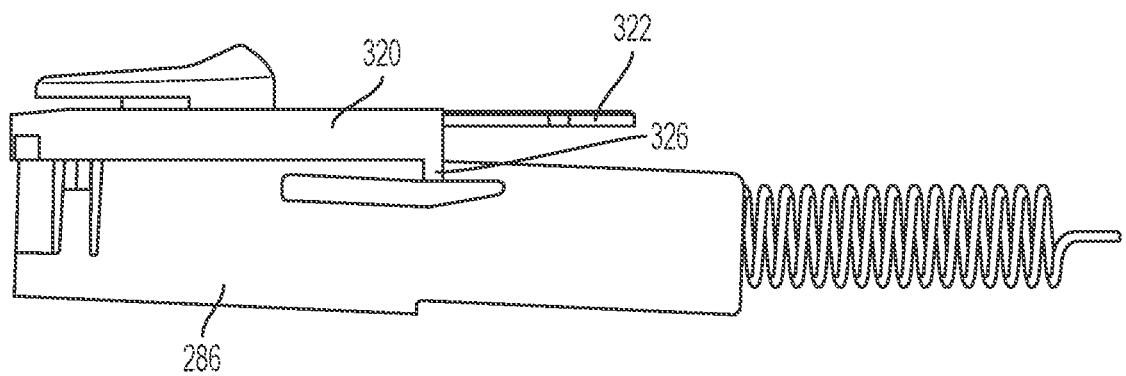
FIG. 68F is a front view of an actuator button of the needle actuator assembly of FIG. 65A according to a further aspect of the present invention, showing the actuator button in a pre-use position.
Figure 68G:
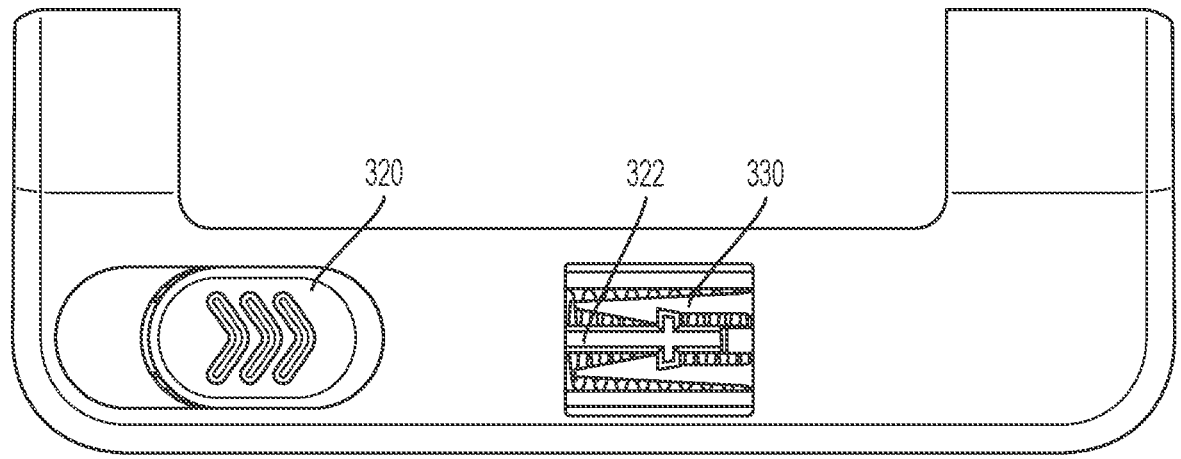
FIG. 68G is a top view of an actuator button of the needle actuator assembly of FIG. 65A according to a further aspect of the present invention, showing the actuator button in a use position.
Figure 68H:
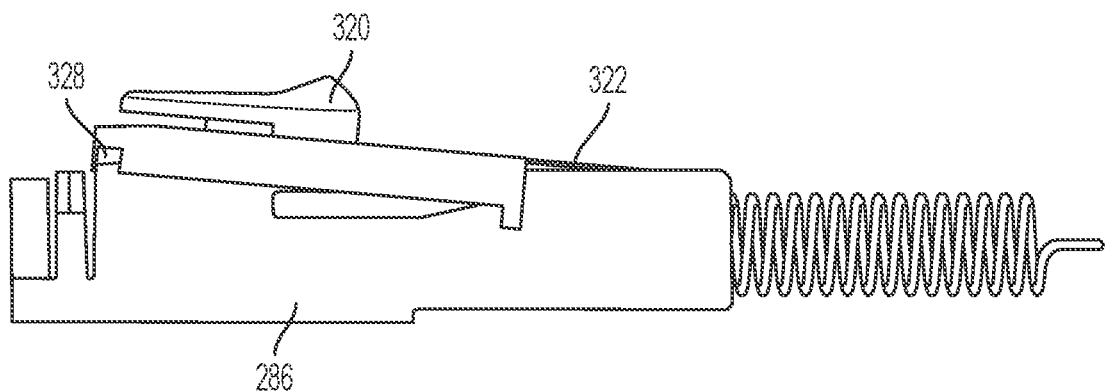
FIG. 68H is a front view of an actuator button of the needle actuator assembly of FIG. 65A according to a further aspect of the present invention, showing the actuator button in a use position.
Figure 69:
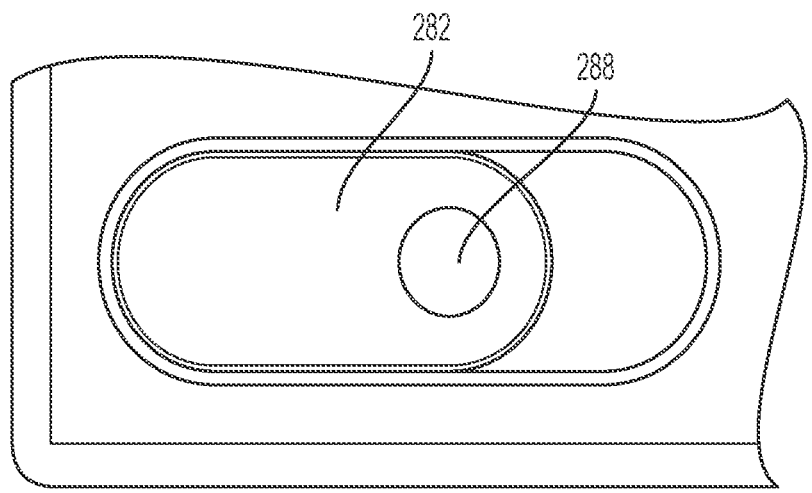
FIG. 69 is a top view of an actuator button of the needle actuator assembly of FIG. 65A according to one aspect of the present invention.

Referring to FIGS. 65A-69, an actuator button arrangement 280 for actuating the system 10 according to one aspect of the present invention is shown. The actuator button arrangement 280 includes the actuator button 26, a button spring 284, and a needle actuator body 286. The needle actuator body 286 may be similar to the needle actuator bodies 96, 220 discussed above and configured to move within the housing 20 to transition the needle shuttle 102 or needle 28 between retracted and extended positions. As shown in FIG. 69, the actuator button 26 includes a user interface portion 288 for interacting with a user. Preferably, the user interface portion 288 is about 22 mm long and about 10 mm wide, although other suitable dimensions may be utilized. The actuator button 26 includes two pairs of lockout arms 290, 292 that interact with button contacting surfaces 294, 296 on the needle actuator body 286 prior to device actuation to prevent the needle actuator body 286 from rocking upward. As shown in FIG. 65H, an overlap between the needle actuator body 286 and the housing 20 prevents premature actuation. Referring to FIG. 66, the button spring 284 includes a first bearing surface 298 and a second bearing surface 300 spaced from the first bearing surface 298, and a cantilevered central spring arm 302 surrounded by a pair of outer arms 304 that are joined by the first bearing surface 298.

The actuation button arrangement 280 is configured to provide one or more of the following features, which are discussed in more detail below: one-way axial displacement or sliding of the actuator button 26; transverse movement (raised and depressed positions) of the actuator button 26 where the actuator button 26 remains depressed during the use position of the needle actuator body 286; and lockout of the actuator button 26 in the post-use position of the needle actuator body 286 such that the button 26 is in the raised position and cannot be depressed by a user.

To actuate the system 10 using the actuator button 26, the user first slides the user interface portion 288 in a first axial direction, shown as being to the right in FIGS. 65G and 65H. The user may be required to slide the user interface portion 288 about 10 mm or about 8 mm, although other suitable distances may be utilized. Moving the actuator button 26 axially moves the lockout arms 290, 292 to clear the button contact surfaces 294, 296 on the needle actuator body 286 to allow movement of the actuator button 26 from the raised position to the depressed position.

As the user distally slides the user interface portion 288, the central spring arm 302 of the button spring 284 rides over a spring arm 306 bearing surface on the housing 20 while the first and second bearing surfaces 298, 300 engage first and second bearing ramps 308, 310 on the housing 20. The forces on the button spring 284 are balanced through the engagement with the spring arm bearing surface 306 and the first and second bearing ramps 308, 310 to provide a smooth axial displacement or sliding of the actuator button 26.

As the actuator button 26 and the button spring 284 reach the end of their axial sliding travel, the central spring arm 302 and the first bearing surface 298 pass the end of a respective stops 312, 314 to prevent the actuator button 26 from sliding backward to its original position, as shown in FIG. 65H. Further, when the actuator button 26 and the button spring 284 reach the end of their axial sliding travel, the user engages the user interface portion 288 to move the actuator button 26 downward to its depressed position. The actuator button 26 may be depressed about 2 mm and the minimum force required to depress the actuator button 26 is about 3 N, and most preferably, about 2.8 N, although other suitable distances and minimum forces may be utilized.

As the user depresses the user interface portion 288, shown in FIGS. 65A and 65B, the actuator button 26 rotates the needle actuator body 286 to release the needle actuator body 286 thereby allowing the needle actuator body 286 to move from the pre-use position to the use position. As shown in FIG. 65B, as the needle actuator body 286 travels to the use position, the lockout arms 290, 292 run along the underside of the button contact surfaces 294, 296 to prevent the actuator button 26 springing upward. After the medicament has been delivered and as the needle actuator body 286 is transitioning from the use position to the post-use position, shown in FIG. 65C, the lockout arms 290, 292 are disengaged from the button contact surfaces 294, 296 allowing the actuator button 26 to spring back up under the influence of the button spring 284. Once the needle actuator body 286 fully transitions to the post-use position, shown in FIG. 65D, the actuator button 26 has finished moving from the depressed position to the raised position due to the biasing force of the button spring 284. When the needle actuator body 286 is in the post-use position, a spring arm 316 on the needle actuator body 286 engages the actuator button 26 to prevent the actuator button 26 from moving to the depressed position while axial movement is still restricted by the engagement of the spring arm 302 with the stops 312, 314. Thus, the actuator button 26 is locked after delivery of the medicament is complete to provide a clear indication between a used system and an unused system.

Furthermore, if the user holds down the actuator button 26 during dispensing of the medicament, proper dosing and needle retraction will still complete, but the actuator button 26 will not spring back up to the raised position until the button 26 is released.

In one aspect, the button spring 284 is made of plastic. The button spring 284 may also be a pressed metal spring could be used instead, although any other suitable material may be utilized.

Referring to FIGS. 68A-68G, rather than providing a separate actuator button 26 and button spring 284, the spring may be provided integrally with the button 26. More specifically, an actuator button 320 according to a further aspect of the present invention includes an integral spring arm 322. The actuator button 320 also includes lockout arms 324, retention arms 326, and a rear pivot 328. As shown in FIGS. 68D and 68E, the spring arm 322 engages prongs 330 in the top portion 22 of the housing 20. During transition of the system 10 from the pre-use position to the use position, the spring arm 322 slides past a detent of the prongs 330 providing an axial spring force. The end of the spring arm 322 engages a portion of the top portion 22 of the housing 20 to provide the vertical spring force as the spring arm 322 deflects. The actuator button 320 is configured to a fluid motion between the sliding and depression movements of the button 320 even though two separate motions are occurring, which is similar to the operation of the button 26 discussed above. During transition between the pre-use position and the use position, the button 320 pivots about the rear pivot 328 with the retention arm 326 engaging a portion of the needle actuator body 286 thereby maintaining a depressed position of the button 320 until the end-of-dose position is reached in a similar manner as actuator button 26. The lockout arms 324 deflect inwards and engages a portion of the needle actuator body 286 as the needle actuator body 286 moves to the end-of-dose position thereby preventing further movement of the actuator button 320 in a similar manner as the actuator button 26 discussed above.

Aspects of the present invention provide improvements over previous button designs. For example, the actuation button arrangement 280 provides multiple surfaces to hold the needle actuator body 286 in place against a needle actuator spring 106 prior to actuation, thereby reducing the likelihood of premature actuation during a drop impact. The actuation button arrangement 280 physically prevents the needle actuator body 286 from moving prior to actuation by holding it in a tilted (locked) state in such a way that the surfaces have no room to separate and pre-activate.

In addition, button slide forces of the actuation button arrangement 280 are controlled more precisely by utilizing a flexing arm rather than using a simple bump detent. This permits longer sliding strokes of the button 26 with better force control, resulting in a more ergonomically effective design. Further, the actuation button arrangement 280 causes the button 26 to pop back out at the end of injection, giving the user an additional visual, audible, and tactile indication that the medicament delivery is completed.

According to one aspect, the fluid delivery volume of the system 10 is determined by the end position of a plunger relative to a point inside the housing regardless of actual fill volume, container inner diameter, and stopper starting position and length. The dosing accuracy variability can be significant because the tolerances of the factors above can be quite large. Aspects of the present invention allow for the elimination of some or all of these tolerances from the dosing equation, resulting in a more precise and less variable injection volume of medicament.

Figure 70:
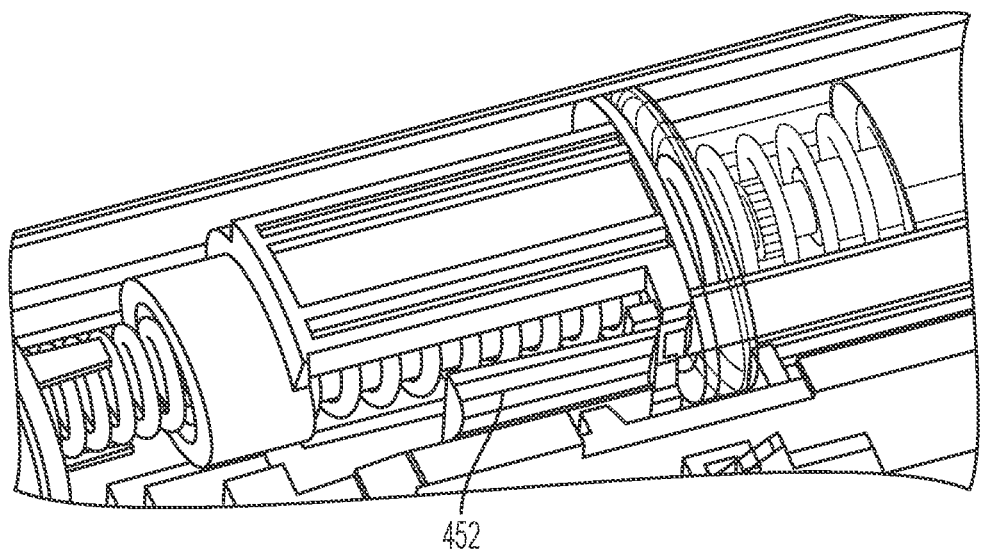
FIG. 70 is a perspective view of a restriction member according to one aspect of the present invention.
Figure 71:
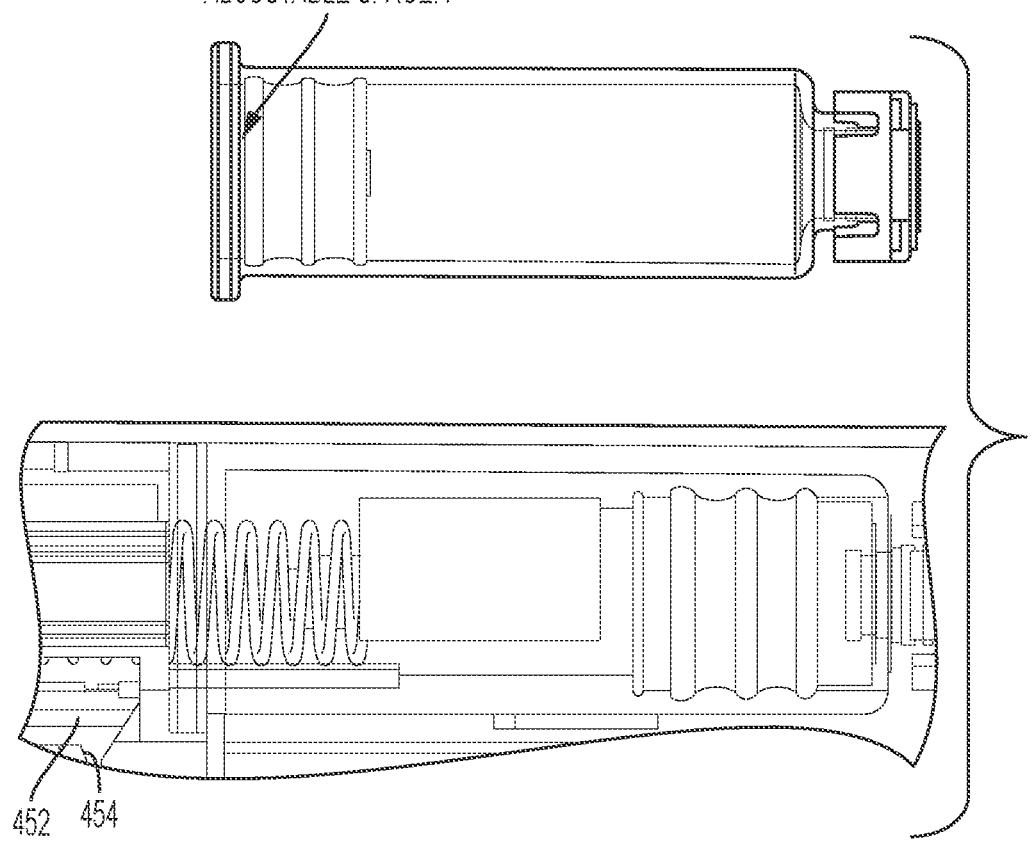
FIG. 71 is a front view of a spacer assembly for a drug delivery system according to a further aspect of the present invention.
Figure 72:
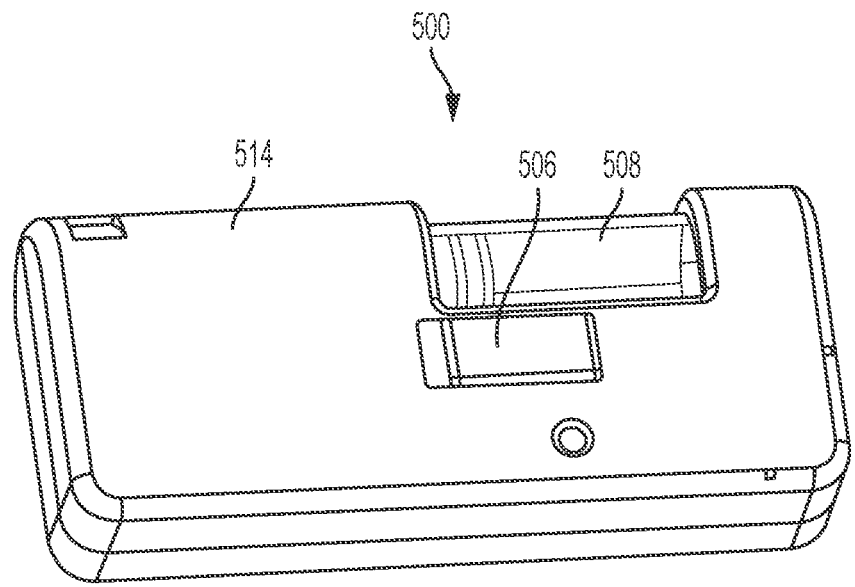
FIG. 72 is a perspective view of a drive assembly for a drug delivery system according to one aspect of the present invention.

Referring to FIGS. 69 and 70, a restriction member 452 according to one aspect of the present invention is disposed with the drive assembly. The restriction member 452 governs the timing of the final displacement of the needle actuator bodies 96, 220 subsequent to the completion of the medicament dose. Instead of rotating about a fixed post, the restriction member 452 floats freely. Once a plunger displaces sufficiently distally for a gap to align with the restriction member 452 (as shown in FIGS. 70 and 71), the restriction member 452 displaces laterally into the gap because of the force of the spring on the needle actuator 96, 220 and the angled face 454 on the rear of the arm of the restriction member 174 that engages the needle actuator body (best shown in FIG. 71). Once the restriction member no longer retains the needle actuator body 96, 220, the needle actuator body 96, 220 is free to complete the axial movement to the post-use position. Further, as shown in FIG. 71, the restriction member 452 is biased onto the rear of the barrel portion of the container 14, which minimizes the tolerance chain of the various components and improves dose accuracy.

Figure 73:
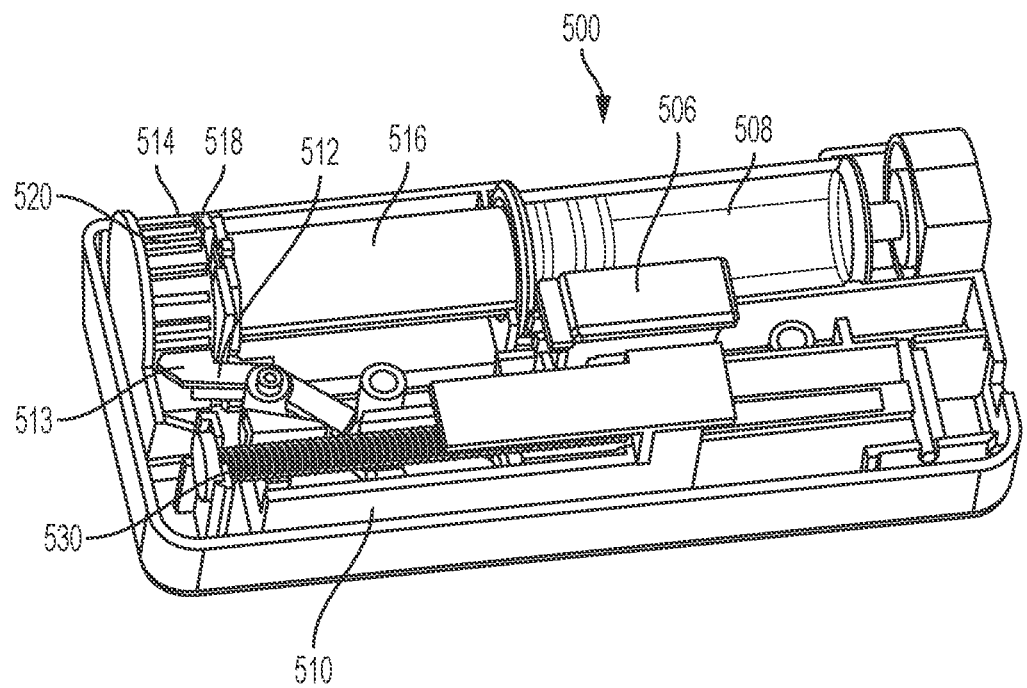
FIG. 73 is a perspective view of the drive assembly of FIG. 72 according to one aspect of the present invention, showing a top portion of a housing removed.
Figure 74:
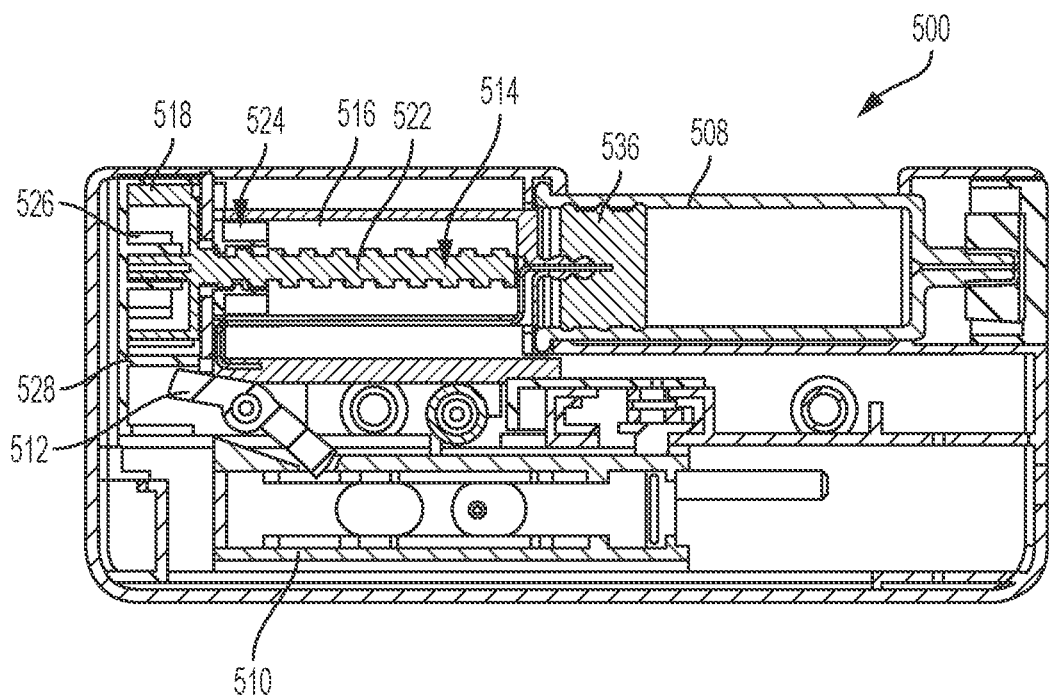
FIG. 74 is a cross-sectional view of the drive assembly of FIG. 72 according to one aspect of the present invention, showing a pre-use position of the drive assembly.
Figure 75:
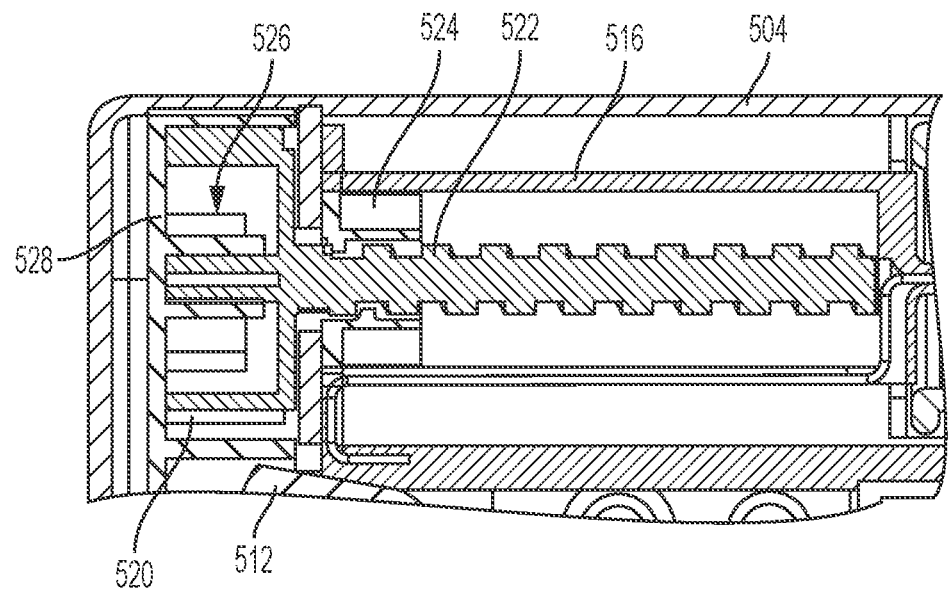
FIG. 75 is an enlarged cross-sectional view of the drive assembly of FIG. 72 according to one aspect of the present invention, showing a pre-use position of the drive assembly.
Figure 76:
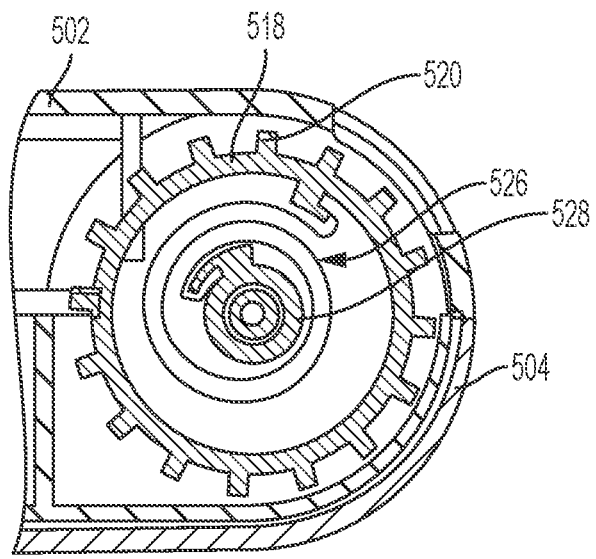
FIG. 76 is a top view of a biasing member of the drive assembly of FIG. 72 according to one aspect of the present invention.

Referring to FIGS. 72-77, a drive assembly 500 for a drug delivery system according to one aspect of the present invention is shown. The drive assembly 500 includes an actuation button 506, a container 508, a needle actuator assembly 510, an actuation release or flipper 512, a lead screw 514, and a plunger 516. The lead screw includes a drum portion 518 with external radially-protruding vanes 520, and, as best shown in FIGS. 74 and 75 and subsequently described in greater detail, a screw thread portion 522. Prior to activation, as best shown in FIGS. 73 and 76 one end 513 of the actuation release 512 engages one of the vanes 520 to prevent rotation of the lead screw 514.

According to one aspect, as shown in FIGS. 74-76, the screw thread portion 522 of the lead screw 514 engages internal threads of a nut 524 connected with the plunger 516. According to another aspect, the nut and its internal threads are integrally formed with the plunger as a unitary structure. Additionally, a constant force spring 526 is received within the drum portion 518 and biases the lead screw 514 in a rotational direction. According to one aspect, the spring 526 is secured to the base cover 504. According to another aspect, as shown in FIGS. 74-76, a drive assembly housing 528 is disposed within the system and the spring 526 is secured to the power pack housing 528.

Unlike a helical spring, such as a compression spring, which has a force profile proportional to its displacement, the constant force spring 526 and the like maintain a relatively flat or even force profile over a long working length. The even force profile advantageously provides an injection force that is proportional to the spring force. This will provide a flat or even injection force, and thus, a substantially constant injection rate for the medicament. Although the spring 526 is illustrated in FIG. 76 as having only two turns of material, one skilled in the art will appreciate that fewer or greater numbers of turns can be employed. Preferably, an assembler winds the spring 526 when the drive assembly 500 is assembled, and the spring 526 is stored in the wound position until the time of actuation.

Figure 77:
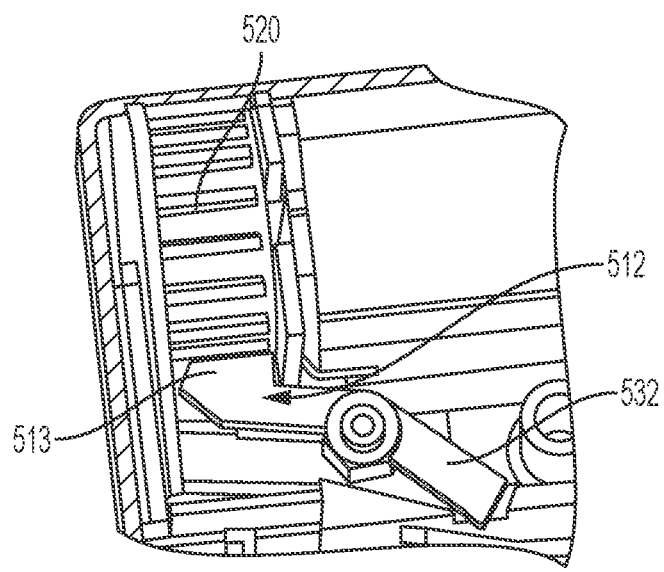
FIG. 77 is a perspective view of the drive assembly of FIG. 72 according to one aspect of the present invention, showing a restriction member engaged with the drive assembly.
Figure 78:
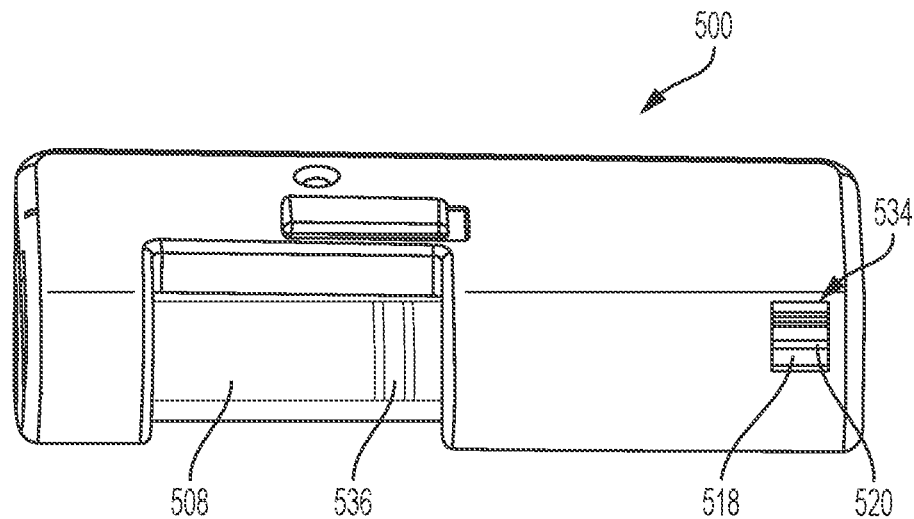
FIG. 78 is a perspective view of a drive assembly for a drug delivery system according to one aspect of the present invention.

Upon actuation of the system, the needle actuator assembly 510 is released to axially displace (to the right in FIGS. 72-75) from the pre-use position to the post-use position under the influence of a biasing member 530 (best shown in FIG. 73). During this displacement, the needle actuator assembly 510 bears against a second end 532 of the actuation release 512 and rotates the release 512 counter-clockwise, as shown in FIG. 77. This counter-clockwise rotation of the actuation release 512 frees the first end 513 thereof from engagement with the vane 520. Subsequent to the disengagement of the first end 513 from the vane 520, the spring 526 unwinds and drives rotation of the lead screw 514, which, in combination with the nut 524, advances the plunger 514 to dispense the medicament.

As the lead screw 514 is rotating, the rotation of the drum portion 518 and the vanes 520 is visible through a window 534 in the housing. This window 534 indicates progress of the screw in a way that is much more apparent than viewing the linear movement of the stopper 536 in the container 508. In fact, this rotational movement is many times more sensitive than the linear movement. One skilled in the art will appreciate that the exact amount of advantage or increase depends on the pitch of screw thread portion 522 of the lead screw 514, the diameter of the drum portion 518, and number of vanes 520 on the drum portion 518.

Referring to FIGS. 78-83, a drive assembly 600 for a drug delivery system according to a further aspect of the present invention is shown. The drive assembly 600 acts to store a spring's mechanical energy and to activate it when triggered. The drive assembly 600 includes a medicament barrel 601, a stopper 602 slidably disposed in the barrel 601, a first valve plunger 603, a second valve plunger 604, a first revolve nut 605, and a second revolve nut 606. The drive assembly 600 also includes a rotary indicator 607, a locking element 608, a constant force spring 609 disposed within the rotary indicator 607, and an actuation release or flipper 610. The drive assembly 600 is at least partially disposed within a housing 611 that can be assembled into a drug delivery system.

The constant force spring 609 is contained between the housing 611 and the rotary indicator 607 within a drum portion 616 of the rotary indicator 607. The drive assembly's inactive state is such that energy is applied by uncoiling the spring 609 and harnessing this energy geometrically with the housing 611, rotary indicator 607, and actuation release 610. When the drive assembly 600 is deactivated, the spring recoils and translates the mechanical energy into rotational motion of the rotary indicator.

The telescoping multi-part plunger is oriented along a force axis between the medicament barrel 601 and the rotary indicator 607. The rotary indicator 607 features a threaded shaft 618. According to one aspect, the threads are dual lead, and are either square or rectangular in nature. The multi-part telescoping plunger includes a two-part threaded nut (first revolve nut 605 and second revolve nut 606) and a two-part plunger (first valve plunger 603 and second valve plunger 604). The second revolve nut 606 is a threaded shaft that mates with the rotary indicator 607 and first revolve nut 605 and features matching threads on its inner and outer surfaces (internal and external threads, respectively) to mate with them. The second revolve nut 606 also has a circular collar 620 (best shown in FIG. 82) on its proximal end that bottoms down on the second valve plunger 604. The second revolve nut 606 is free to spin along the force axis. The first revolve nut 605 is also a threaded shaft that features threads on its inner diameter corresponding to the external threads of the second revolve nut 606 to mate with the second revolve nut 606.

According to one aspect, on one end, the first revolve nut 605 has a hexagonal collar that press fits on the first valve plunger 603 to fixedly connect the first valve plunger 603 with the first revolve nut 605. In the drive assembly 600, the first revolve nut is not free to rotate and will only translate when the power module subassembly is actuated.

The second valve plunger 604 is a hollow cylindrical component with a small collar 622 on its distal end, a large collar 624 on its proximal end, and an extended L-shaped arm 626 (best shown in FIG. 83) protruding from the large proximal collar 624. According to one embodiment, the small collar 622 is discontinuous and features four leaf cantilevered arms or leaf springs 623 that allow the collar to bend and mate with the first valve plunger 603. The inner surface of the second valve plunger 604 has an undercut through its length terminating at its proximal end a radially inward protruding shelf 628 of the large collar 624. The shelf 628 engages the second revolve nut 606 within the telescoping assembly.

Figure 79:
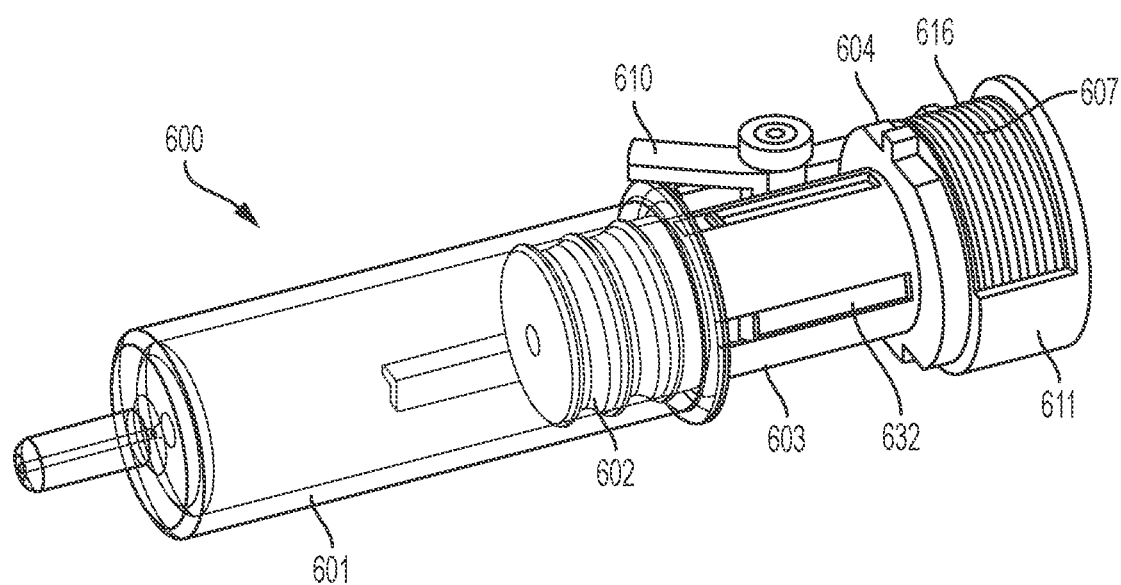
FIG. 79 is a perspective view of the drive assembly of FIG. 78 according to one aspect of the present invention, showing a pre-use position of the drive assembly.
Figure 80:
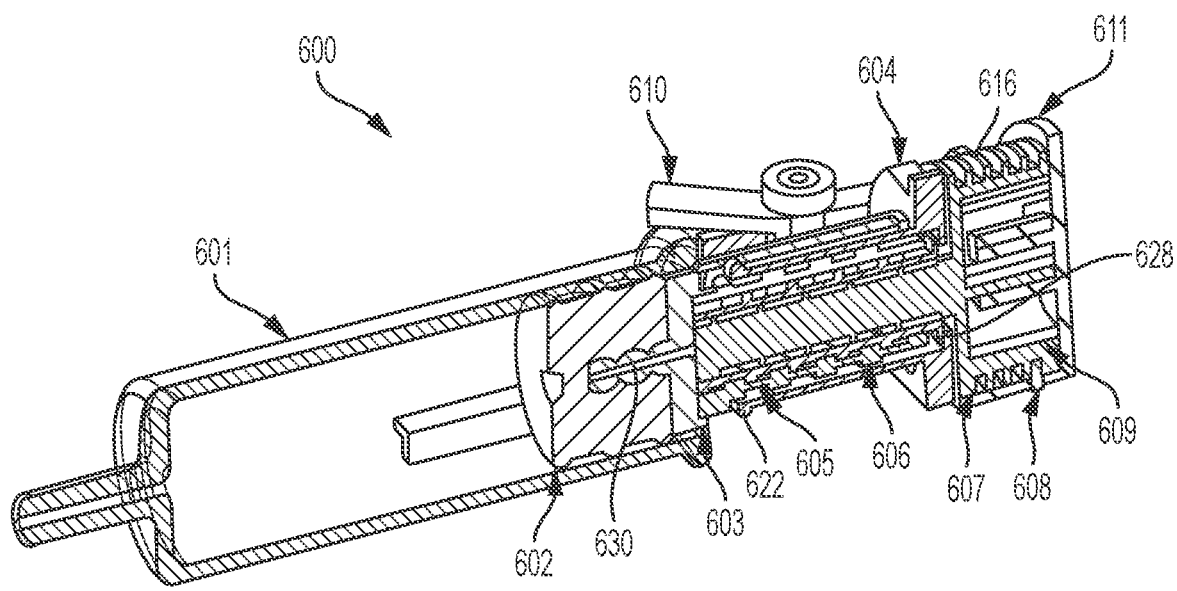
FIG. 80 is a cross-sectional view of the drive assembly of FIG. 78 according to one aspect of the present invention.
Figure 81:
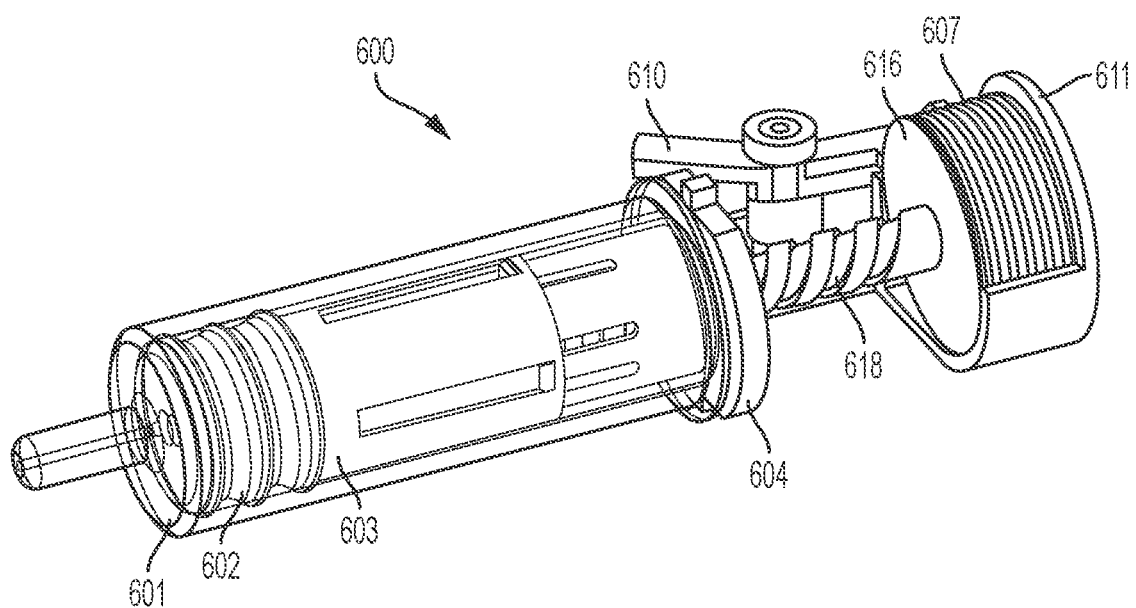
FIG. 81 is a perspective view of the drive assembly of FIG. 78 according to one aspect of the present invention, showing a post-use position of the drive assembly.
Figure 82:
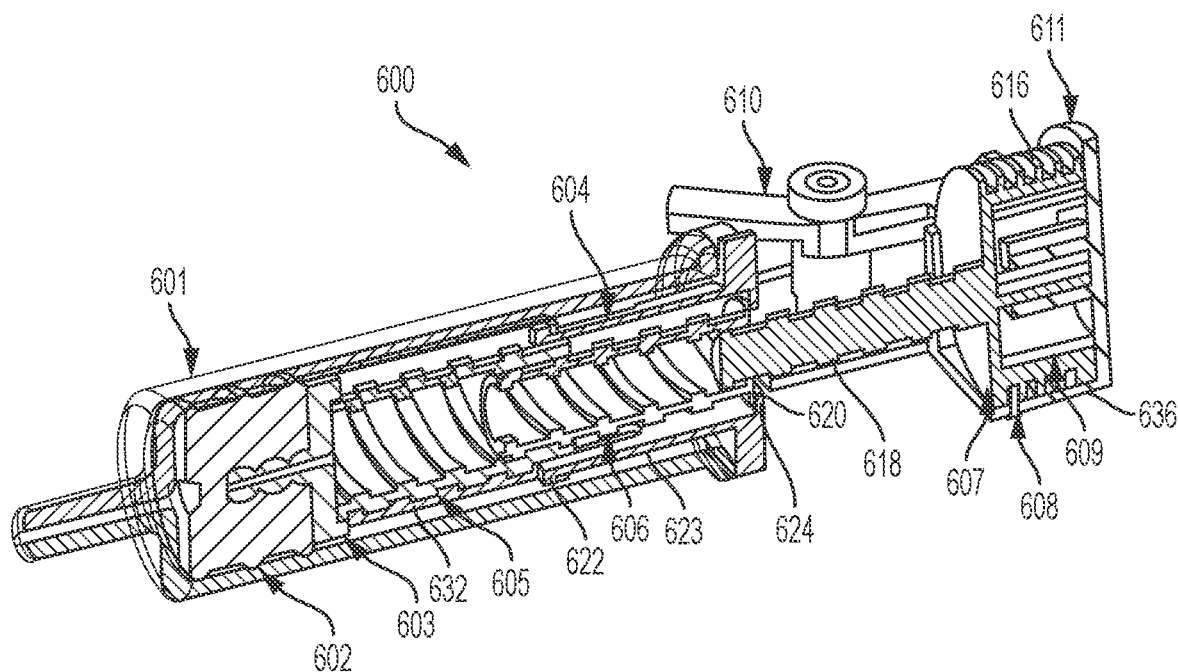
FIG. 82 is a cross-sectional view of the drive assembly of FIG. 78 according to one aspect of the present invention, showing a pre-use position of the drive assembly.
Figure 83:
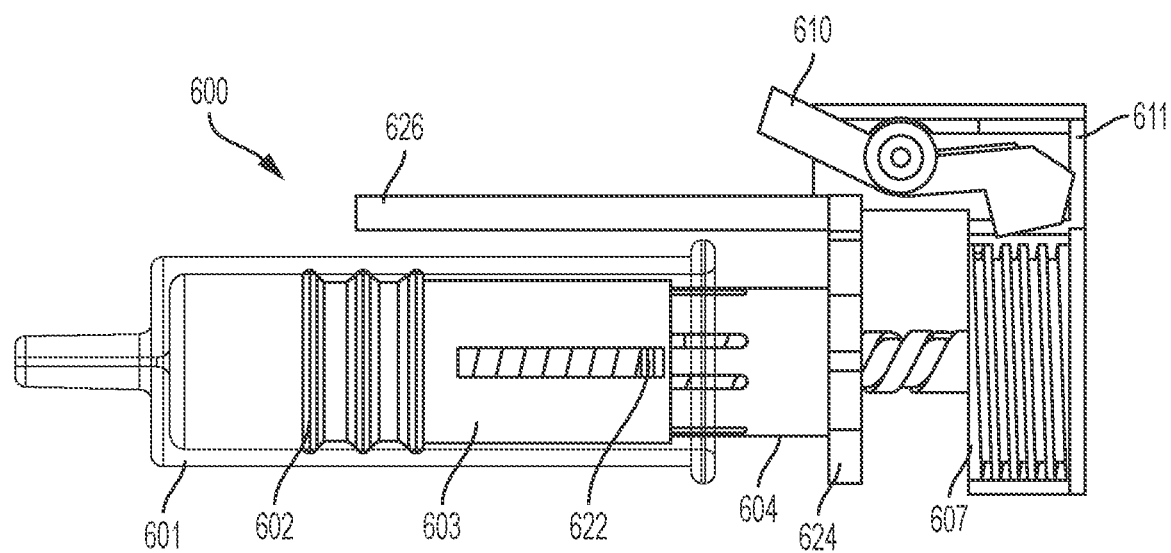
FIG. 83 is a front view of the drive assembly of FIG. 78 according to one aspect of the present invention, showing a use position of the drive assembly.

The first valve plunger 603 attaches to the stopper 602 and is also a hollow cylindrical component that mates with the second valve plunger 604. More specifically, the first valve plunger 603 features a cylindrical protrusion 630 on its distal end to mate with the stopper 602. According to one aspect, as best shown in FIG. 79, four thru slots 632 are disposed on the proximal quadrants of the first valve plunger 603 to mate with the leaf springs or arms 623 and small collar portion 622 of the second valve plunger 604. Both the first and second valve plungers 603 and 604 are free to slide.

Telescoping is achieved when the constant force spring 609 recoils and the rotary indicator 607 starts spinning. The threaded attachment between the rotary indicator 607 and the second revolve nut 606 causes second revolve nut 606 to rotate. But because the second revolve nut 606 is threaded to the first revolve nut 605, which cannot rotate and experiences resistance to distal translation due to the pressure caused by medicament in the barrel 601, the second revolve nut 606 will displace proximally and bottom out on the second valve plunger's radially inward protruding shelf 628. The second valve plunger 604 is prevented from displacing proximally by the housing 611. Subsequently, and with continued rotation of the rotary indicator 607, because the second revolve nut 606 is threaded with the first revolve nut 605 (which cannot rotate) the first revolve nut 605 translates distally to push the first valve plunger 603 (and the stopper 602) to dispense medicament from the barrel 601.

The first valve plunger 603 displaces distally relative to the second valve plunger 604 until the small collar sections 622 (respectively disposed on the distal ends of the leaf springs or arms 623 of the second valve plunger 604) engage the corresponding proximal ends of the slots 632 of the first valve plunger 603. This locks the relative positon of the first and second valve plungers 603 and 604, with continued rotation of the rotary indicator 607, both valve plungers translate distally while also pushing the second revolve nut along (because of its proximal engagement with the shelf 624).

The initial and final positions of the telescoping plunger, and thus the medicament dose, are controlled by the rectangular thread form of the threaded shaft 618 of the rotary indicator 607, a threaded shaft on the drum portion 616 of the rotary indicator 607, and a stepped pin that acts as the locking element 608. According to one aspect, threaded shaft on the drum portion 616 of the rotary indicator 607 is single lead, and because the rest of the components in the telescoping chain have dual lead threads, the axial travel of the other threaded components is twice the axial travel of the lock 608 relative to the rotary indicator.

According to one embodiment, the lock 608 is cylindrical and features a domed tip on one end and a cylindrical collar on the other. The threads on the exterior of the rotary indicator's drum portion 616 along with a slot and undercut 636 at the bottom of the housing 611 captures the lock 608 in place, allowing it to slide parallel to the force axis. Thus, as the spring 609 is released and the rotary indicator 607 turns, the lock 608 translates as well and creates a positive stop when the distal end of the thread on the exterior of the rotary indicator's drum portion 616 is reached.

One benefit of aspects of the drive assembly 600 include the use of a constant force spring 609, the mechanical energy of which is converted into substantially constant linear force to the medicament in the barrel 601. In turn, this creates a uniform medicament delivery rate. Another benefit is that employing the telescoping plunger driven by a thread form, the drive assembly can create in-line space savings of up to 0.75 inches compared to other plunger designs. Additionally, the drive assembly provides a controlled medicament dose through an initial and final mechanical constraint within the same component.

As previously noted, other drug delivery systems utilize a compressed coil spring, which exerts a maximum force at actuation that eventually decreases as the spring expands. A decreasing force at the plunger translates into variable medicament delivery time and medicament exit pressure. By using a constant force spring, the force exerted on the plunger is constant from the beginning to the end of the dosage. In addition, the distance a coil spring has to travel in addition to the length of a static plunger that needs translate inside the drug container can create a long assembly. In contrast, in embodiments of the present invention, the constant force spring is contained radially and does not require any additional space before or after activation. Furthermore, the aspects of the telescoping plunger allow that the plunger length of the can be significantly reduced in comparison to the length of a static plunger.

Previous drug delivery systems have variable dose accuracy performance because the mechanical components enabling the drug delivery create a geometric dependence by bottoming down on the container, which cannot be fabricated with tight tolerances. Some embodiments of the present invention create a control to the start and end times of the translating plunger via a thread form in the rotary indicator and the use of the constant force spring.

The drive assembly creates a space saving geometry in addition to well-controlled time, volume and pressure for the drug delivery device, which translates to a more attractively compact and precise drug delivery device.

Some aspects of the drive assembly implement three rotating threaded shafts to create a linear space savings of about 0.75 inch. In other aspects, the same concept can be employed using two rotating threaded shafts and result in a space savings of about 0.5 inch. Some aspects of the present invention convert the rotational energy of a constant force spring to a translational force motion of a plunger.

Referring to FIGS. 84A-84G, a plunger assembly 400 for use in connection with a drive assembly according to one aspect of the present invention is shown.

Elements in a chain of tolerances in the plunger assembly 400 include a thickness (A) of a flange 402 of an inner plunger 404, an internal length (B) of an outer plunger 406 between an internal proximal end 408 and an internal shoulder 410, and an initial offset distance ($C_1$) between the inner plunger flange 402 and the internal proximal end 408 of the outer plunger. This initial offset distance ($C_1$) is preferably greater than a gap distance ($C_2$) between outer plunger 406 and the proximal end of the medicament barrel 412. The chain of tolerances in the stopper spacer assembly 400 also includes the internal barrel diameter (D). Once assembled, the stopper spacer 414 and the outer plunger 406 are unique for a given medicament volume.

Figure 84A:
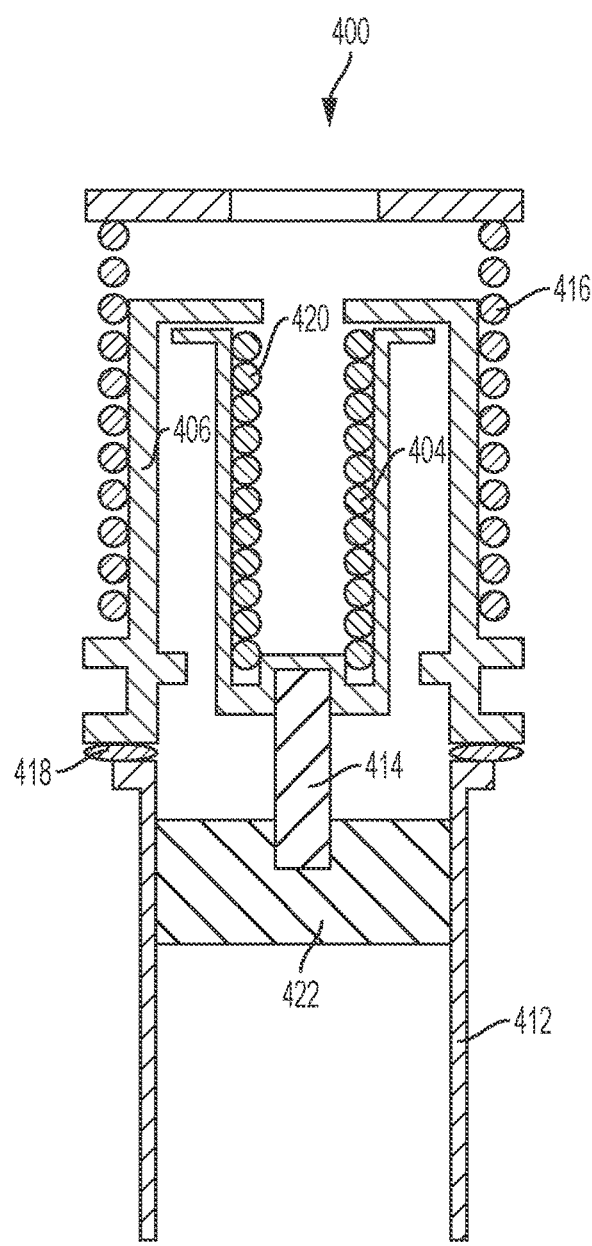
FIG. 84A is a schematic view of a drive assembly according to one aspect of the present invention, showing the drive assembly in a pre-use position.
Figure 84B:
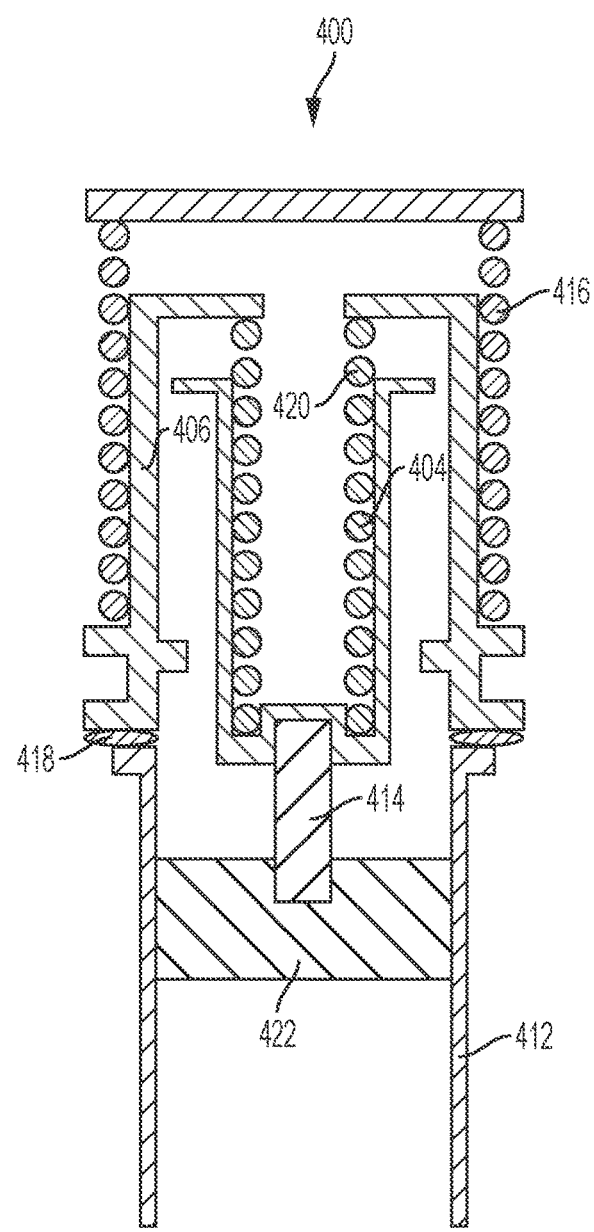
FIG. 84B is a schematic view of the drive assembly of FIG. 84A according to one aspect of the present invention, showing the drive assembly in a use position.

FIGS. 84B-84G illustrate operation of the plunger assembly 400. As shown in FIG. 84B, when the system is actuated, the both inner and outer plungers 404 and 406 are released. An outer spring 416 pushes the outer plunger 406 into the barrel 412, compressing damping material 418, and an inner spring 420. The stopper 422 does not yet moved relative to the barrel 412 due to the fluid column of medicament.

Figure 84C:
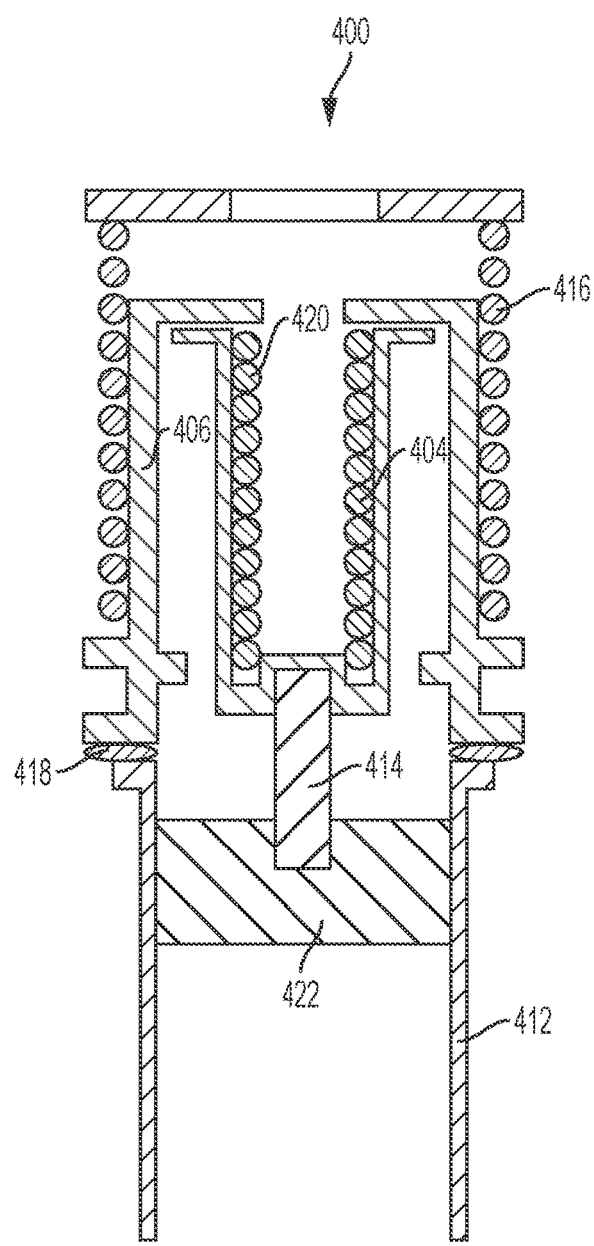
FIG. 84C is a schematic view of the drive assembly of FIG. 84A according to one aspect of the present invention, showing the drive assembly in a use position.

Next, as shown in FIG. 84C, the outer spring 416 distally displaces the outer plunger 406 and the barrel 412 to open a valve (not shown) at the distal end of the barrel 412 that establishes fluid communication with the needle (not shown). Due to the incompressibility of the liquid medicament, the stopper 422 cannot displace relative to the barrel 412 until the valve is opened and the fluid path to the patient needle is established.

Figure 84D:
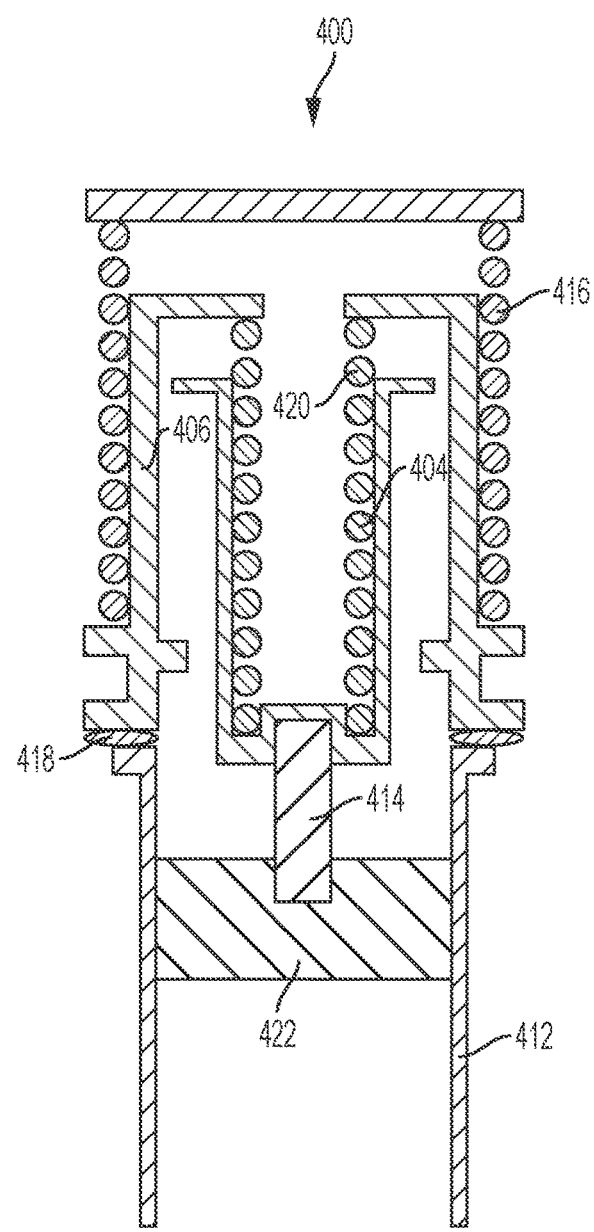
FIG. 84D is a schematic view of the drive assembly of FIG. 84A according to one aspect of the present invention, showing the drive assembly in a use position.

Subsequently, as shown in FIGS. 84D and 84E, the inner spring 420 displaces the inner plunger 404, the stopper spacer 414, and the stopper 422, to dispense the fluid.

FIG. 84F illustrates the end of medicament delivery when the proximal flange 402 of the inner plunger 404 contacts the internal shoulder 410 of the outer plunger 406, thereby ceasing displacement of the inner plunger 404 (and the stopper spacer 414 and stopper 422) relative to the medicament barrel 212 and stopping the flow of medicament.

Figure 84G:
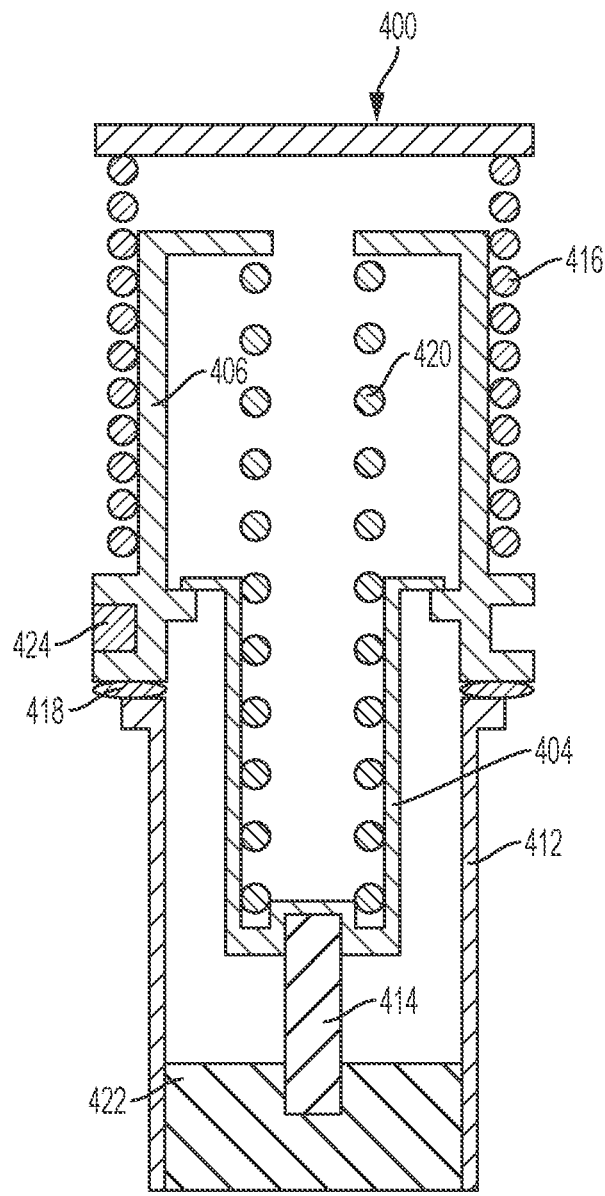
FIG. 84G is a schematic view of the drive assembly of FIG. 84A according to one aspect of the present invention, showing the drive assembly in a post-use position.

According to one aspect, as shown in FIG. 84G, the cessation of displacement of the inner plunger 404 relative to the medicament barrel 412 triggers an end-of-dose indicator for the system.

While a specific spacer assembly 40 and spacer 226 have been described above, the custom spacer assembly may have a variety of configurations. The custom spacer assembly may be situated against a proximal end of the stopper in the container or connected to the stopper in another manner. The spacer design is such that its effective length can be changed in order to allow the dispensing of a precise quantity of medicament. The length adjustment is intended to compensate for manufacturing tolerances within the container, the fill volume, and especially the stopper length, which can add up to ⅓ of the variability in a delivered dose using a non-adjustable spacer. The spacer length can be adjusted through several techniques, depending on the specific aspect. The spacer length can be self-adjusting based on its location to the back of the container, adjustable by assembly equipment at the time of final assembly of the primary container into the subassembly, and it can be made an integral part of the stopper and adjusted as a subassembly prior to filling. The adjustable spacer allows a more precise volume of fluid to be injected compared to a non-adjustable stopper.

Figure 85:
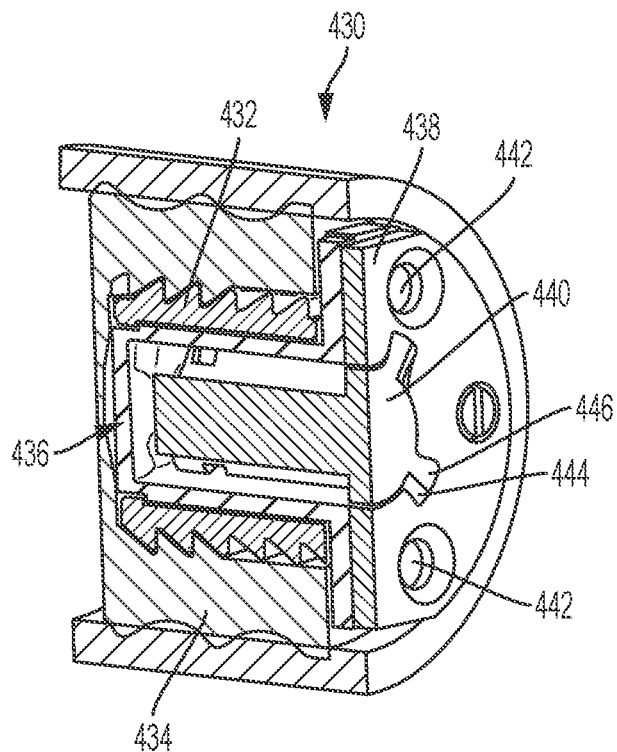
FIG. 85 is a perspective view of a spacer assembly for a drug delivery system according to one aspect of the present invention, showing an assembled, pre-use position of the spacer assembly.
Figure 86:
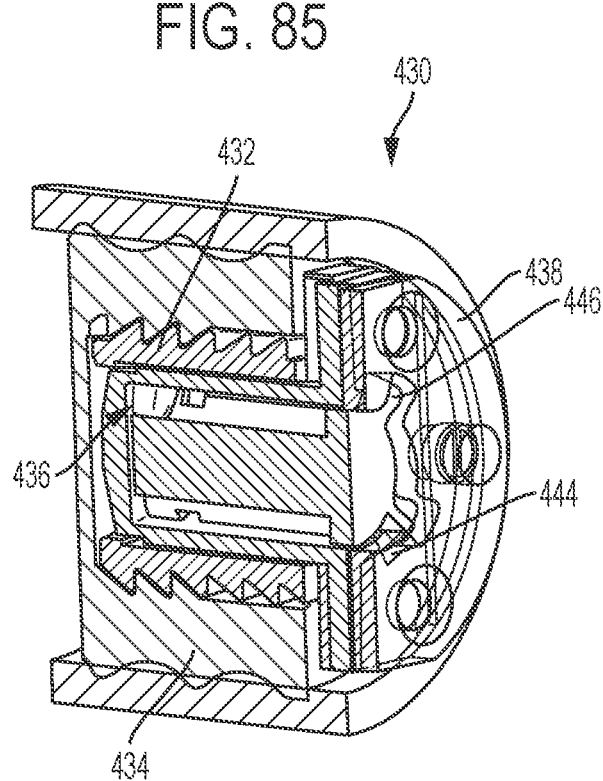
FIG. 86 is a perspective view of the spacer assembly of FIG. 85 according to one aspect of the present invention, showing a use position of the spacer assembly.

Referring to FIGS. 85 and 86, a collapsible spacer assembly 430 includes a forward spacer portion 432 secured to a stopper 434, an inner plunger 436, a rear spacer portion 438, and a rotating shuttle 440. The inner plunger 436 can translate relative to the forward spacer portion 432, but not rotate relative thereto. Similarly, the rear spacer portion 438 can also move axially relative to the forward spacer portion 432, but not rotate relative to the forward spacer portion 432. As subsequently described in greater detail, the rotating shuttle 440 first rotates, and subsequently translates.

According to one aspect, forward spacer portion 432 is fixedly secured to the stopper 434. One skilled in the art will understand that many methods can be employed to secure the forward spacer portion 432 to the stopper 434, for example, adhesive, mechanical fasteners, or any other suitable arrangement. Preferably, the forward spacer portion 432 includes threads that engage mating threads in the stopper 434.

When the stopper spacer assembly 430 is screwed into the stopper 434, an axial load is applied through access openings 442 in the rear spacer portion 438. This force can be used to push the stopper 434 forward, applying pressure to the fluid medicament. This pressure causes the front (distal) face of the stopper 434 to deflect and press proximally, pushing back on the rear spacer portion 438 and rotating the rotating shuttle into its "as assembled" condition. In other words, when a medicament barrel is filled with medicament and the system's plunger is applying axial force to the medicament via the spacer assembly 430, the distal face of the stopper 434 is deformed by the pressure of the medicament. During medicament delivery, pressure is applied by a drive assembly (via the plunger) to the rear spacer portion 438, which in turn applies a rotational torque to the rotating shuttle 440 via helical faces 444 of the rear spacer portion 438. But the stopper deformation from the medicament provides a rearward or proximal force on the inner plunger 436, which prevents rotation of the rotating shuttle 440.

According to one aspect, an axial reaction load on the inner plunger 436 can be increased by increasing the length of the inner plunger 436.

Figure 87:
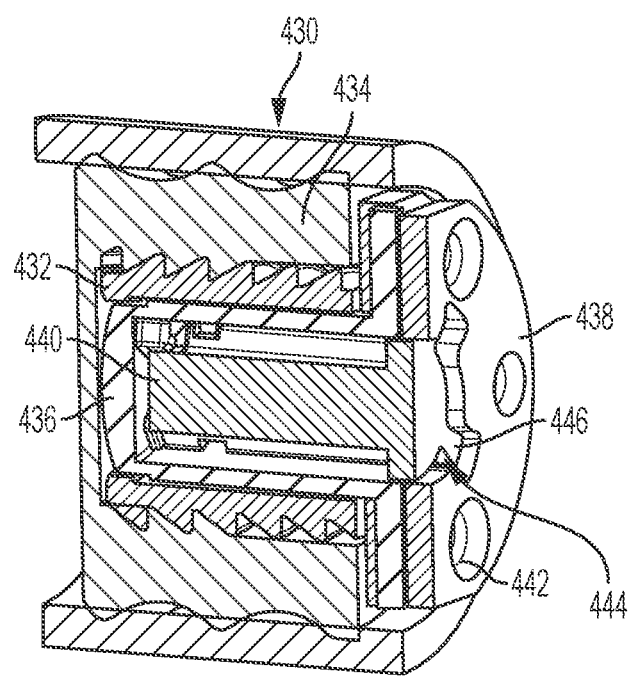
FIG. 87 is a perspective view of the spacer assembly of FIG. 85 according to one aspect of the present invention, showing an initial post-use position of the spacer assembly.

Once the medicament delivery is complete, as shown in FIG. 87, the pressure on the stopper 434 decreases, thereby permitting the distal end of the inner plunger 436 to displace distally. This distal displacement permits the rotating shuttle 440 to rotate. The continued axial force applied by the drive assembly rotates and distally displaces the rotating shuttle 440 due to interaction of the helical faces 444 in the rear spacer portion 438 with corresponding cam-faced arms 446 of the rotating shuttle 440. According to one aspect, this final movement of the rotating shuttle 440 causes the drive assembly to trigger needle retraction.

Figure 89:
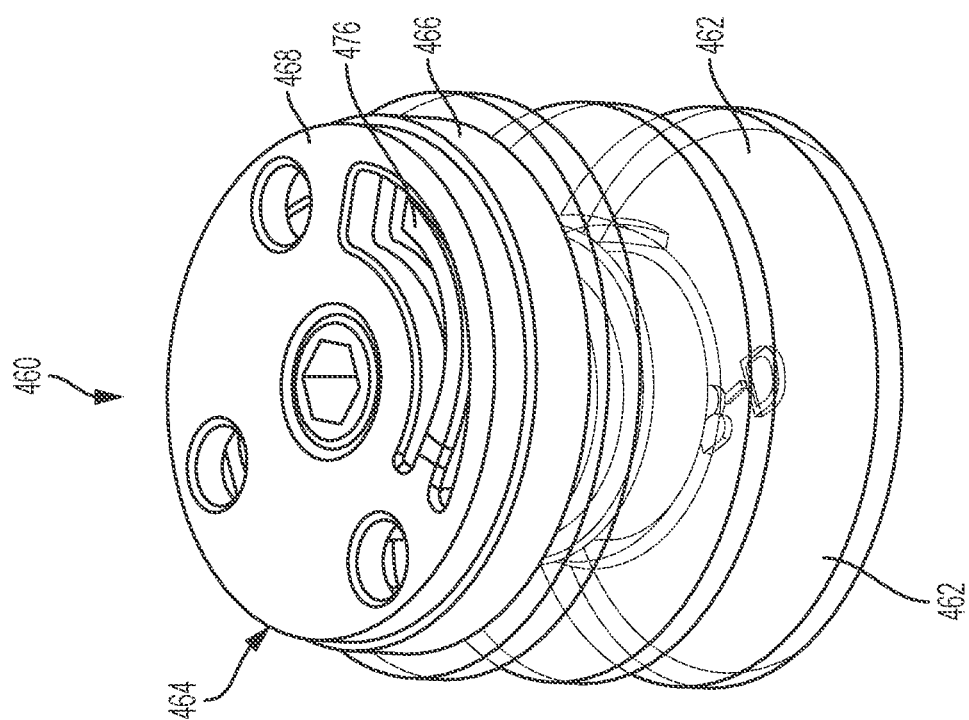
FIG. 89 is a perspective view of the spacer assembly of FIG. 88 according to one aspect of the present invention.
Figure 88:
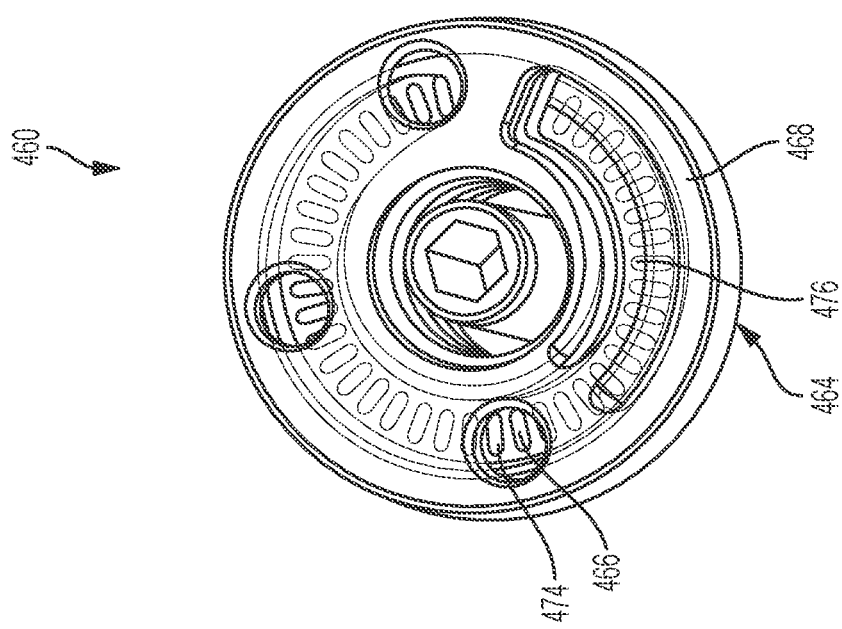
FIG. 88 is a top view of a spacer assembly for a drug delivery system according to one aspect of the present invention.
Figure 90:
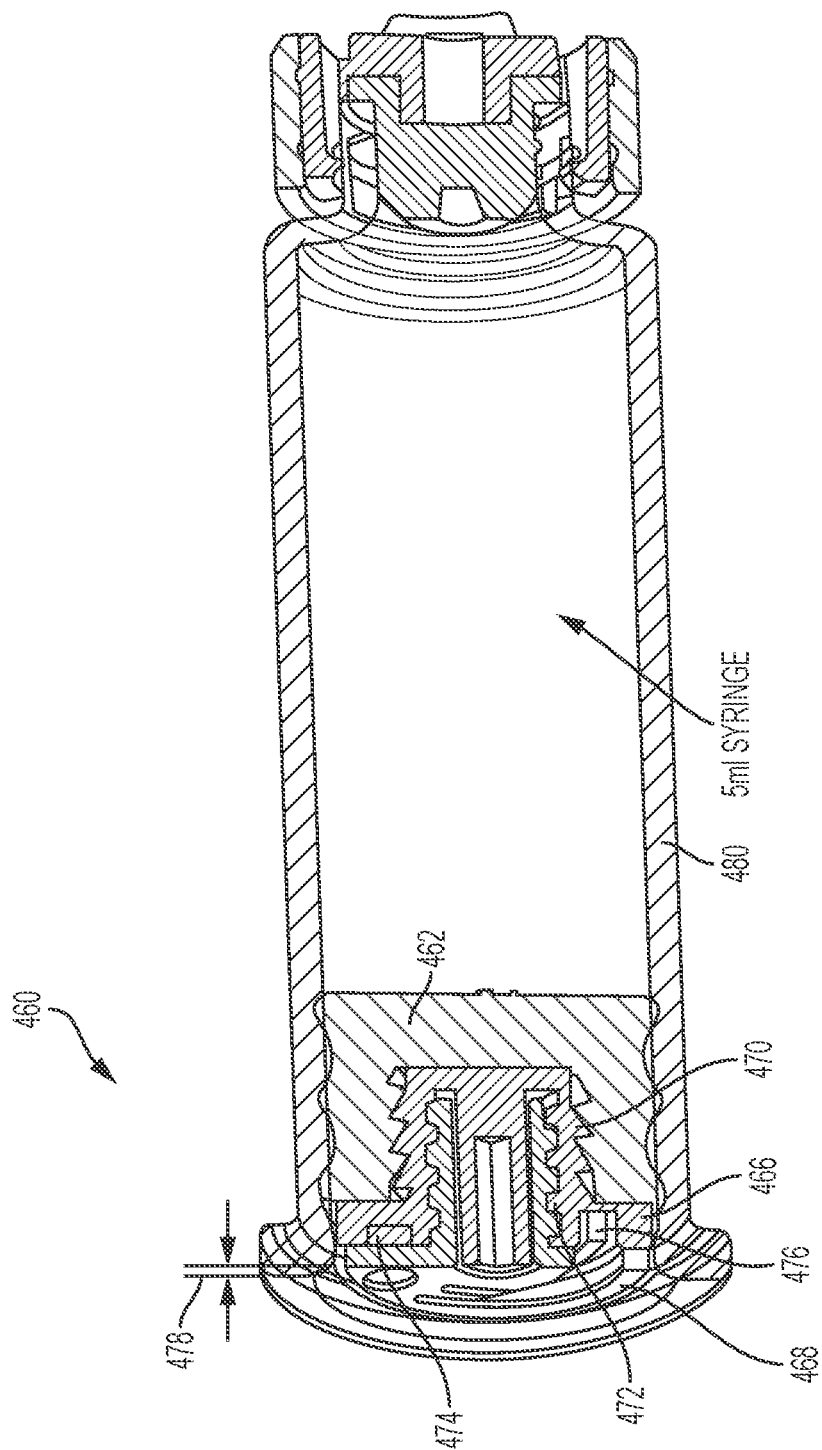
FIG. 90 is a cross-sectional view of the spacer assembly of FIG. 88 according to one aspect of the present invention.

Referring to FIGS. 88-90, a spacer assembly 460 according to a further aspect of the present invention is shown. The spacer assembly 460 shown in FIGS. 88-90 allows for the removal of the effect of manufacturing tolerance build up through adjustment of the spacer assembly thereby allowing each system to inject the same amount of medicament.

As shown in FIG. 89, the spacer assembly 460 includes a stopper 462 and a stopper spacer 464. The stopper spacer 464 includes a fixed spacer piece or fixed spacer 466 that is fixedly connected with the stopper 462, and an adjustable spacer piece or adjustable spacer 468 that is rotationally displaceable in one direction relative to the fixed spacer 466.

One skilled in the art will understand that many methods can be employed to secure the fixed spacer 466 to the stopper 462, for example, adhesive, mechanical fasteners, or any other suitable arrangement. Preferably, the fixed spacer 466 includes one or more external threads that engage one or more mating threads in the stopper 462. According to one aspect, the adjustable spacer 468 has a distal stem with an external thread 470. The distal stem thread 470 engages an internal thread 472 in the fixed spacer 466 (best shown in FIG. 90) to rotationally control axial displacement of the adjustable spacer 468 relative to the fixed spacer 466.

As shown in FIGS. 88 and 89, the fixed spacer 466 includes radially spaced detents 474 and the adjustable spacer 468 includes a spring detent arm 476, the free end of which engages a selected one of the detents 474 to prevent rotation and axial displacement of the adjustable spacer 468 toward the fixed spacer 466. The free end of the spring detent arm 476 is shaped to pass over the detents 474 in one direction, thereby permitting rotation and proximal axial displacement of the adjustable spacer 468 away from the fixed spacer 466.

Despite variations in the dimensions of stoppers and containers, the adjustable spacer 468 can be adjusted relative to the fixed spacer 466 to provide a consistent axial length of the stopper assembly 460.

As shown in FIG. 90, once the container is filled, an axial load, such as a load that would be encountered when installed in the system 10, 200, can be applied to the adjustable spacer 468 (and thus, the fixed spacer 466 and the stopper 462). Once the axial load is applied, the adjustable spacer 468 can be proximally backed out to ensure a consistent gap 478 between the proximal end of a medicament barrel 480 and the proximal face of the adjustable spacer 468, thereby accounting for variations in the medicament barrel glass and the compressibility of any entrapped air. In other words, the spacer assembly 460 allows the adjustable spacer 468 to have a predetermined set position relative to the container 14 independent of the variables of the container 14 and stopper length. Accordingly, the start position of the spacer assembly 460 is a predetermined distance from the container 14 and the end position of the spacer assembly 460 is also a predetermined distance from the container 14 such that the travel of the stopper 462 is defined by the effective length of the plungers 52, 54 of the drive assembly 12.

Figure 91:
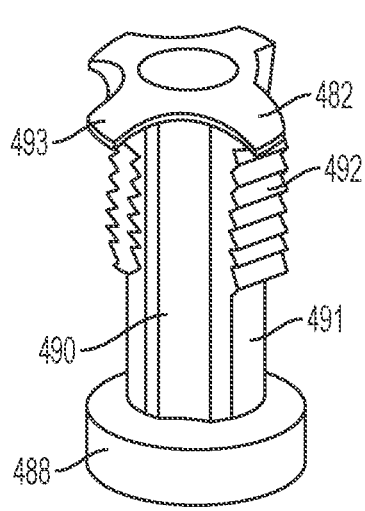
Figure 92:
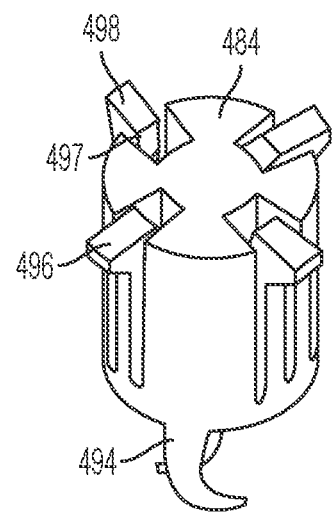

Referring to FIGS. 91 and 92, a base column 482 and a cap 484 of an automatically adjusting spacer 486 according to one aspect of the present invention is shown. The base column 482 includes a base portion 488 and an axially extending column 490. According to one embodiment, the base column 482 includes a plurality of columnar protrusions 491 that each have a plurality of ratchet teeth 492 disposed on a proximal portion thereof. A locking barb 493 is disposed at the proximal end of each of the plurality of ratchet teeth 492. The cap 484 is hollow, and a distal end of the cap 484 includes one or more axial springs 494. According to one aspect, the axial springs 494 are bent, cantilevered arms formed during molding of the cap 484. According to another aspect, a separate biasing member, such as a compression spring can be employed in the automatically adjusting spacer 486. When assembled with the base column 482, the springs 494 engage the base portion 488 and maintain an initial spacing between the base column 482 and the cap 484. According to one aspect, the springs 494 are omitted. The cap 484 also includes a plurality of flexible cantilevered arms or tabs 496, which each have a free proximal portion with a plurality internal of ratchet teeth 497. The proximal end of each flexible tab 496 includes a foot 498.

Figure 93A:
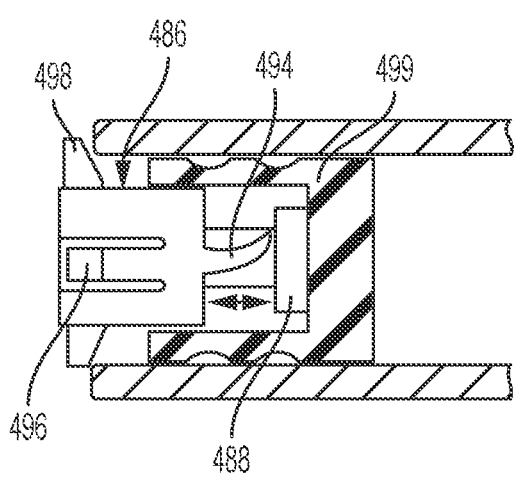
Figure 93B:
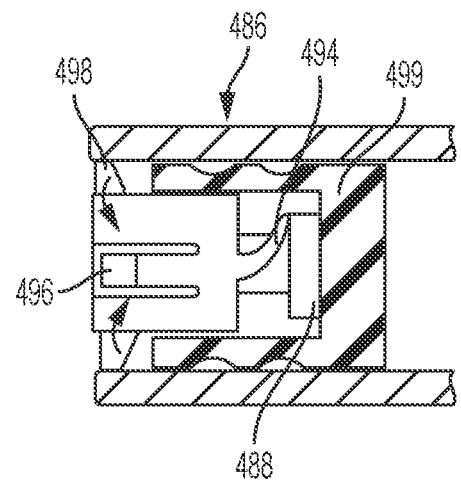
Figure 94:
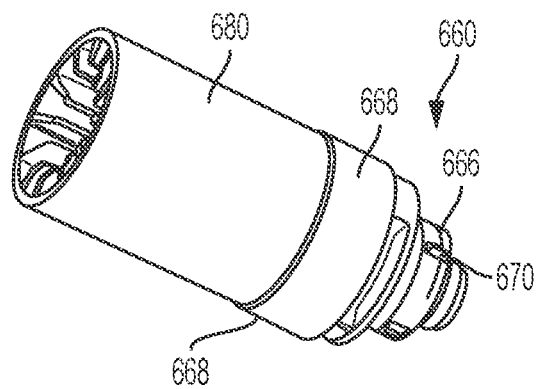
Figure 95:
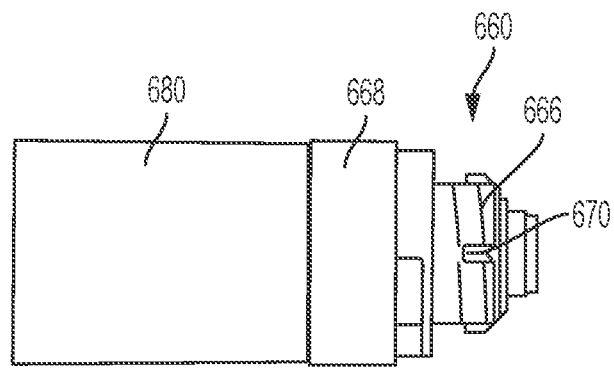
Figure 96:
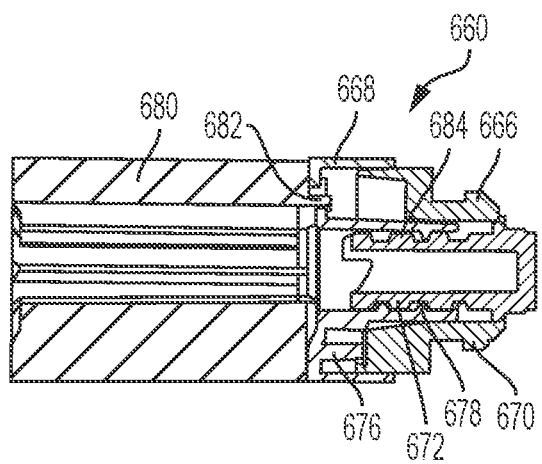
Figure 97:
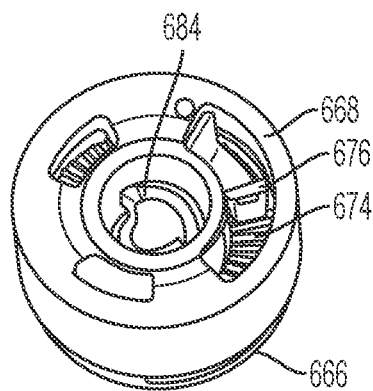
Figure 98:
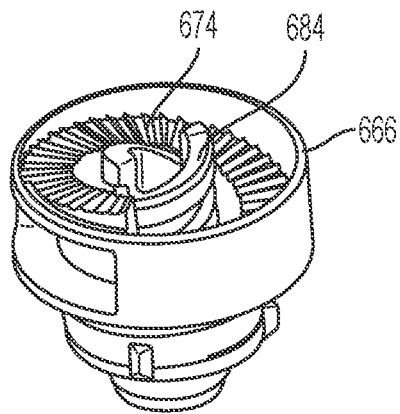
Figure 99:
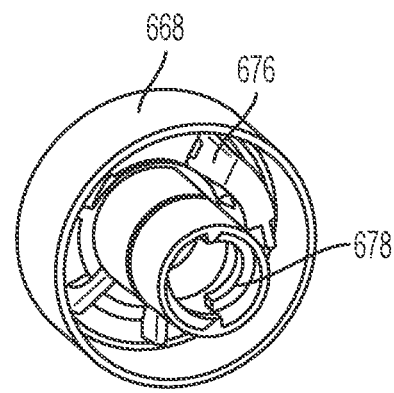
Figure 100:
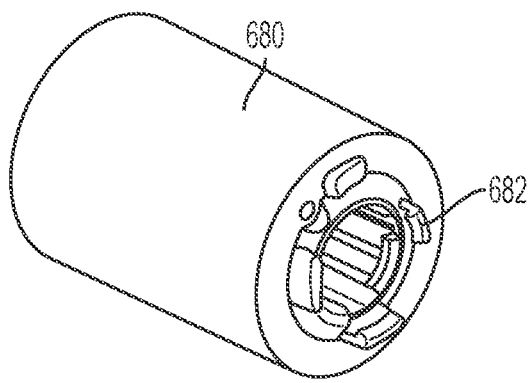

FIGS. 93A and 93B illustrate the cap of the automatically adjusting spacer deployed within a proximal recess of a stopper 499 at a proximal portion of a medicament barrel. The base column 482 is assembled into the hollow cap 484 with the base portion 482 engaging the stopper 499 and the feet 498 disposed outside the proximal end of the barrel.

In operation, as shown in FIGS. 93A and 93B, the cap 484 displaces distally relative to the base column 482 (as well as the stopper 499 and the barrel) until the proximal end of the cap 484 is flush with the end of the medicament barrel. This action causes the feet 498 to engage the internal surface of the barrel and displace radially inward, thereby forcing the ratchet teeth 492 into locking engagement with the ratchet teeth 497. The locking barb 493, the engagement of the ratchet teeth 492 and 497, and the engagement of the feet 498 with the internal surface of the barrel prevents the displacement of the cap 484 relative to the base column 482.

Thus, the automatically adjusting spacer 486 can accommodate differences in stoppers, barrel diameters, and medicament fill volumes, to automatically provide a bearing surface flush the proximal end of the medicament barrel.

Referring to FIGS. 94-100, a spacer assembly 660 according to a further aspect of the present invention is shown. The spacer assembly 660 is similar to the spacer assembly 460 discussed above and shown in FIGS. 88-90 and operates in a similar manner to achieve similar advantages. The spacer assembly 660 includes a fixed spacer 666 and an adjustable spacer 668. The fixed spacer 666 is configured to be received by the stopper 462 with lugs 670 engaging the stopper 462 to secure the fixed spacer 666 within the stopper 462, although other suitable securing arrangements, such as threads, may be utilized. The fixed spacer 666 includes interior threads 672 that receive exterior threads 678 of the adjustable spacer 668. The fixed spacer 666 includes a plurality of detents 674 positioned on a helical portion of the fixed spacer 666. The adjustable spacer 668 includes a spring detent arm 676 that engages one of the detents 674 to prevent rotation and axial displacement of the adjustable spacer 668 relative toward the fixed spacer 666. The spring detent arm 676 is shaped and configured to pass over the detents 674 in one direction to allow rotation and axial displacement of the adjustable spacer 668 away from the fixed spacer 666. The adjustable spacer 668 may be initially secured to the fixed spacer 666 via the threads 672, 678 by applying a force to the top of the spring detent arm 676, which biases the spring detent arm 676 away from the detents 674 to allow the spacers 666, 668 to be secured to each other. Accordingly, in the same manner as discussed above in connection with spacer assembly 460, the adjustable spacer is free to rotate in one axial direction to adjust the length of the spacer assembly 660.

Referring again to FIGS. 94-100, the spacer assembly 660 further includes a shim 680 configured to be received and secured to the adjustable spacer 668. Rather than providing a plurality of sizes of adjustable spacers 468, 668, a plurality of shim 680 sizes can be provided to accommodate a plurality of different fill volumes within the container 14. The shim 680 may be secured to the adjustable spacer 668 via a connector 682 extending from the shim 680 that is received by the adjustable spacer 668 using a snap-fit, although other suitable securing arrangements may be utilized. A center portion 684 of the fixed spacer 666 is configured to be engaged while the adjustable spacer 668 is rotated relative to the fixed spacer 666 to prevent rotation of the fixed spacer 666 along with the adjustable spacer 668. The center portion 684 of the fixed spacer 666 is accessible through an opening in the shim 680.

Referring to FIGS. 101-103, a spacer assembly 700 according to a further aspect of the present invention is shown. The spacer assembly 700 has a spacer 702 and shims 704. The spacer 702 has a central column 706 and a proximal flange 708. The central column 706 is received within and attached to the stopper 710 of the container 712 such that the proximal flange 708 abuts the proximal end of the stopper 710. The spacer 702 may be attached to the stopper 710 using any suitable method including, but not limited to, adhesive, a threaded connection, and a snap-fit connection. Rather than providing spacers 702 having proximal flanges 708 of different thicknesses, a plurality of shims 704 having different sizes are provided to accommodate a plurality of different fill volumes within the container 712. The shims 704 may have a shape corresponding to the shape of the proximal flange 708 and may be secured to the proximal flange 708 via a snap-fit connection or an adhesive, although other suitable securing arrangements may be utilized. The sizes of the available shims 704 may be arranged in a binary fashion, i.e., each successively thicker shim 704 is twice as thick as the previous shim 704, as shown in FIG. 103. The shims 704 may be attached to the spacer 702 before it is attached to the stopper 710 and/or after it is attached to the stopper 710.

Referring to FIGS. 104 and 105, a spacer assembly 800 according to a further aspect of the present invention is shown. The spacer assembly 800 has a movable spacer 802 and a fixed spacer holder 804. The spacer 802 has a central column 806 and a proximal flange 808. The spacer holder 804 is received by the stopper 810 and has a central cavity 812 that receives the central column 806 of the spacer 802. The spacer holder 804 may be fixedly attached to the stopper 810 using any suitable method including, but not limited to, adhesive, a threaded connection, and a snap-fit connection. An adhesive 814 attaches the outer surface of the sidewall 816 of the central column 806 to the inner surface of the sidewall 818 of the central cavity 812 of the spacer holder 804. The adhesive 814 may be any suitable adhesive including, but not limited to, contact adhesive, UV curable adhesive, and a laser curable adhesive. As shown in FIG. 104, the inner surface of sidewall 818 of the central cavity 812 of the spacer holder 804 may include a threaded portion 820 that engages a corresponding threaded portion 822 in the outer surface of the sidewall 816 of the central column 806 of the spacer 802. The adhesive may be provided on the threaded portion of the spacer 802 and/or the spacer holder 804. After the spacer 802 is threaded into the central cavity 812 of the spacer holder 804 and the desired length of the spacer assembly 800 is set, the adhesive 814 is cured attaching the spacer 802 to the spacer holder 804, thereby fixing the length of the spacer assembly 800. Alternatively, as shown in FIG. 105, a laser or ultrasonic weld 824 may be used to attach the spacer 802 to the spacer holder 804, thereby fixing the length of the spacer assembly 800. The spacer 802 may be transparent while the spacer holder is opaque.

Referring to FIG. 106, a spacer assembly 900 according to a further aspect of the present invention is shown. The spacer assembly 900 has a spacer 902 and a spacer holder 904. The spacer 902 has a central column 906 and a proximal flange 908. The spacer holder 904 is received by the stopper 910 and has a central cavity 912 that receives the central column 906 of the spacer 902. The spacer holder 904 may be attached to the stopper 910 using any suitable method including, but not limited to, adhesive, a threaded connection, and a snap-fit connection. An ultrasonic or laser weld 914 attaches the outer distal surface 916 of the central column 906 to the inner bottom surface 918 of the central cavity 912 of the spacer holder 904 locking the positon of the spacer 902 with respect to the spacer holder 904, thereby fixing the length of the spacer assembly 900. The height of the spacer 902 may be adjusted relative to the spacer holder 904 to provide an infinite number of height increments.

Referring to FIGS. 107 and 108, a spacer assembly 1000 according to a further aspect of the present invention is shown. The spacer assembly 1000 has a spacer 1002 and a spacer holder 1004. The spacer 1002 has a central column 1006 and a proximal flange 1008. The spacer holder 1004 is received by the stopper 1010 and comprises a sidewall 1012 extending in a proximal direction from a bottom portion 1014. The sidewall 1012 and the bottom portion 1014 define a central cavity 1016 that receives the central column 1006 of the spacer 1002. The spacer holder 1004 may be attached to the stopper 1010 using any suitable method including, but not limited to, adhesive, a threaded connection, and a snap-fit connection. The inner surface of sidewall 1012 of the spacer holder 1004 includes a threaded portion 1018 that engages a corresponding threaded portion 1020 in the outer surface of the central column 1006 of the spacer 1002. As shown in FIG. 107, the proximal end surface of the sidewall 1012 of the spacer holder 1004 includes a plurality of ratchet teeth configured to engage a flexible tab 1024 that extends axially in a distal direction from the proximal flange 1008 of the spacer 1002. The proximal end surface of the sidewall 1012 of the spacer holder 1004 on which the ratchet teeth are positioned is angled in a distal direction around the circumference of the sidewall 1012 to assure that, as the central column 1006 of the spacer 1002 is threaded into the central cavity 1016 of the spacer holder 1004, the flexible tab 1024 stays engaged with the ratchet teeth. The engagement between the ratchet teeth on the spacer holder 1004 and the flexible tab 1024 only allows the spacer 1002 to be rotated in one direction with respect to the spacer holder 1004. As a result, the central column 1006 of the spacer 1002 may be threaded into the central cavity 1016 of the spacer holder 1004, but is kept from being unthreaded from the central cavity 1016 of the spacer holder 1004 by the locking engagement of between the ratchet teeth and the flexible tab 1024.

Alternatively, as shown in FIG. 108, a flange 1026 may extend from the proximal end surface of the sidewall 1012 of the spacer holder 1004. The flange 1026 includes a plurality of ratchet teeth configured to engage a flexible tab 1028 that extends in a radial direction from the proximal flange 1008 of the spacer 1002. The flange 1026 on which the ratchet teeth are positioned is configured around the circumference of the sidewall 1012 of the spacer holder 1004 to assure that, as the central column 1006 of the spacer 1002 is threaded into the central cavity 1016 of the spacer holder 1004, the flexible tab 1028 stays engaged with the ratchet teeth.

The bottom portion 1014 of the spacer holder 1004 may be provided at a variety of thicknesses as shown in FIG. 107 in order to provide another dimension of adjustability for containers having different fill volumes.

Referring to FIGS. 109 and 110, a spacer assembly 1100 according to a further aspect of the present invention is shown. The spacer assembly 1100 has a spacer 1102 and a spacer holder 1104. The spacer 1102 has a central column 1106 and a proximal flange 1108. The spacer holder 1104 is received by the stopper 1110 and comprises a sidewall 1112 extending in a proximal direction from a bottom portion 1114. The sidewall 1112 and the bottom portion 1114 define a central cavity 1116 that receives the central column 1106 of the spacer 1102. The spacer holder 1104 may be attached to the stopper 1010 using any suitable method including, but not limited to, adhesive, a threaded connection, and a snap-fit connection. The spacer 1102 includes a protrusion 1118 extending axially in a distal direction from the proximal bottom surface 1120 of the central column 1106. The protrusion 1118 extends around less than half of the circumference of the proximal bottom surface 1120 of the central column 1106. The spacer holder 1104 includes a protrusion 1122 extending axially into the central cavity 1116 from the bottom portion 1114 of the spacer holder 1104. The protrusion 1122 extends around less than half of the circumference of the bottom portion 1114 of the spacer holder 1004. When the spacer 1102 is in a first position, as shown in FIG. 109, the protrusion 1118 on the spacer 1102 contacts the bottom portion 1114 of the spacer holder 1104 and the protrusion 1122 on the spacer holder 1104 contacts the proximal bottom surface 1120 of the spacer 1102 such that the spacer assembly has a first length. When the spacer 1102 is in a second position, as shown in FIG. 110, the protrusion 1118 on the spacer 1102 contacts the protrusion 1122 on the spacer holder 1104 such that the spacer assembly has a second length that is greater than the first length. While a specific embodiment using a spacer and a spacer holder having configurations that allow for the length of the spacer assembly to be changed based on the relative position of the spacer to the spacer holder has been described, other similar configurations may also be utilized.

Referring to FIG. 111, a spacer assembly 1200 according to a further aspect of the present invention is shown. The spacer assembly 1200 has a spacer 1202 and a spacer holder 1204. The spacer 1202 has a central column 1206 and a proximal flange 1208. The spacer holder 1204 is received by the stopper 1210 and comprises a sidewall 1212 extending in a proximal direction from a bottom portion 1214. The sidewall 1212 and the bottom portion 1214 define a central cavity 1216 that receives the central column 1206 of the spacer 1202. The spacer holder 1204 may be attached to the stopper 1210 using any suitable method including, but not limited to, adhesive, a threaded connection, and a snap-fit connection. The inner surface of sidewall 1212 of the spacer holder 1204 includes a non-overhauling threaded portion 1218 that engages a corresponding non-overhauling threaded portion 1220 in the outer surface of the central column 1206 of the spacer 1202. A non-overhauling thread as used herein results in a threaded connection where application of torque to the first component of the threaded system will cause the first component to rotate with respect to the second component, but no amount of axial force applied to the first component will cause it to rotate with respect to the second component. In the present embodiment, the threaded portion 1220 of the central column 1206 of the spacer 1202 and the threaded portion 1218 of the sidewall 1212 of the spacer holder 1204 are configured such that after torque is applied to the spacer 1202 to threadingly attach it to the spacer holder 1204, application of a subsequent axial force will not cause the spacer 1202 to turn with respect to the spacer holder 1204. At least a portion of the threaded portion 1220 in the outer surface of the central column 1206 of the spacer 1202 may have threads that extend radially outward to increase the locking engagement between the threaded portion 1218 of the spacer holder 1204 and the threaded portion 1220 of the spacer 1202. In addition or alternatively, as shown in FIG. 112, the threaded portion 1220 of the spacer may have threads 1224 with an upper outer face 1226 that is angled downward in the proximal direction and a bottom outer face 1228 that extends in a radial direction forming a pointed tooth-shaped structure. When an axial force in the distal direction, as shown by the arrow 1230, is placed on the spacer 1202 in order to move the stopper 1210 in the distal direction, the pointed threads 1224 dig into the sidewall 1212 of the spacer holder 1204 to lock the spacer 1202 to the spacer holder 1204.

Figure 115:
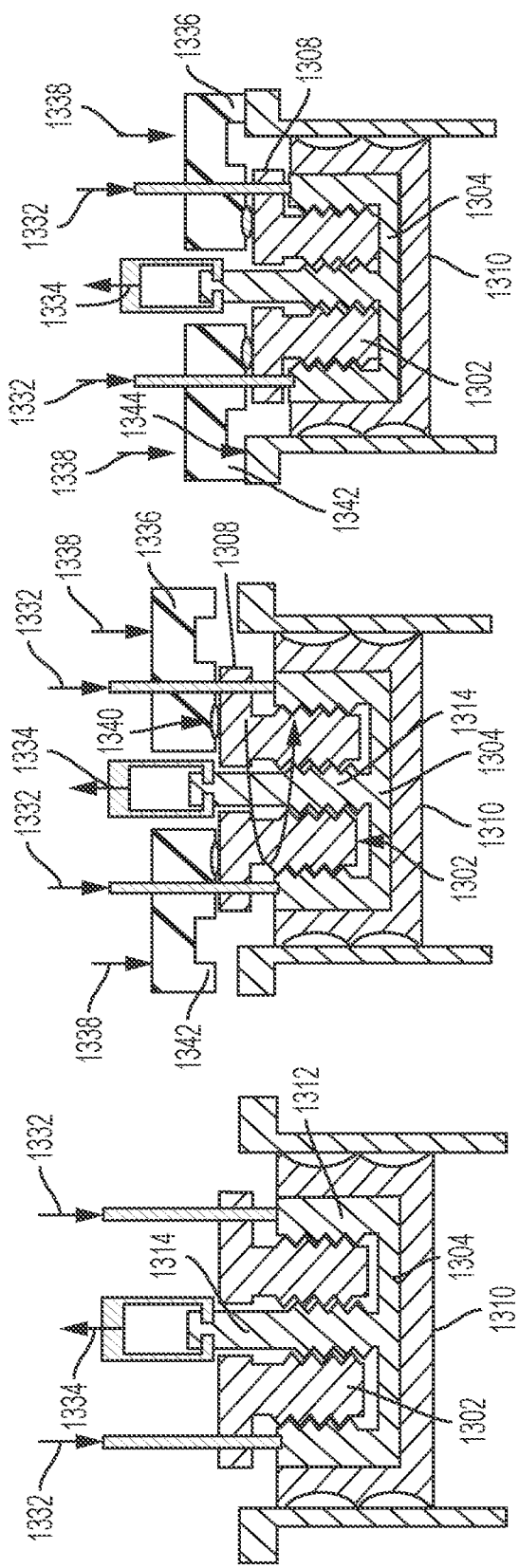

Referring to FIGS. 113-115, a spacer assembly 1300 according to a further aspect of the present invention is shown. The spacer assembly 1300 has a spacer 1302 and a spacer holder 1304. The spacer 1302 has an annular ring 1306 extending from a proximal flange 1308. The spacer holder 1304 is received by the stopper 1310 and comprises a sidewall 1312 and a central post 1314 both extending in a proximal direction from a bottom portion 1316. The sidewall 1312, the central post 1314, and the bottom portion 1316 define an annular cavity 1318 that receives the annular ring 1306 of the spacer 1302. The spacer holder 1304 may be attached to the stopper 1310 using any suitable method including, but not limited to, adhesive, a threaded connection, and a snap-fit connection. The inner surface of the sidewall 1312 of the spacer holder 1304 includes an overhauling threaded portion 1320 that engages a corresponding overhauling threaded portion 1322 in the outer surface of the annular ring 1306 of the spacer 1302, and the outer surface of the central post 1314 includes a non-overhauling threaded portion 1324 that engages a corresponding non-overhauling threaded portion 1326 in the inner surface of the annular ring 1306 of the spacer 1302. A non-overhauling threaded portion as used herein results in a threaded connection where application of torque to a first component of the threaded system will cause the first component to rotate with respect to the second component, but no amount of axial force applied to the first component will cause it to rotate with respect to the second component. An overhauling threaded portion as used herein results in a threaded connection where application of either torque or an axial force to a first component of the threaded system will cause the component to rotate with respect to the second component. The threads of the overhauling threaded portions and the threads of the non-overhauling threaded portions may have the same pitch.

In the present embodiment, as shown in FIG. 113, when a proximal axial force, indicated by arrow 1328, is applied the central post 1314, the load path for a distal axial force, indicated by arrow 1330, is directed through the overhauling threaded connection between the overhauling threaded portion 1320 in the inner surface of the sidewall 1312 of the spacer holder 1304 and the overhauling threaded portion 1322 in the outer surface of the annular ring 1306 of the spacer 1302. Because this threaded connection has overhauling threads, the axial force 1330 causes the spacer 1302 to rotate and thread into the annular cavity 1318 of the spacer holder 1304. When the force 1328 is released, the load path for an axial force 1330 is directed through the non-overhauling threaded connection between the non-overhauling threaded portion 1324 in the outer surface of the central post 1314 of the spacer holder 1304 and the non-overhauling threaded portion 1326 in the inner surface of the annular ring 1306 of the spacer 1302 (FIG. 114). Because this threaded connection has non-overhauling threads, the axial force 1330 does not cause the spacer 1302 to rotate such that movement of the spacer 1302 with respect to the spacer holder 1304 is restricted.

FIGS. 115A-115C show how the spacer assembly 1300 is assembled. In a first step, shown in FIG. 115A, a distal axial force, indicated by arrow 1332, is applied to the proximal end of the sidewall 1312 of the spacer holder 1304 and a proximal axial force, indicated by arrow 1334, is applied to the central post 1314. A fixture 1336 is then used to apply a proximal axial force, indicated by arrow 1338, to the proximal flange 1308 of the spacer 1302 (FIG. 115B). The fixture 1336 has bearing surfaces 1340 that contact the proximal flange 1308 of the spacer 1302 allowing the spacer 1302 to rotate. When a distally extending flange 1342 on the fixture 1336 contacts the proximal end 1344 of the container 1344, the rotation of the spacer 1302 stops as the proximal axial load 1338 is transferred to the container 1344 (FIG. 115C).

Referring to FIGS. 116 and 117, a spacer assembly 1400 according to a further aspect of the present invention is shown. The spacer assembly 1400 has a spacer 1402, a spacer holder 1404, and a locking pin 1406. The spacer 1402 has a sidewall 1408 extending in a proximal direction from a bottom portion 1410 and a proximal flange 1412. The sidewall 1408 and the bottom portion 1410 define a recess 1414 that receives the locking pin 1406. The spacer holder 1404 is received by the stopper 1416 and comprises a sidewall 1418 extending in a proximal direction from a bottom portion 1420. The sidewall 1418 and the bottom portion 1420 define a central cavity 1422 that receives the spacer 1402. The spacer holder 1404 may be attached to the stopper 1416 using any suitable method including, but not limited to, adhesive, a threaded connection, and a snap-fit connection. The inner surface of sidewall 1418 of the spacer holder 1404 includes a threaded portion 1424 that engages a corresponding threaded portion 1426 in the outer surface of the sidewall 1408 of the spacer 1402. After the spacer 1402 is threaded into the central cavity 1422 of the spacer holder 1404 such that the spacer assembly 1400 has the desired length, the locking pin 1406 is inserted into the recess 1414 of the spacer 1402. The locking pin 1406 has substantially the same shape as the recess 1414 of the spacer 1402. The locking pin 1406 keeps the threaded portion 1426 of the sidewall 1408 of the spacer 1402 in good contact with the threaded portion 1424 of the sidewall 1418 of the spacer holder 1404, thereby creating a locking engagement between the sidewall 1408 of the spacer 1402 and the sidewall 1418 of the spacer holder 1404.

Referring to FIG. 118, a spacer assembly 1500 according to a further aspect of the present invention is shown. The spacer assembly 1500 has a spacer 1502, a spacer holder 1504, and an expandable container 1506. The spacer 1502 has a sidewall 1508 extending in a distal direction from a proximal flange 1510. The spacer holder 1504 is received by the stopper 1512 and comprises a sidewall 1514 extending in a proximal direction from a bottom portion 1516. The sidewall 1514 and the bottom portion 1516 define a central cavity 1518 that receives the sidewall 1508 of the spacer 1502. The spacer holder 1504 may be attached to the stopper 1512 using any suitable method including, but not limited to, adhesive, a threaded connection, and a snap-fit connection. An opening having a valve 1520 extends through the proximal flange 1510 of the spacer 1502 and into the expandable container 1506. The expandable container 1506 may be filled with air or any other suitable fluid via the valve 1520 in order to change the distance that the proximal flange 1510 is separated from the proximal end of the sidewall 1514 of the spacer holder 1504, thereby changing the length of the spacer assembly 1600.

An adjustable plunger assembly 1700 may be provided as an alternative to an adjustable spacer assembly. In this embodiment, shown in FIG. 119, the container remains stationary and the valve assembly is configured to pierce the septum without any movement of the container. A single plunger assembly 1700 comprising a plunger 1702 having a central passageway 1704, a plunger extension 1706, and a biasing member 1708 is provided. The inner surface of the central passageway 1704 includes a threaded portion 1710 that engages a corresponding threaded portion 1712 in the outer surface of the plunger extension 1706. During assembly of the drug delivery system, the distance that the plunger extension 1706 extends beyond the distal end 1714 of the plunger 1702 can be changed by adjusting the length of the plunger extension 1706 that is inserted into the central passageway 1704 of the plunger 1702. The plunger assembly 1700 is adjusted by rotating the plunger extension 1706 until the distal end 1716 of the plunger extension 1706 contacts a standard spacer 1718 attached to the stopper 1720. In this manner, the plunger extension 1706 replaces the adjustable spacer assemblies described above while still allowing containers having different fill volumes to be used.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A drive assembly for a drug delivery system, the drive assembly comprising:
a plunger member configured to engage and move a stopper within a container, the plunger member having a first position and a second position axially spaced from the first position;
a biasing member configured to move the plunger member from the first position to the second position; and
an adjustable spacer assembly positioned between the plunger member and the stopper,
wherein the spacer assembly comprises a spacer element and a holder to which the spacer element is attached,
wherein the spacer element is moveable relative to the holder to modify an axial length of the spacer assembly by a predetermined axial distance,
wherein the holder includes helically arranged and radially spaced detents and the spacer element includes a spring detent arm, and
wherein an end of the spring detent arm is configured to pass over the helically arranged and radially spaced detents in one direction to permit rotation and axial displacement of the spacer element away from the holder.

2. The assembly of claim 1, wherein the holder is attached to the stopper and the spacer element is attached to the holder by a threaded engagement.

3. The assembly of claim 1, wherein when the spacer element is in a first position with respect to the holder, the spacer assembly has a first length in a longitudinal direction, and when the spacer element is in a second position with respect to the holder, the spacer assembly has a second length in the longitudinal direction, the second length being greater than the first length.

4. The assembly of claim 1, wherein the holder is fixedly connected to the stopper.

5. The assembly of claim 1, wherein an end of the spring detent arm is configured to engage one of the helically arranged and radially spaced detents of the holder to prevent rotation and axial displacement of the spacer element toward the holder.

6. The assembly of claim 1, wherein the end of the spring detent arm is configured to pass over the helically arranged and radially spaced detents until a proximal face of the spacer element has a predetermined distance from the proximal end of the container.

7. The assembly of claim 1, wherein each of the helically arranged and radially spaced detents comprises a depth from a proximal face of the spacer element, and wherein each depth of the helically arranged and radially spaced detents decreases from a start depth of the helically arranged and radially spaced detents to an end depth of the helically arranged and radially spaced detents.

8. The assembly of claim 1, wherein the spacer element is rotationally displaceable in one direction relative to the holder.

9. A drug delivery system for injecting a medicament, the system comprising:
- a container configured to receive a medicament, the container comprising a stopper configured to move within the container and a closure;
- a drive assembly comprising:
    - a plunger member configured to engage and move the stopper within the container, the plunger member having a first position and a second position axially spaced from the first position;
    - a biasing member configured to move the plunger member from the first position to the second position; and
    - an adjustable spacer assembly positioned between the plunger member and the stopper,
    - wherein the spacer assembly comprises a spacer element and a holder to which the spacer element is attached,
    - wherein the spacer element is moveable relative to the holder to modify an axial length of the spacer assembly by a predetermined axial distance,
    - wherein the holder includes helically arranged and radially spaced detents and the spacer element includes a spring detent arm, and
    - wherein an end of the spring detent arm is configured to pass over the helically arranged and radially spaced detents in one direction to permit rotation and axial displacement of the spacer element away from the holder; and
- a needle actuator assembly comprising a needle configured to be placed in fluid communication with the container.

10. The system of claim 9, wherein the holder is attached to the stopper and the spacer element is attached to the holder by a threaded engagement.

11. The system of claim 9, wherein when the spacer element is in a first position with respect to the holder, the spacer assembly has a first length in a longitudinal direction, and when the spacer element is in a second position with respect to the holder, the spacer assembly has a second length in the longitudinal direction, the second length being greater than the first length.

12. The system of claim 9, wherein the holder is fixedly connected to the stopper.

13. The system of claim 9, wherein an end of the spring detent arm is configured to engage one of the helically arranged and radially spaced detents of the holder to prevent rotation and axial displacement of the spacer element toward the holder.

14. The system of claim 9, wherein the end of the spring detent arm is configured to pass over the helically arranged and radially spaced detents until a proximal face of the spacer element has a predetermined distance from the proximal end of the container.

15. The system of claim 9, wherein each of the helically arranged and radially spaced detents comprises a depth from a proximal face of the spacer element, and wherein each depth of the helically arranged and radially spaced detents decreases from a start depth of the helically arranged and radially spaced detents to an end depth of the helically arranged and radially spaced detents.

16. The system of claim 9, wherein the spacer element is rotationally displaceable in one direction relative to the holder.

* * * * *